(12) United States Patent
Boudreault et al.

(10) Patent No.: US 10,411,201 B2
(45) Date of Patent: Sep. 10, 2019

(54) ORGANIC ELECTROLUMINESCENT MATERIALS AND DEVICES

(71) Applicant: Universal Display Corporation, Ewing, NJ (US)

(72) Inventors: Pierre-Luc T. Boudreault, Pennington, NJ (US); Harvey Wendt, Medford Lakes, NJ (US); Chuanjun Xia, Lawrenceville, NJ (US)

(73) Assignee: Universal Display Corporation, Ewing, NJ (US)

( * ) Notice: Subject to any disclaimer, the term of this patent is extended or adjusted under 35 U.S.C. 154(b) by 277 days.

(21) Appl. No.: 14/851,917

(22) Filed: Sep. 11, 2015

(65) Prior Publication Data
US 2016/0133860 A1 May 12, 2016

Related U.S. Application Data

(63) Continuation-in-part of application No. 14/539,412, filed on Nov. 12, 2014.
(Continued)

(51) Int. Cl.
*H01L 51/00* (2006.01)
*C07F 15/00* (2006.01)
(Continued)

(52) U.S. Cl.
CPC ...... *H01L 51/0085* (2013.01); *C07F 15/0033* (2013.01); *C09K 11/025* (2013.01);
(Continued)

(58) Field of Classification Search
CPC .............. H01L 51/0085; H01L 51/0074; H01L 51/0071; H01L 51/0072; H01L 51/5016;
(Continued)

(56) References Cited

U.S. PATENT DOCUMENTS 4,769,292 A 9/1988 Tang et al.
5,061,569 A 10/1991 VanSlyke et al.
(Continued)

FOREIGN PATENT DOCUMENTS

CN 101160370 4/2008
CN 102439019 5/2012
(Continued)

OTHER PUBLICATIONS

Office Action dated May 22, 2018 for corresponding Chinese Patent Application No. 201510760393.0.
Adachi, Chihaya et al., "Organic Electroluminescent Device Having a Hole Conductor as an Emitting Layer," Appl. Phys. Lett., 55(15): 1489-1491 (1989).
Adachi, Chihaya et al., "Nearly 100% Internal Phosphorescence Efficiency in an Organic Light Emitting Device," J. Appl. Phys., 90(10): 5048-5051 (2001).
Adachi, Chihaya et al., "High-Efficiency Red Electrophosphorescence Devices," Appl. Phys. Lett., 78(11)1622-1624 (2001).
(Continued)

*Primary Examiner* — Alexander C Kollias
(74) *Attorney, Agent, or Firm* — Duane Morris LLP

(57) ABSTRACT

A compound having a formula $M(L_A)_x(L_B)_y(L_C)_z$, where ligand $L_A$ is

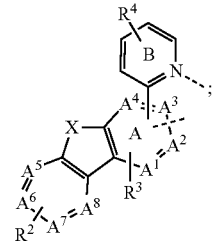

ligand $L_B$ is

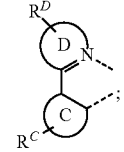

and ligand $L_C$ is

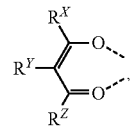

is disclosed. In formula $M(L_A)_x(L_B)_y(L_C)_z$, M is a metal having an atomic number greater than 40; x is 1 or 2; y is 0, 1, or 2; z is 0, 1, or 2; x+y+z is the oxidation state of the metal M; $A^1$-$A^8$ are carbon or nitrogen; ring B is bonded to ring A through a C—C bond; M is bonded to ring A through a M-C bond; X is O, S, Se, CRR', or $NR^1$; rings C and D are each independently a 5 or 6-membered carbocyclic or heterocyclic ring; $R^3$ represents mono, or di-substitution, or no substitution; $R^2$, $R^C$, and $R^D$ each independently represent mono, di, tri, or tetra-substitution, or no substitution; $R^4$ represents mono, di, tri, or tetra-substitution; at least one $R^4$ is a five-membered or six-membered heterocyclic ring which can be further substituted by $R^E$; where $R^E$ represents mono, di, tri, or tetra-substitution, or no substitution; each R substituent is independently selected from a variety of moieties; and any adjacent R substitutents are optionally joined to form a ring.

22 Claims, 3 Drawing Sheets

Related U.S. Application Data

(60) Provisional application No. 62/089,397, filed on Dec. 9, 2014.

(51) Int. Cl.
*C09K 11/06* (2006.01)
*C09K 11/02* (2006.01)
*H01L 51/50* (2006.01)

(52) U.S. Cl.
CPC .......... *C09K 11/06* (2013.01); *H01L 51/0071* (2013.01); *H01L 51/0072* (2013.01); *H01L 51/0074* (2013.01); *C09K 2211/1029* (2013.01); *C09K 2211/1059* (2013.01); *C09K 2211/1088* (2013.01); *C09K 2211/185* (2013.01); *H01L 51/5016* (2013.01)

(58) Field of Classification Search
CPC . C07F 15/0033; C07C 317/48; C07C 311/48; C07D 333/26; C07D 333/36; C07D 295/26; C07D 295/16; C07D 295/155; C07D 295/192; C07D 333/38; C09K 11/025; C09K 11/06; C09K 2211/1088; C09K 2211/1059; C09K 2211/185; C09K 2211/1029
See application file for complete search history.

(56) References Cited

U.S. PATENT DOCUMENTS

| | | |
|---|---|---|
| 5,247,190 A | 9/1993 | Friend et al. |
| 5,703,436 A | 12/1997 | Forrest et al. |
| 5,707,745 A | 1/1998 | Forrest et al. |
| 5,834,893 A | 11/1998 | Bulovic et al. |
| 5,844,363 A | 12/1998 | Gu et al. |
| 6,013,982 A | 1/2000 | Thompson et al. |
| 6,087,196 A | 7/2000 | Sturm et al. |
| 6,091,195 A | 7/2000 | Forrest et al. |
| 6,097,147 A | 8/2000 | Baldo et al. |
| 6,294,398 B1 | 9/2001 | Kim et al. |
| 6,303,238 B1 | 10/2001 | Thompson et al. |
| 6,337,102 B1 | 1/2002 | Forrest et al. |
| 6,468,819 B1 | 10/2002 | Kim et al. |
| 6,528,187 B1 | 3/2003 | Okada |
| 6,687,266 B1 | 2/2004 | Ma et al. |
| 6,835,469 B2 | 12/2004 | Kwong et al. |
| 6,921,915 B2 | 7/2005 | Takiguchi et al. |
| 7,087,321 B2 | 8/2006 | Kwong et al. |
| 7,090,928 B2 | 8/2006 | Thompson et al. |
| 7,154,114 B2 | 12/2006 | Brooks et al. |
| 7,250,226 B2 | 7/2007 | Tokito et al. |
| 7,279,704 B2* | 10/2007 | Walters .................. C09K 11/06 257/40 |
| 7,332,232 B2 | 2/2008 | Ma et al. |
| 7,338,722 B2 | 3/2008 | Thompson et al. |
| 7,393,599 B2 | 7/2008 | Thompson et al. |
| 7,396,598 B2 | 7/2008 | Takeuchi et al. |
| 7,431,968 B1 | 10/2008 | Shtein et al. |
| 7,445,855 B2 | 11/2008 | Mackenzie et al. |
| 7,534,505 B2 | 5/2009 | Lin et al. |
| 8,722,205 B2* | 5/2014 | Xia .................. C07F 15/0033 257/E51.044 |
| 8,795,850 B2* | 8/2014 | Kottas ................. H01L 51/0085 257/E51.044 |
| 8,946,697 B1* | 2/2015 | Ma .................. C07F 15/0033 257/40 |
| 9,193,745 B2* | 11/2015 | Ma .................. C07F 15/0033 |
| 9,397,302 B2 | 7/2016 | Boudreault et al. |
| 9,634,264 B2* | 4/2017 | Beers ................. H01L 51/0085 |
| 9,685,617 B2* | 6/2017 | Beers ................. H01L 51/0085 |
| 10,128,449 B2 | 11/2018 | Saito et al. |
| 10,199,581 B2 | 2/2019 | Boudreault et al. |
| 2002/0034656 A1 | 3/2002 | Thompson et al. |
| 2002/0134984 A1 | 9/2002 | Igarashi |
| 2002/0158242 A1 | 10/2002 | Son et al. |
| 2003/0138657 A1 | 7/2003 | Li et al. |
| 2003/0152802 A1 | 8/2003 | Tsuboyama et al. |
| 2003/0162053 A1 | 8/2003 | Marks et al. |
| 2003/0175553 A1 | 9/2003 | Thompson et al. |
| 2003/0230980 A1 | 12/2003 | Forrest et al. |
| 2004/0036077 A1 | 2/2004 | Ise |
| 2004/0137267 A1 | 7/2004 | Igarashi et al. |
| 2004/0137268 A1 | 7/2004 | Igarashi et al. |
| 2004/0174116 A1 | 9/2004 | Lu et al. |
| 2005/0025993 A1 | 2/2005 | Thompson et al. |
| 2005/0112407 A1 | 5/2005 | Ogasawara et al. |
| 2005/0238919 A1 | 10/2005 | Ogasawara |
| 2005/0244673 A1 | 11/2005 | Satoh et al. |
| 2005/0260441 A1 | 11/2005 | Thompson et al. |
| 2005/0260449 A1 | 11/2005 | Walters et al. |
| 2006/0008670 A1 | 1/2006 | Lin et al. |
| 2006/0202194 A1 | 9/2006 | Jeong et al. |
| 2006/0240279 A1 | 10/2006 | Adamovich et al. |
| 2006/0251923 A1 | 11/2006 | Lin et al. |
| 2006/0263635 A1 | 11/2006 | Ise |
| 2006/0280965 A1 | 12/2006 | Kwong et al. |
| 2007/0128466 A1* | 6/2007 | Nomura ................. C09K 11/06 428/690 |
| 2007/0190359 A1 | 8/2007 | Knowles et al. |
| 2007/0278938 A1 | 12/2007 | Yabunouchi et al. |
| 2008/0015355 A1 | 1/2008 | Schafer et al. |
| 2008/0018221 A1 | 1/2008 | Egen et al. |
| 2008/0106190 A1 | 5/2008 | Yabunouchi et al. |
| 2008/0124572 A1 | 5/2008 | Mizuki et al. |
| 2008/0220265 A1 | 9/2008 | Xia et al. |
| 2008/0297033 A1 | 12/2008 | Knowles et al. |
| 2009/0008605 A1 | 1/2009 | Kawamura et al. |
| 2009/0009065 A1 | 1/2009 | Nishimura et al. |
| 2009/0017330 A1 | 1/2009 | Iwakuma et al. |
| 2009/0030202 A1 | 1/2009 | Iwakuma et al. |
| 2009/0039776 A1 | 2/2009 | Yamada et al. |
| 2009/0045730 A1 | 2/2009 | Nishimura et al. |
| 2009/0045731 A1 | 2/2009 | Nishimura et al. |
| 2009/0101870 A1 | 4/2009 | Prakash et al. |
| 2009/0108737 A1 | 4/2009 | Kwong et al. |
| 2009/0115316 A1 | 5/2009 | Zheng et al. |
| 2009/0165846 A1 | 7/2009 | Johannes et al. |
| 2009/0167162 A1 | 7/2009 | Lin et al. |
| 2009/0179554 A1 | 7/2009 | Kuma et al. |
| 2010/0237334 A1* | 9/2010 | Ma .................. C07D 307/91 257/40 |
| 2010/0244004 A1* | 9/2010 | Xia .................. C07F 15/0033 257/40 |
| 2012/0292601 A1* | 11/2012 | Kottas ................. H01L 51/0085 257/40 |
| 2013/0119354 A1* | 5/2013 | Ma .................. C07F 15/0033 257/40 |
| 2014/0131663 A1* | 5/2014 | Beers ................. H01L 51/0085 257/40 |
| 2014/0131676 A1* | 5/2014 | Beers ................. H01L 51/0085 257/40 |
| 2015/0171348 A1* | 6/2015 | Stoessel ............. C07F 15/0033 252/301.16 |
| 2015/0315222 A1* | 11/2015 | Boudreault ......... H01L 51/0085 257/40 |
| 2016/0133859 A1* | 5/2016 | Boudreault ......... H01L 51/0085 257/40 |
| 2016/0329508 A1* | 11/2016 | Saito ..................... C09K 11/06 |

FOREIGN PATENT DOCUMENTS

| | | |
|---|---|---|
| CN | 103102371 | 5/2013 |
| EP | 0650955 | 5/1995 |
| EP | 1725079 | 11/2006 |
| EP | 2034538 | 3/2009 |
| JP | 200511610 | 1/2005 |
| JP | 2007123392 | 5/2007 |
| JP | 2007254297 | 10/2007 |
| JP | 2008074939 | 4/2008 |
| WO | 01/39234 | 5/2001 |
| WO | 02/02714 | 1/2002 |
| WO | 02015654 | 2/2002 |

(56) References Cited

FOREIGN PATENT DOCUMENTS

| | | |
|---|---|---|
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003898 | 1/2009 |
| WO | 2009008311 | 1/2009 |
| WO | 2009018009 | 2/2009 |
| WO | 2009021126 | 2/2009 |
| WO | 2009050290 | 4/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |

OTHER PUBLICATIONS

Aonuma, Masaki et al., "Material Design of Hole Transport Materials Capable of Thick-Film Formation in Organic Light Emitting Diodes," App. Phys. Lett., 90, Apr. 30, 2007, 183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 1, 4-6 (1999).

Gao, Zhiqiang et al., "Bright-Blue Electroluminescence From a Silyl-Substituted ter-(phenylene-vinylene) derivative," Appl. Phys. Lett., 74(6): 865-867 (1999).

Guo, Tzung-Fang et al., "Highly Efficient Electrophosphorescent Polymer Light-Emitting Devices," Organic Electronics, 1: 15-20 (2000).

Hamada, Yuji et al., "High Luminance in Organic Electroluminescent Devices with Bis(10-hydroxybenzo[h]quinolinato) beryllium as an Emitter, " Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater, 19:739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi et al., "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-926 (2006).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivative as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino) triphenylamine (m-MTDATA), as Hole-Transport Materials," Adv. Mater, 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Lo, Shih-Chun et al., "Blue Phosphorescence from Iridium(III) Complexes at Room Temperature," Chem. Mater., 18 (21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylbory1)-2,2'-bithiophene and 5,5"-Bis (dimesitylbory1)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett., 89:063504-1-063504-3 (2006).

Palilis, Leonidas C., "High Efficiency Molecular Organic Light-Emitting Diodes Based on Silole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Ranjan, Sudhir et al., "Realizing Green Phosphorescent Light-Emitting Materials from Rhenium(1) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91: 209-215 (1997).

Shirota, Yasuhiko et al., "Starburst Molecules Based on pi-Electron Systems as Materials for Organic Electroluminescent Devices," Journal of Luminescence, 72-74:985-991 (1997).

(56) References Cited

OTHER PUBLICATIONS

Sotoyama, Wataru et al., "Efficient Organic Light-Emitting Diodes with Phosphorescent Platinum Complexes Containing N^C^N-Coordinating Tridentate Ligand," Appl. Phys. Lett., 86:153505-1-153505-3 (2005).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

T. Östergård et al., "Langmuir-Blodgett Light-Emitting Diodes of Poly(3-Hexylthiophene) Electro-Optical Characteristics Related to Structure," Synthetic Metals, 88:171-177 (1997).

Takizawa, Shin-ya et al., "Phosphorescent Iridium Complexes Based on 2-Phenylimidazo[1,2-α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

Van Slyke, S. A. et al., "Organic Electroluminescent Devices with Improved Stability," Appl. Phys. Lett., 69 (15):2160-2162 (1996).

Wang, Y. et al., "Highly Efficient Electroluminescent Materials Based on Fluorinated Organometallic Iridium compounds," Appl. Phys. Lett., 79(4):449-451 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Wong, Wai-Yeung, "Multifunctional Iridium Complexes Based on Carbazole Modules as Highly Efficient Electrophosphors," Angew. Chem. Int. Ed., 45:7800-7803 (2006).

Yu, Fang-Fang et al., "Blue fluorescence from the ligand and yellow phosphorescence from the iridium complex: High-efficiency wet-processed white organic light-emitting device" Inorganica Chimica Acta, vol. 390, Jul. 15, 2012, pp. 119-122.

Notice of Reasons for Rejection dated Feb. 5, 2019 for corresponding Japanese Patent Application No. 2015-218247.

* cited by examiner

Ligand L_A            Ligand L_B            Ligand L_C

ORGANIC ELECTROLUMINESCENT MATERIALS AND DEVICES

CROSS-REFERENCE TO RELATED APPLICATIONS

This application is a continuation-in-part application of U.S. application Ser. No. 14/539,412, filed Nov. 12, 2014, the disclosure of which is incorporated herein by reference in its entirety. This application also claims priority under 35 U.S.C. § 119(e) to U.S. Provisional Application Ser. No. 62/089,397, filed Dec. 9, 2014, the disclosure of which is incorporated herein by reference in its entirety.

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and Universal Display Corporation. The agreement was in effect on and before the date the claimed invention was made, and the claimed invention was made as a result of activities undertaken within the scope of the agreement.

FIELD OF THE INVENTION

The present invention relates to compounds for use as emitters and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the following structure:

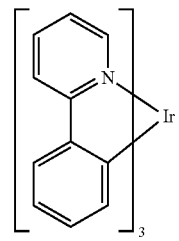

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to one embodiment, a compound having a formula $M(L_A)_x(L_B)_y(L_C)_z$, where the ligand $L_A$ is

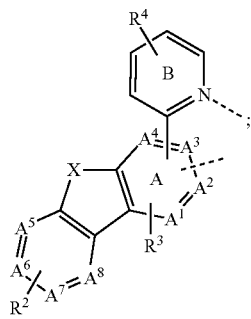

the ligand $L_B$ is

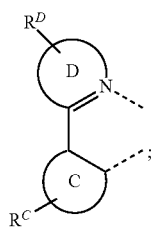

and the ligand $L_C$ is

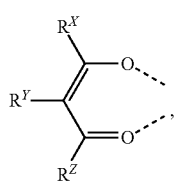

is provided. In the structure of formula $M(L_A)_x(L_B)_y(L_C)_z$:
M is a metal having an atomic number greater than 40;
x is 1, or 2;
y is 0, 1, or 2;
z is 0, 1, or 2;
x+y+z is the oxidation state of the metal M;
$A^1, A^2, A^3, A^4, A^5, A^6, A^7$, and $A^8$ are carbon or nitrogen;
ring B is bonded to ring A through a C—C bond;
M is bonded to ring A through a M-C bond;
X is selected from the group consisting of O, S, Se, CRR', and $NR^1$;
rings C and D are each independently a 5 or 6-membered carbocyclic or heterocyclic ring;
$R^3$ represents mono, or di-substitution, or no substitution;
$R^2$, $R^C$, and $R^D$ each independently represent mono, di, tri, or tetra-substitution, or no substitution;
$R^4$ represents mono, di, tri, or tetra-substitution;
at least one $R^4$ is a five-membered or six-membered heterocyclic ring which can be further substituted by $R^E$;
$R^E$ represents mono, di, tri, or tetra-substitution, or no substitution; each of R, R', $R^1$, $R^2$, $R^3$, $R^4$, $R^C$, $R^D$, $R^X$, $R^Y$, $R^Z$ and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent substitutents of R, R', $R^1$, $R^2$, $R^3$, $R^4$, $R^C$, $R^D$, $R^X$, $R^Y$, $R^Z$ and $R^E$ are optionally joined to form a ring.

In some embodiments of the compound, at least one $R^4$ of the ligand $L_A$ is a six-membered heterocyclic ring having at least two nitrogen atoms where the only heteroatom is nitrogen, such as a triazine moiety.

According to another embodiment, a device comprising one or more organic light emitting devices is also provided. At least one of the one or more organic light emitting devices can include an anode, a cathode, and an organic layer, disposed between the anode and the cathode, wherein the organic layer can include the compound of Formula $M(L_A)_x(L_B)_y(L_C)_z$. The device can be a consumer product, an electronic component module, an organic light-emitting device, and/or a lighting panel.

According to yet another embodiment, a formulation containing a compound of Formula $M(L_A)_x(L_B)_y(L_C)_z$ is provided.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
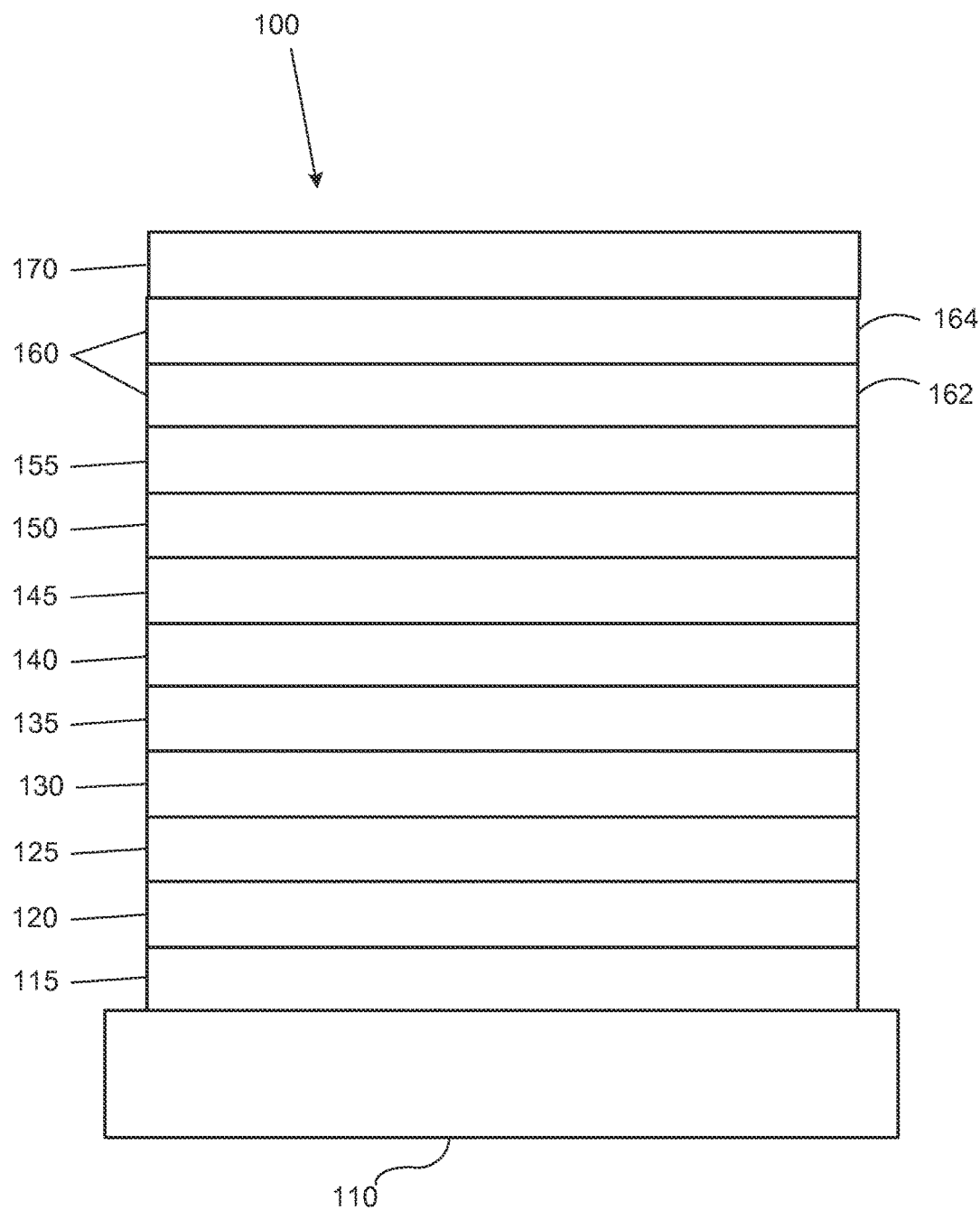
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
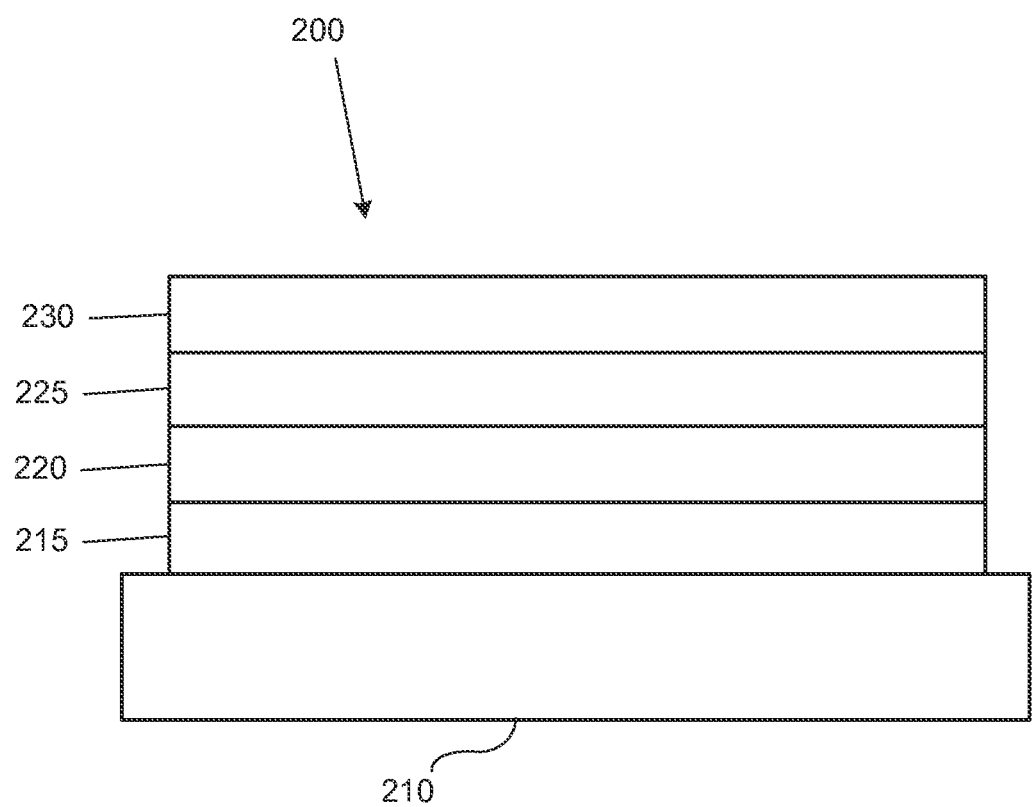
FIG. 2 shows an inverted organic light emitting device that does not have a separate electron transport layer.
Figure 3:
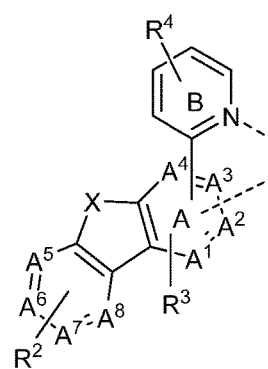
FIG. 3 shows ligand $L_A$, ligand $L_B$, and ligand $L_C$ as described herein.
Figure 3:
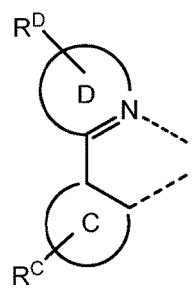
Figure 3:
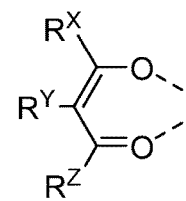

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkynyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzothiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

According to one embodiment, a compound having a formula $M(L_A)_x(L_B)_y(L_C)_z$, where the ligand $L_A$ is

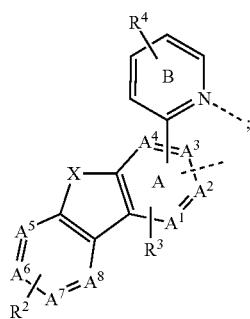

the ligand $L_B$ is

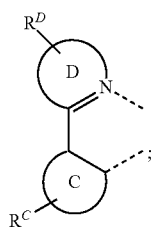

and the ligand $L_C$ is

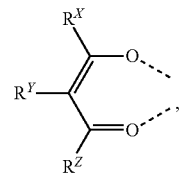

is disclosed. In the structure of formula $M(L_A)_x(L_B)_y(L_C)_z$:

M is a metal having an atomic number greater than 40;

x is 1, or 2;

y is 0, 1, or 2;

z is 0, 1, or 2;

x+y+z is the oxidation state of the metal M;

$A^1, A^2, A^3, A^4, A^5, A^6, A^7$, and $A^8$ are carbon or nitrogen;

ring B is bonded to ring A through a C—C bond;

M is bonded to ring A through a M-C bond;

X is selected from the group consisting of O, S, Se, CRR', and $NR^1$;

rings C and D are each independently a 5 or 6-membered carbocyclic or heterocyclic ring;

$R^3$ represents mono, or di-substitution, or no substitution;

$R^2$, $R^C$, and $R^D$ each independently represent mono, di, tri, or tetra-substitution, or no substitution;

$R^4$ represents mono, di, tri, or tetra-substitution;

at least one $R^4$ is a five-membered or six-membered heterocyclic ring which can be further substituted by $R^E$;

$R^E$ represents mono, di, tri, or tetra-substitution, or no substitution;

each of R, R', $R^1$, $R^2$, $R^3$, $R^4$, $R^C$, $R^D$, $R^X$, $R^Y$, $R^Z$ and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and any adjacent substitutents of R, R', $R^1$, $R^2$, $R^3$, $R^4$, $R^C$, $R^D$, $R^X$, $R^Y$, $R^Z$ and $R^E$ are optionally joined to form a ring.

As used herein, unless otherwise specified, the generalized structure of Ligand $L_A$

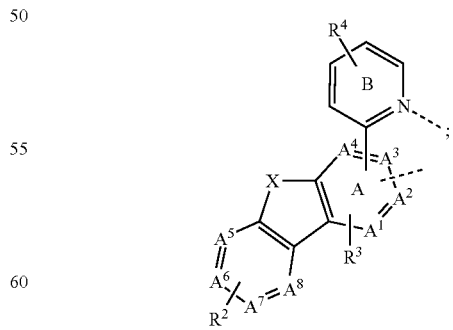

encompasses both instances where the heteroatom X of the polycyclic moiety faces Ring B, and instances where the heteroatom X of the polycyclic moiety faces away from Ring B, as shown in formula I

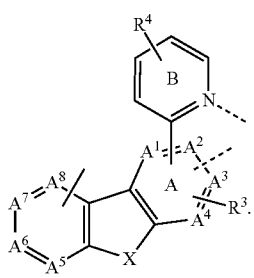

In some embodiments, M is selected from the group consisting of Ir, Rh, Re, Ru, Os, Pt, Au, and Cu. In some embodiments, M is Ir.

In some embodiments, the compound has the formula $M(L_A)_2(L_C)$. In some embodiments, the compound has the formula $M(L_A)(L_B)_2$.

In some embodiments, $A^1$, $A^2$, $A^3$, $A^4$, $A^5$, $A^6$, $A^7$, and $A^8$ are carbon. In some embodiments, exactly one of $A^1$, $A^2$, $A^3$, $A^4$, $A^5$, $A^6$, $A^7$, and $A^8$ is nitrogen. In some embodiments, exactly two of $A^1$, $A^2$, $A^3$, $A^4$, $A^5$, $A^6$, $A^7$, and $A^8$ are nitrogen. In some embodiments, exactly one of $A^5$, $A^6$, $A^7$, and $A^8$ is nitrogen, while $A^1$, $A^2$, $A^3$, and $A^4$ are carbon.

In some embodiments, X is O. In some embodiments, X is $NR^1$. In some embodiments, X is CRR'.

In some embodiments, $R^2$ is substituted at the $A^7$ position. In some embodiments, at least one $R^4$ is a five-membered or six-membered aromatic heterocyclic ring. In some embodiments, exactly one $R^4$ is a five-membered or six-membered aromatic heterocyclic ring.

In some embodiments, at least one $R^4$ is a six-membered aromatic heterocyclic ring where the only heteroatom is nitrogen. In some embodiments, exactly one $R^4$ is a six-membered aromatic heterocyclic ring where the only heteroatom is nitrogen. In some embodiments, there is at least one $R^4$ or exactly one $R^4$ that is a six-membered aromatic heterocyclic ring, where the only heteroatom is nitrogen, and where there are one or two nitrogen atoms.

In some embodiments, at least one $R^4$ is pyridine. In some embodiments, exactly one $R^4$ is pyridine. In some embodiments, R4 is a pyridine that is attached meta to the N-M bond of ring B.

In some embodiments, the exactly one $R^4$ or at least one $R^4$ is pyridine that is substituted by alkyl. In some embodiments, the exactly one $R^4$ or at least one $R^4$ is pyridine that is substituted by alkyl at a position ortho to the N of the pyridine.

In some embodiments, $L_B$ has the formula

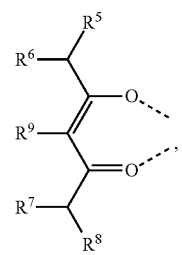

where $R^5$, $R^6$, $R^7$, and $R^8$ are independently selected from group consisting of alkyl, cycloalkyl, aryl, and heteroaryl; and where at least one of $R^5$, $R^6$, $R^7$, and $R^8$ has at least two C atoms. In some embodiments, $R^9$ is hydrogen.

In some embodiments, each of R, R', $R^1$, $R^2$, $R^3$, $R^4$, $R^C$, $R^D$, $R^X$, $R^Y$, $R^Z$ and $R^E$ is independently selected from group consisting of hydrogen, deuterium, alkyl, cycloalkyl, and combinations thereof. In some embodiments, each of R, R', $R^1$, $R^2$, $R^3$, $R^4$, $R^C$, $R^D$, $R^X$, $R^Y$, $R^Z$ and $R^E$ is independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclobutyl, cyclopentyl, cyclohexyl, and combinations thereof.

In some embodiments, ring C is benzene, and ring D is pyridine.

In some embodiments, $L_A$ is selected from the group consisting of:

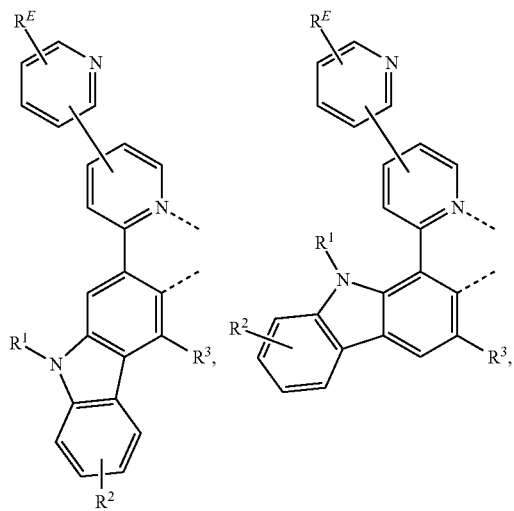

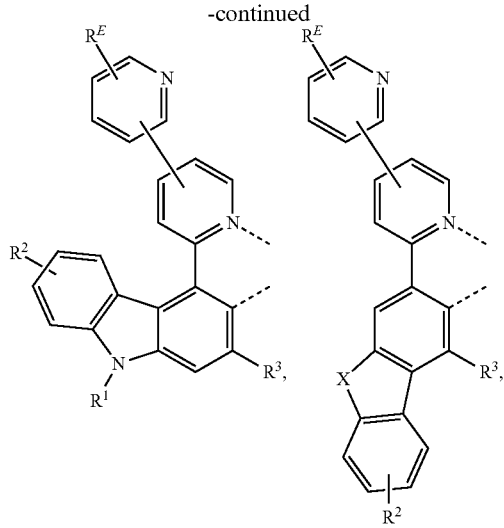
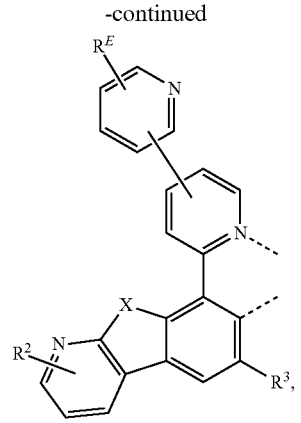
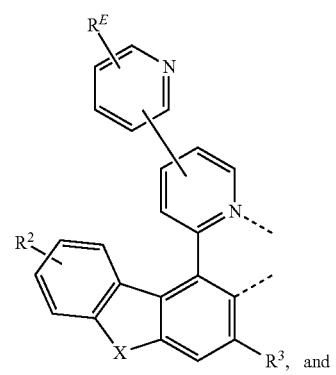
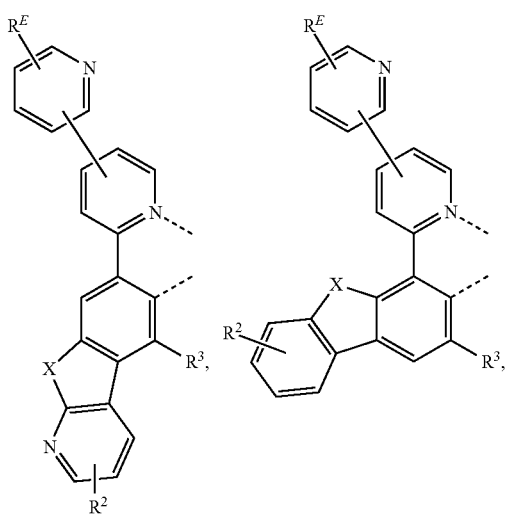
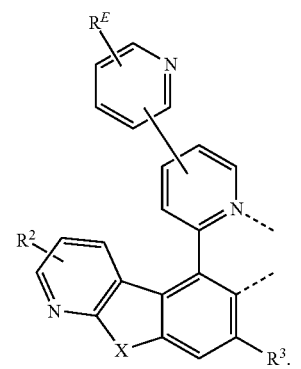

In some more specific embodiments, $L_A$ is selected from the group consisting of:

$L_{A1}$ through $L_{A8}$, each represented by the formula:

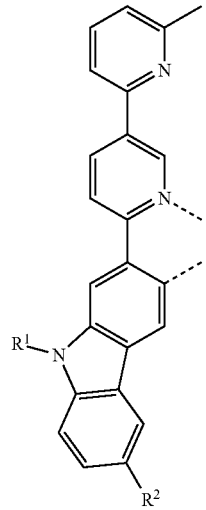

wherein
in $L_{A1}$: $R^1 = R^{A1}$ and $R^2 = R^{B1}$,
in $L_{A2}$: $R^1 = R^{A2}$ and $R^2 = R^{B1}$,
in $L_{A3}$: $R^1 = R^{A3}$, $R^2 = R^{B1}$,
in $L_{A4}$: $R^1 = R^{A4}$, $R^2 = R^{B1}$,
in $L_{A5}$: $R^1 = R^{A1}$, $R^2 = R^{B2}$,
in $L_{A6}$: $R^1 = R^{A2}$, $R^2 = R^{B2}$,
in $L_{A7}$: $R^1 = R^{A3}$, $R^2 = R^{B2}$, and
in $L_{A8}$: $R^1 = R^{A4}$, $R^2 = R^{B2}$,, $L_{A9}$ through $L_{A16}$, each represented by the formula:

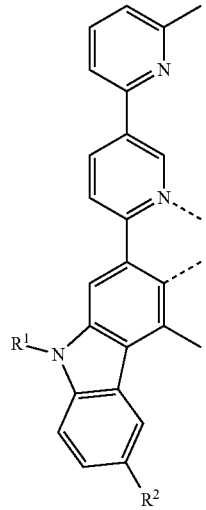

wherein
in $L_{A9}$: $R^1 = R^{A1}$, $R^2 = R^{B1}$,
in $L_{A10}$: $R^1 = R^{A2}$, $R^2 = R^{B1}$,
in $L_{A11}$: $R^1 = R^{A3}$, $R^2 = R^{B1}$,
in $L_{A12}$: $R^1 = R^{A4}$, $R^2 = R^{B1}$,
in $L_{A13}$: $R^1 = R^{A1}$, $R^2 = R^{B2}$,
in $L_{A14}$: $R^1 = R^{A2}$, $R^2 = R^{B2}$,
in $L_{A15}$: $R^1 = R^{A3}$, $R^2 = R^{B2}$, and
in $L_{A16}$: $R^1 = R^{A4}$, $R^2 = R^{B2}$,, $L_{A17}$ through $L_{A24}$, each represented by the formula:

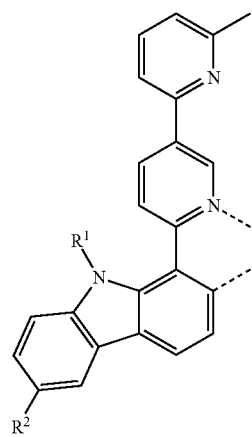

wherein
$L_{A17}$: $R^1 = R^{A1}$, $R^2 = R^{B1}$,
in $L_{A18}$: $R^1 = R^{A2}$, $R^2 = R^{B1}$,
in $L_{A19}$: $R^1 = R^{A3}$, $R^2 = R^{B1}$,
in $L_{A20}$: $R^1 = R^{A4}$, $R^2 = R^{B1}$,
in $L_{A21}$: $R^1 = R^{A1}$, $R^2 = R^{B2}$,
in $L_{A22}$: $R^1 = R^{A2}$, $R^2 = R^{B2}$,
in $L_{A23}$: $R^1 = R^{A3}$, $R^2 = R^{B2}$, and
in $L_{A24}$: $R^1 = R^{A4}$, $R^2 = R^{B2}$,, $L_{A25}$ through $L_{A32}$, each represented by the formula:

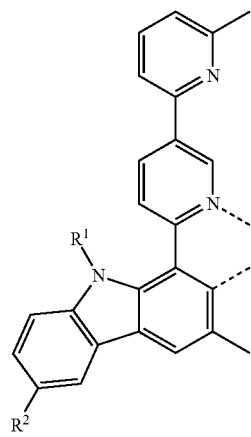

wherein
in $L_{A25}$: $R^1 = R^{A1}$, $R^2 = R^{B1}$,
in $L_{A26}$: $R^1 = R^{A2}$, $R^2 = R^{B1}$,
in $L_{A27}$: $R^1 = R^{A3}$, $R^2 = R^{B1}$,
in $L_{A28}$: $R^1 = R^{A4}$, $R^2 = R^{B1}$,
in $L_{A29}$: $R^1 = R^{A1}$, $R^2 = R^{B2}$,
in $L_{A30}$: $R^1 = R^{A2}$, $R^2 = R^{B2}$,
in $L_{A31}$: $R^1 = R^{A3}$, $R^2 = R^{B2}$, and
in $L_{A32}$: $R^1 = R^{A4}$, $R^2 = R^{B2}$,,

| L$_{A33}$ through L$_{A40}$, each represented by the formula: | L$_{A41}$ through L$_{A48}$, each represented by the formula: |
|---|---|
| 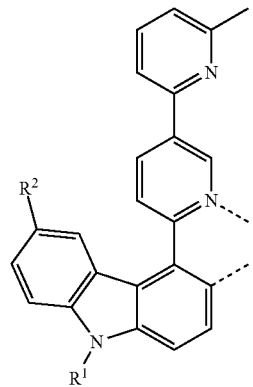 | 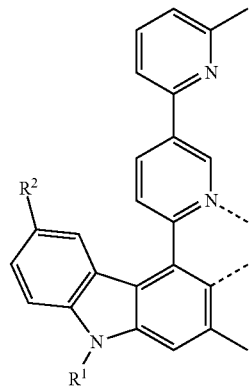 |
| wherein<br>in L$_{A33}$: R$^1$ = R$^{41}$, R$^2$ = R$^{B1}$,<br>in L$_{A34}$: R$^1$ = R$^{42}$, R$^2$ = R$^{B1}$,<br>in L$_{A35}$: R$^1$ = R$^{43}$, R$^2$ = R$^{B1}$,<br>in L$_{A36}$: R$^1$ = R$^{44}$, R$^2$ = R$^{B1}$,<br>in L$_{A37}$: R$^1$ = R$^{41}$, R$^2$ = R$^{B2}$,<br>in L$_{A38}$: R$^1$ = R$^{42}$, R$^2$ = R$^{B2}$,<br>in L$_{A39}$: R$^1$ = R$^{43}$, R$^2$ = R$^{B2}$, and<br>in L$_{A40}$: R$^1$ = R$^{44}$, R$^2$ = R$^{B2}$,, | where<br>in L$_{A41}$: R$^1$ = R$^{41}$, R$^2$ = R$^{B1}$,<br>in L$_{A42}$: R$^1$ = R$^{42}$, R$^2$ = R$^{B1}$,<br>in L$_{A43}$: R$^1$ = R$^{43}$, R$^2$ = R$^{B1}$,<br>in L$_{A44}$: R$^1$ = R$^{44}$, R$^2$ = R$^{B1}$,<br>in L$_{A45}$: R$^1$ = R$^{41}$, R$^2$ = R$^{B2}$,<br>in L$_{A46}$: R$^1$ = R$^{42}$, R$^2$ = R$^{B2}$,<br>in L$_{A47}$: R$^1$ = R$^{43}$, R$^2$ = R$^{B2}$, and<br>in L$_{A48}$: R$^1$ = R$^{44}$, R$^2$ = R$^{B2}$,, |

| L$_{A49}$ through L$_{A56}$, each represented by the formula: | L$_{A57}$ through L$_{A64}$, each represented by the formula: | L$_{A65}$ through L$_{A72}$, each represented by the formula: |
|---|---|---|
| 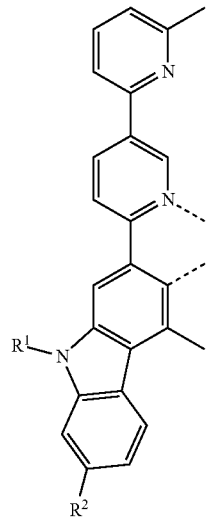 | 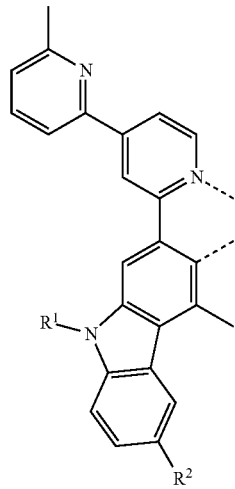 | 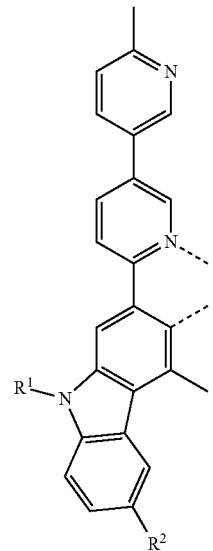 |
| wherein<br>in L$_{A49}$: R$^1$ = R$^{41}$, R$^2$ = R$^{B1}$,<br>in L$_{A50}$: R$^1$ = R$^{42}$, R$^2$ = R$^{B1}$,<br>in L$_{A51}$: R$^1$ = R$^{43}$, R$^2$ = R$^{B1}$,<br>in L$_{A52}$: R$^1$ = R$^{44}$, R$^2$ = R$^{B1}$,<br>in L$_{A53}$: R$^1$ = R$^{41}$, R$^2$ = R$^{B2}$,<br>in L$_{A54}$: R$^1$ = R$^{42}$, R$^2$ = R$^{B2}$,<br>in L$_{A55}$: R$^1$ = R$^{43}$, R$^2$ = R$^{B2}$, and<br>in L$_{A56}$: R$^1$ = R$^{44}$, R$^2$ = R$^{B2}$,, | where<br>in L$_{A57}$: R$^1$ = R$^{41}$, R$^2$ = R$^{B1}$,<br>in L$_{A58}$: R$^1$ = R$^{42}$, R$^2$ = R$^{B1}$,<br>in L$_{A59}$: R$^1$ = R$^{43}$, R$^2$ = R$^{B1}$,<br>in L$_{A60}$: R$^1$ = R$^{44}$, R$^2$ = R$^{B1}$,<br>in L$_{A61}$: R$^1$ = R$^{41}$, R$^2$ = R$^{B2}$,<br>in L$_{A62}$: R$^1$ = R$^{42}$, R$^2$ = R$^{B2}$,<br>in L$_{A63}$: R$^1$ = R$^{43}$, R$^2$ = R$^{B2}$, and<br>in L$_{A64}$: R$^1$ = R$^{44}$, R$^2$ = R$^{B2}$,, | wherein<br>in L$_{A65}$: R$^1$ = R$^{41}$, R$^2$ = R$^{B1}$,<br>in L$_{A66}$: R$^1$ = R$^{42}$, R$^2$ = R$^{B1}$,<br>in L$_{A67}$: R$^1$ = R$^{43}$, R$^2$ = R$^{B1}$,<br>in L$_{A68}$: R$^1$ = R$^{44}$, R$^2$ = R$^{B1}$,<br>in L$_{A69}$: R$^1$ = R$^{41}$, R$^2$ = R$^{B2}$,<br>in L$_{A70}$: R$^1$ = R$^{42}$, R$^2$ = R$^{B2}$,<br>in L$_{A71}$: R$^1$ = R$^{43}$, R$^2$ = R$^{B2}$, and<br>in L$_{A72}$: R$^1$ = R$^{44}$, R$^2$ = R$^{B2}$,, |

-continued

L$_{A73}$ through L$_{A80}$, each represented by the formula:

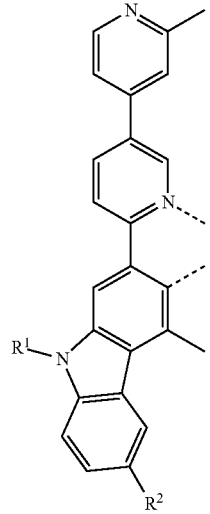

wherein
in L$_{A73}$: R$^1$ = R$^{41}$, R$^2$ = R$^{B1}$,
in L$_{A74}$: R$^1$ = R$^{42}$, R$^2$ = R$^{B1}$,
in L$_{A75}$: R$^1$ = R$^{43}$, R$^2$ = R$^{B1}$,
in L$_{A76}$: R$^1$ = R$^{43}$, R$^2$ = R$^{B1}$,
in L$_{A77}$: R$^1$ = R$^{41}$, R$^2$ = R$^{B2}$,
in L$_{A78}$: R$^1$ = R$^{42}$, R$^2$ = R$^{B2}$,
in L$_{A79}$: R$^1$ = R$^{43}$, R$^2$ = R$^{B2}$, and
in L$_{A80}$: R$^1$ = R$^{44}$, R$^2$ = R$^{B2}$,, L$_{A81}$ through L$_{A88}$, each represented by the formula:

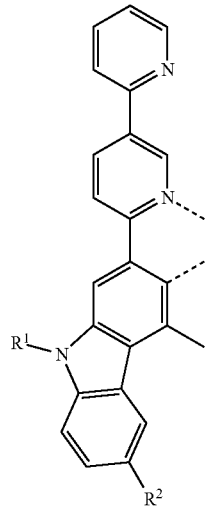

wherein
in L$_{A81}$: R$^1$ = R$^{41}$, R$^2$ = R$^{B1}$,
in L$_{A82}$: R$^1$ = R$^{42}$, R$^2$ = R$^{B1}$,
in L$_{A83}$: R$^1$ = R$^{43}$, R$^2$ = R$^{B1}$,
in L$_{A84}$: R$^1$ = R$^{44}$, R$^2$ = R$^{B1}$,
in L$_{A85}$: R$^1$ = R$^{41}$, R$^2$ = R$^{B2}$,
in L$_{A86}$: R$^1$ = R$^{41}$, R$^2$ = R$^{B2}$,
in L$_{A87}$: R$^1$ = R$^{43}$, R$^2$ = R$^{B2}$, and
in L$_{A88}$: R$^1$ = R$^{44}$, R$^2$ = R$^{B2}$,, L$_{A89}$ through L$_{A96}$, each represented by the formula:

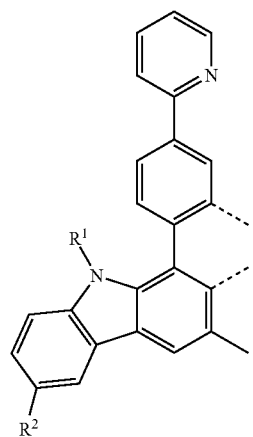

wherein
in L$_{A89}$: R$^1$ = R$^{41}$, R$^2$ = R$^{B1}$,
in L$_{A90}$: R$^1$ = R$^{42}$, R$^2$ = R$^{B1}$,
in L$_{A91}$: R$^1$ = R$^{43}$, R$^2$ = R$^{B1}$,
in L$_{A92}$: R$^1$ = R$^{44}$, R$^2$ = R$^{B1}$,
in L$_{A93}$: R$^1$ = R$^{41}$, R$^2$ = R$^{B2}$,
in L$_{A94}$: R$^1$ = R$^{42}$, R$^2$ = R$^{B2}$,
in L$_{A95}$: R$^1$ = R$^{43}$, R$^2$ = R$^{B2}$, and
in L$_{A96}$: R$^1$ = R$^{44}$, R$^2$ = R$^{B2}$,, L$_{A97}$ through L$_{A100}$, each represented by the formula:

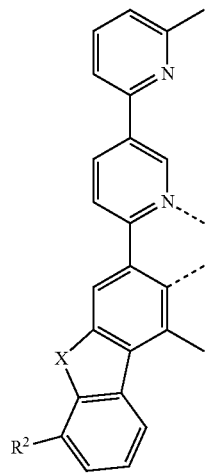

where in L$_{A97}$: X=O, R$^2$ = R$^{B1}$,
in L$_{A98}$: X=O, R$^2$ = R$^{B2}$,
in L$_{A99}$: X=S, R$^2$ = R$^{B1}$, and
in L$_{A100}$: X=S, R$^2$ = R$^{B2}$., -continued L$_{A101}$ through L$_{A104}$, each represented by the formula:

wherein in L$_{A101}$: X=O, R$^2$ = R$^{B1}$,
in L$_{A102}$: X=O, R$^2$ = R$^{B2}$,
in L$_{A103}$: X=S, R$^2$ = R$^{B1}$, and
in L$_{A104}$: X=S, R$^2$ = R$^{B2}$., L$_{A105}$ through L$_{A110}$, each represented by the formula:

wherein in L$_{A105}$: X=O, R$^2$ = R$^{B1}$,
in L$_{A106}$: X=O, R$^2$ = R$^{B2}$,
in L$_{A107}$: X=S, R$^2$ = R$^{B1}$,
in L$_{A108}$: X=S, R$^2$ = R$^{B2}$,
in L$_{A109}$: X=C(CH$_3$)$_2$, R$^2$ = R$^{B1}$, and
in L$_{A110}$: X=C(CH$_3$)$_2$, R$^2$ = R$^{B2}$., L$_{A111}$ through L$_{A116}$, each represented by the formula:

L$_{A117}$ through L$_{A122}$, each represented by the formula:

L$_{A123}$ through L$_{A128}$, each represented by the formula:

wherein in L$_{A111}$: X=O, R$^2$ = R$^{B1}$,
in L$_{A112}$: X=O, R$^2$ = R$^{B2}$,
in L$_{A113}$: X=S, R$^2$ = R$^{B1}$,
in L$_{A114}$: X=S, R$^2$ = R$^{B2}$,
in L$_{A115}$: X=C(CH$_3$)$_2$, R$^2$ = R$^{B1}$, and
in L$_{A116}$: X=C(CH$_3$)$_2$, R$^2$ = R$^{B2}$., wherein in L$_{A117}$: X=O, R$^2$ = R$^{B1}$,
in L$_{A118}$: X=O, R$^2$ = R$^{B2}$,
in L$_{A119}$: X=S, R$^2$ = R$^{B1}$,
in L$_{A120}$: X=S, R$^2$ = R$^{B2}$,
in L$_{A121}$: X=C(CH$_3$)$_2$, R$^2$ = R$^{B1}$, and
in L$_{A122}$: X=C(CH$_3$)$_2$, R$^2$ = R$^{B2}$., wherein in L$_{A123}$: X=O, R$^2$ = R$^{B1}$,
in L$_{A124}$: X=O, R$^2$ = R$^{B2}$,
in L$_{A125}$: X=S, R$^2$ = R$^{B1}$,
in L$_{A126}$: X=S, R$^2$ = R$^{B2}$,
in L$_{A127}$: X=C(CH$_3$)$_2$, R$^2$ = R$^{B1}$, and
in L$_{A128}$: X=C(CH$_3$)$_2$, R$^2$ = R$^{B2}$.,

| $L_{A129}$ through $L_{A134}$, each represented by the formula: | $L_{A135}$ through $L_{A140}$, each represented by the formula: | $L_{A141}$ through $L_{A146}$, each represented by the formula: |
|---|---|---|
| 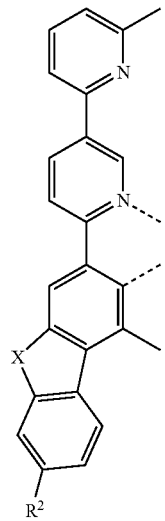 | 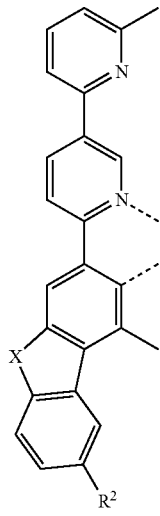 | 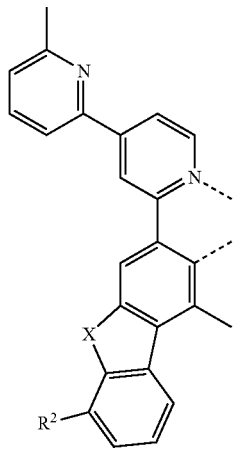 |
| wherein in $L_{A129}$: X=O, $R^2 = R^{B1}$,<br>in $L_{A130}$: X=O, $R^2 = R^{B2}$,<br>in $L_{A131}$: X=S, $R^2 = R^{B1}$,<br>in $L_{A132}$: X=S, $R^2 = R^{B2}$,<br>in $L_{A133}$: X=C(CH$_3$)$_2$, $R^2 = R^{B1}$, and<br>in $L_{A134}$: X=C(CH$_3$)$_2$, $R^2 = R^{B2}$., | wherein in $L_{A135}$: X=O, $R^2 = R^{B1}$,<br>in $L_{A136}$: X=O, $R^2 = R^{B2}$,<br>in $L_{A137}$: X=S, $R^2 = R^{B1}$,<br>in $L_{A138}$: X=S, $R^2 = R^{B2}$,<br>in $L_{A139}$: X=C(CH$_3$)$_2$, $R^2 = R^{B1}$, and<br>in $L_{A140}$: X=C(CH$_3$)$_2$, $R^2 = R^{B2}$., | wherein in $L_{A141}$: X=O, $R^2 = R^{B1}$,<br>in $L_{A142}$: X=O, $R^2 = R^{B2}$,<br>in $L_{A143}$: X=S, $R^2 = R^{B1}$,<br>in $L_{A144}$: X=S, $R^2 = R^{B2}$,<br>in $L_{A145}$: X=C(CH$_3$)$_2$, $R^2 = R^{B1}$, and<br>$L_{A146}$: X=C(CH$_3$)$_2$, $R^2 = R^{B2}$., |
| $L_{A147}$ through $L_{A152}$, each represented by the formula: | $L_{A153}$ through $L_{A158}$, each represented by the formula: | $L_{A159}$ through $L_{A164}$, each represented by the formula: |
| 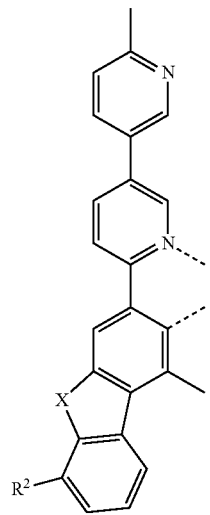 | 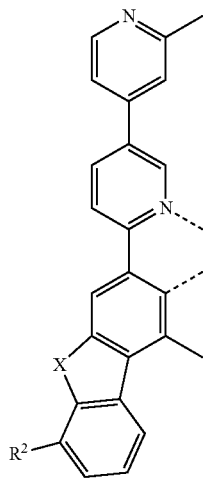 | 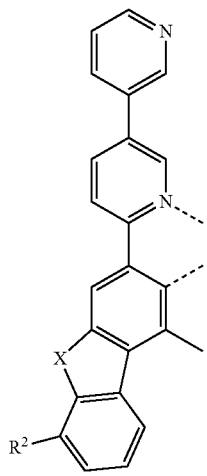 |
| wherein in $L_{A147}$: $R^1 = R^{A1}$, $R^2 = R^{B1}$,<br>in $L_{A148}$: $R^1 = R^{A2}$, $R^2 = R^{B1}$,<br>in $L_{A149}$ $R^1 = R^{A1}$, $R^2 = R^{B2}$,<br>in $L_{A150}$: $R^1 = R^{A2}$, $R^2 = R^{B2}$,<br>in $L_{A151}$: X=C(CH$_3$)$_2$, $R^2 = R^{B1}$, and<br>in $L_{A152}$: X=C(CH$_3$)$_2$, $R^2 = R^{B2}$., | wherein in $L_{A153}$: $R^1 = R^{A1}$, $R^2 = R^{B1}$,<br>in $L_{A154}$: $R^1 = R^{A2}$, $R^2 = R^{B1}$,<br>in $L_{A155}$: $R^1 = R^{A1}$, $R^2 = R^{B2}$,<br>in $L_{A156}$: $R^1 = R^{A2}$, $R^2 = R^{B2}$,<br>in $L_{A157}$: X=C(CH$_3$)$_2$, $R^2 = R^{B1}$, and<br>in $L_{A158}$: X=C(CH$_3$)$_2$, $R^2 = R^{B2}$., | wherein in $L_{A159}$: X=O, $R^2 = R^{B1}$,<br>in $L_{A160}$: X=O, $R^2 = R^{B2}$,<br>in $L_{A161}$: X=S, $R^2 = R^{B1}$,<br>in $L_{A162}$: X=S, $R^2 = R^{B2}$,<br>in $L_{A163}$: X=C(CH$_3$)$_2$, $R^2 = R^{B1}$, and<br>in $L_{A164}$: X=C(CH$_3$)$_2$, $R^2 = R^{B2}$., |

| $L_{A165}$ through $L_{A170}$, each represented by the formula: | $L_{A171}$ through $L_{A176}$, each represented by the formula: |
|---|---|
| 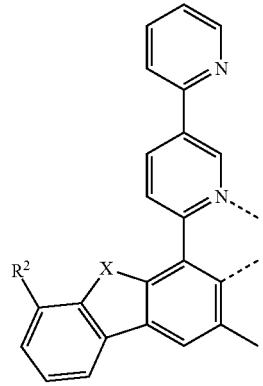 | 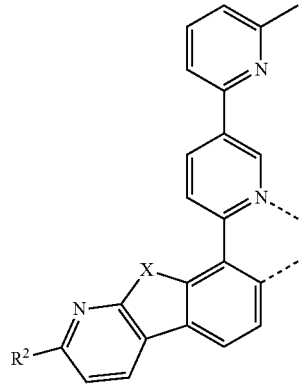 |
| wherein in $L_{A165}$: X=O, $R^2 = R^{B1}$,<br>in $L_{A166}$: X=O, $R^2 = R^{B2}$,<br>in $L_{A167}$: X=S, $R^2 = R^{B1}$,<br>in $L_{A168}$: X=S, $R^2 = R^{B2}$,<br>in $L_{A169}$: X=C(CH$_3$)$_2$, $R^2 = R^{B1}$, and<br>in $L_{A170}$: X=C(CH$_3$)$_2$, $R^2 = R^{B2}$., | wherein in $L_{A171}$: X=O, $R^2 = R^{B1}$,<br>in $L_{A172}$: X=O, $R^2 = R^{B2}$,<br>in $L_{A173}$: X=S, $R^2 = R^{B1}$,<br>in $L_{A174}$: X=S, $R^2 = R^{B2}$,<br>$L_{A175}$: X=C(CH$_3$)$_2$, $R^2 = R^{B1}$, and<br>$L_{A176}$: X=C(CH$_3$)$_2$, $R^2 = R^{B2}$., and |

$L_{A177}$ through $L_{A182}$, each represented by the formula:

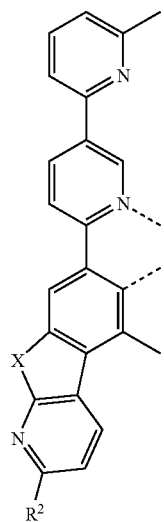

wherein in $L_{A177}$: X=O, $R^2 = R^{B1}$,
in $L_{A178}$: X=O, $R^2 = R^{B2}$,
in $L_{A179}$: X=S, $R^2 = R^{B1}$,
in $L_{A180}$: X=S, $R^2 = R^{B2}$,
in $L_{A181}$: X=C(CH$_3$)$_2$, $R^2 = R^{B1}$, and
in $L_{A182}$: X=C(CH$_3$)$_2$, $R^2 = R^{B2}$..

In the structures of $L_{A1}$ through $L_{A182}$, $R^{A1}$ to $R^{A4}$ have the
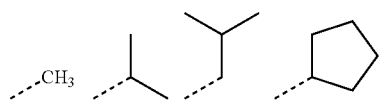
following structures: $R^{A1}$, $R^{A2}$, $R^{A3}$, and $R^{A4}$, and $R^{B1}$ and $R^{B2}$ have the following
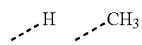
structures: $R^{B1}$, and $R^{B2}$.
In some embodiments, $L_B$ is selected from the group consisting of:
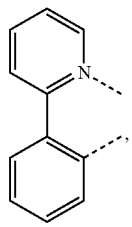
$L_{B1}$
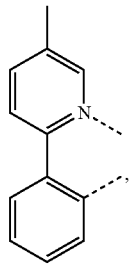
$L_{B2}$
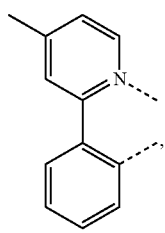
$L_{B3}$
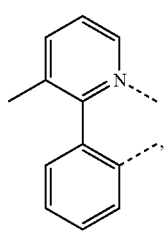
$L_{B4}$
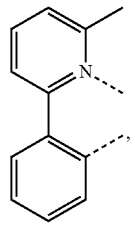
$L_{B5}$
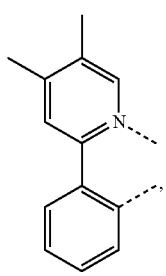
$L_{B6}$
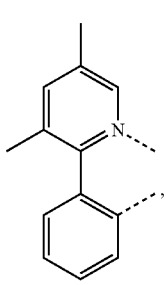
$L_{B7}$
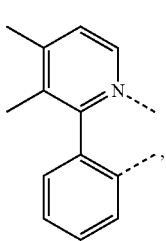
$L_{B8}$
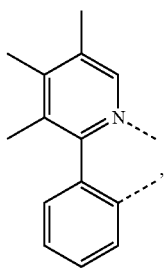
$L_{B9}$
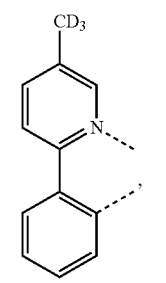
$L_{B10}$

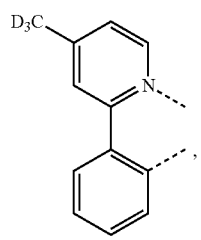 L_{B11}
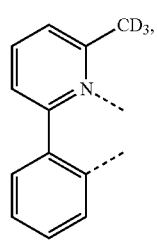 L_{B12}
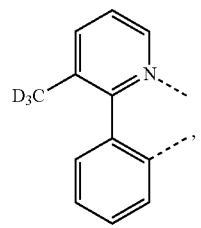 L_{B13}
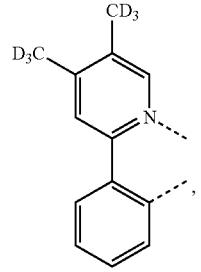 L_{B14}
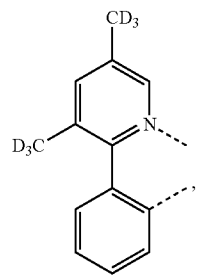 L_{B15}
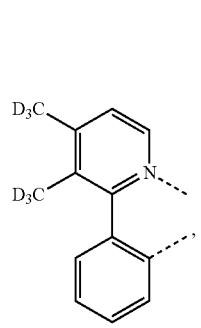 L_{B16}
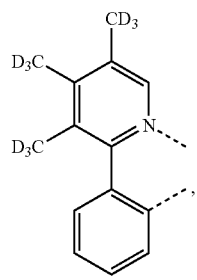 L_{B17}
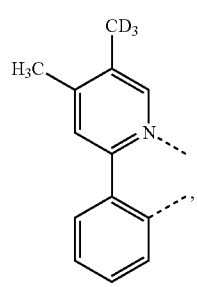 L_{B18}
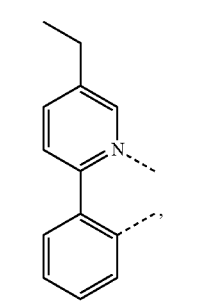 L_{B19}
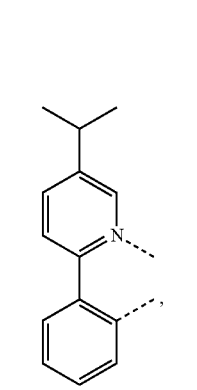 L_{B20}
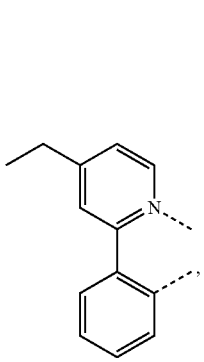 L_{B21}

L_{B22}
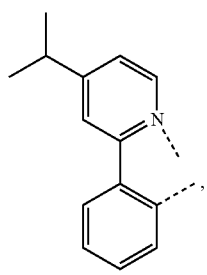
L_{B23}
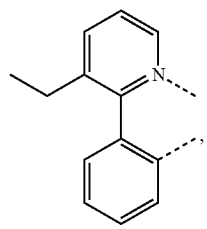
L_{B24}
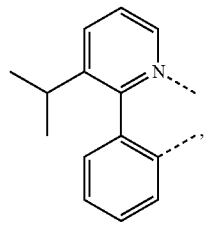
L_{B25}
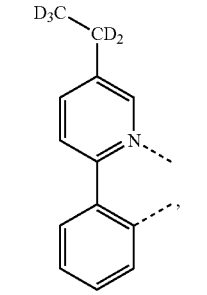
L_{B26}
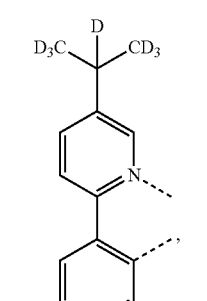
L_{B27}
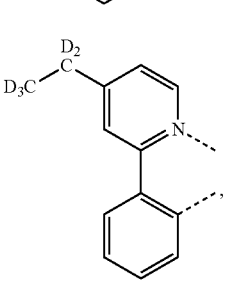
L_{B28}
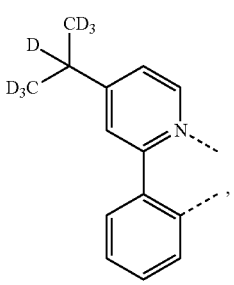
L_{B30}
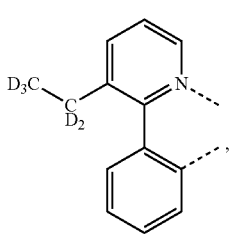
L_{B31}
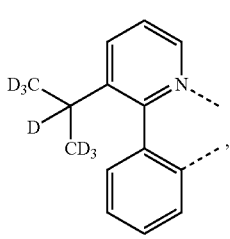
L_{B32}
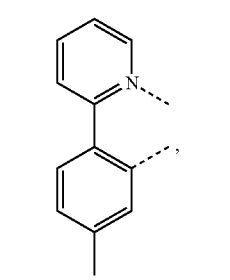
L_{B33}
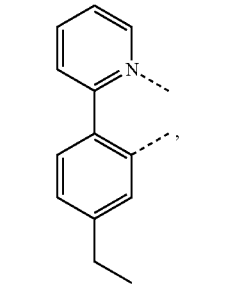
L_{B34}
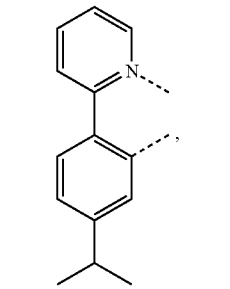

$L_{B35}$ 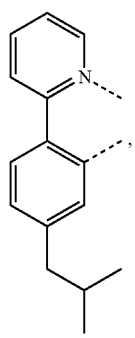
$L_{B36}$ 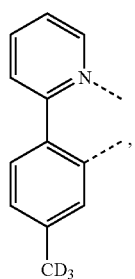
$L_{B37}$ 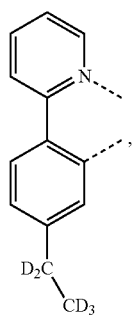
$L_{B38}$ 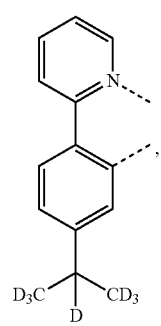
$L_{B39}$ 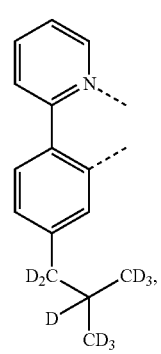
$L_{B40}$ 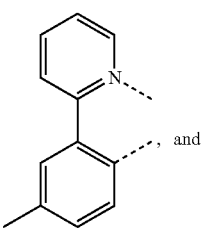, and
$L_{B41}$ 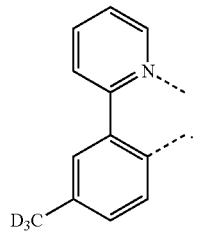
In some embodiments, $L_C$ is selected from the group consisting of:
$L_{C1}$ 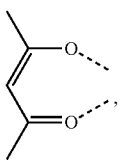
$L_{C2}$ 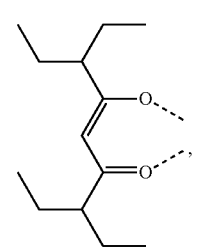
$L_{C3}$ 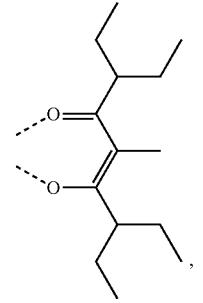
$L_{C4}$ 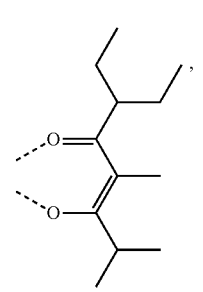

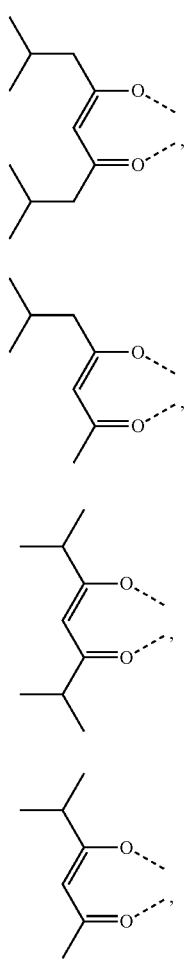

$L_{C5}$ $L_{C6}$ $L_{C7}$ $L_{C8}$

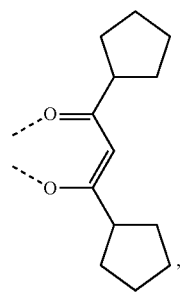

$L_{C9}$

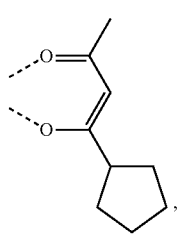

$L_{C10}$

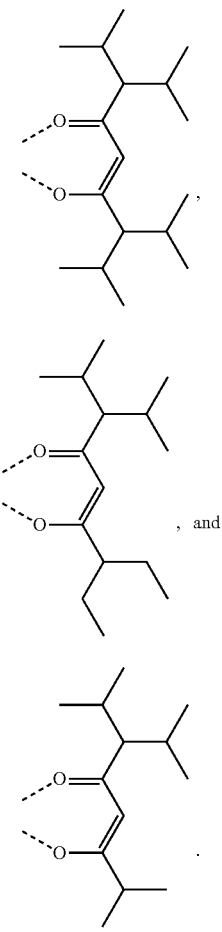

$L_{C11}$ $L_{C12}$, and $L_{C13}$

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

In one embodiment of the compound, at least one $R^4$ in the ligand $L_A$ is a six-membered aromatic heterocyclic ring, such as a substituted triazine moiety, having at least two nitrogen atoms where the only heteroatom is nitrogen. The substitution can be at different positions of the triazine and the side chains on the triazine can also be modified. This embodiment will be hereinafter referred to as the "Triazine" embodiment. The triazine unit is a well-known electron deficient building block and it should lower the LUMO energy level which will help make the compound function as a red emitter in an OLED.

The present disclosure encompasses the following further embodiments. The Triazine embodiment, wherein M is selected from the group consisting of Ir, Rh, Re, Ru, Os, Pt, Au, and Cu. A Triazine embodiment wherein M is Ir. The Triazine embodiment wherein the compound has the formula $M(L_A)_2(L_C)$. The Triazine embodiment wherein the compound has the formula $M(L_A)(L_B)_2$. $A^1$, $A^2$, $A^3$, $A^4$, $A^5$, $A^6$, $A^7$, and $A^8$ are carbon. The Triazine embodiment wherein exactly one of $A^1$, $A^2$, $A^3$, $A^4$, $A^5$, $A^6$, $A^7$, and $A^8$ is nitrogen. The Triazine embodiment wherein exactly one of $A^5$, $A^6$, $A^7$, and $A^8$ is nitrogen, while $A^1$, $A^2$, $A^3$, and $A^4$ are carbon. The Triazine embodiment wherein X is O. The Triazine embodiment wherein X is NR¹. The Triazine embodiment wherein at least one R⁴ is a six-membered aromatic heterocyclic ring having two nitrogen atoms. The Triazine embodiment wherein at least one R⁴ is a six-membered aromatic heterocyclic ring having three nitrogen atoms. The Triazine embodiment wherein at least one R⁴ is selected from the group consisting of triazine, pyrazine, pyrimidine, and pyridazine. The Triazine embodiment wherein $L_c$ has the formula:

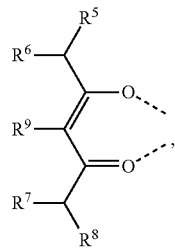

wherein R⁵, R⁶, R⁷, and R⁸ are independently selected from group consisting of alkyl, cycloalkyl, aryl, and heteroaryl, wherein at least one of R⁵, R⁶, R⁷, and R⁸ has at least two C atoms. The Triazine embodiment wherein each of R, R', R¹, R², R³, R⁴, $R^C$, $R^D$, $R^X$, $R^Y$, $R^Z$ and $R^E$ is independently selected from group consisting of hydrogen, deuterium, alkyl, cycloalkyl, and combinations thereof. The Triazine embodiment wherein R⁹ is hydrogen. The Triazine embodiment wherein each of R, R', R¹, R², R³, R⁴, $R^C$, $R^D$, $R^X$, $R^Y$, $R^Z$ and $R^E$ is independently selected from the group consisting of hydrogen, deuterium, methyl, ethyl, propyl, 1-methylethyl, butyl, 1-methylpropyl, 2-methylpropyl, pentyl, 1-methylbutyl, 2-methylbutyl, 3-methylbutyl, 1,1-dimethylpropyl, 1,2-dimethylpropyl, 2,2-dimethylpropyl, cyclobutyl, cyclopentyl, cyclohexyl, and combinations thereof. The Triazine embodiment wherein ring C is benzene, and ring D is pyridine. The Triazine embodiment wherein $L_A$ is selected from the group consisting of:

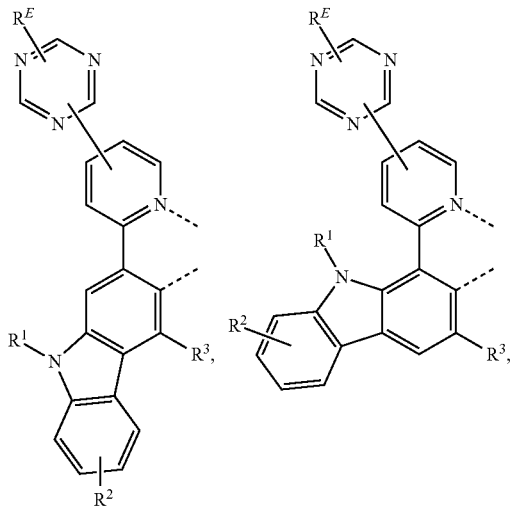

-continued

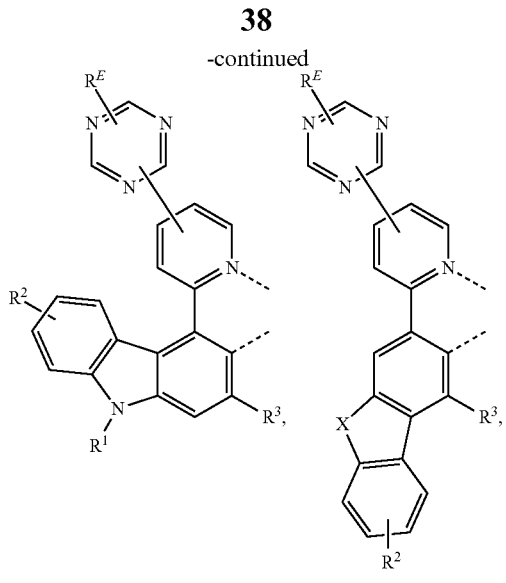

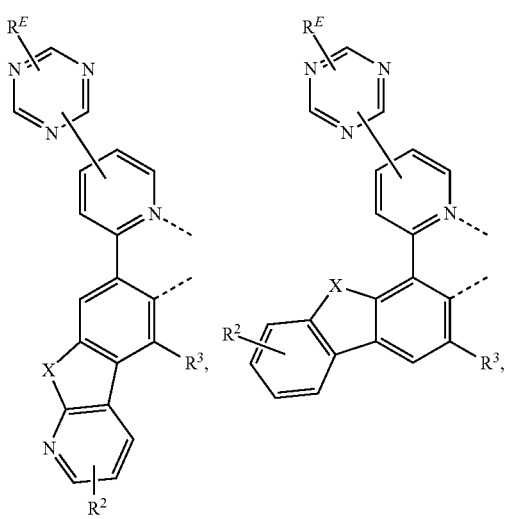

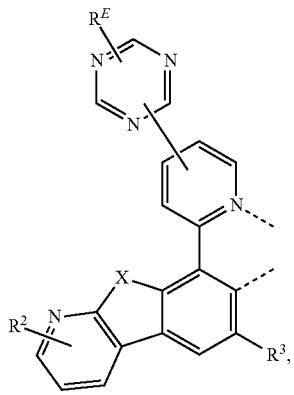

-continued

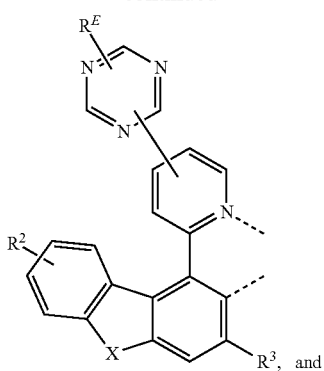

and

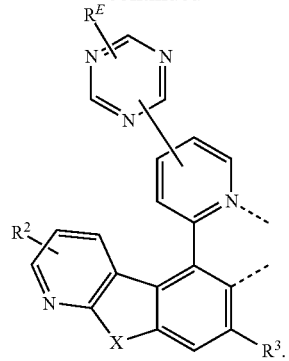

The Triazine embodiment wherein $L_A$ is selected from the group consisting of:

| $L_{A183}$ through $L_{A198}$, each represented by the formula: | $L_{A199}$ through $L_{A214}$, each represented by the formula: |
|---|---|

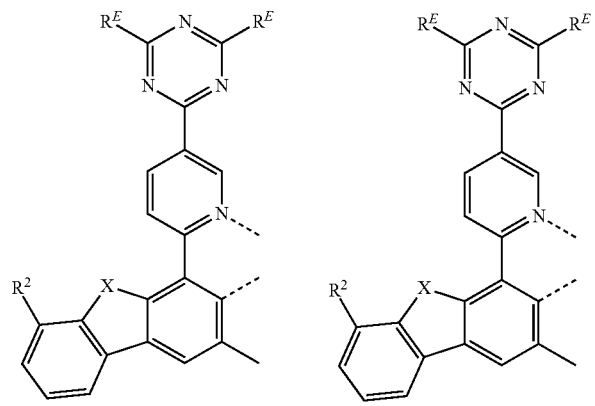

wherein
in $L_{A183}$: X=O, $R^E = R^{A5}$, $R^2 = R^{B1}$,
in $L_{A184}$: X=O, $R^E = R^{A5}$, $R^2 = R^{B2}$,
in $L_{A185}$: X=O, $R^E = R^{A6}$, $R^2 = R^{B1}$,
in $L_{A186}$: X=O, $R^E = R^{A6}$, $R^2 = R^{B2}$,
in $L_{A187}$: X=O, $R^E = R^{A7}$, $R^2 = R^{B1}$,
in $L_{A188}$: X=O, $R^E = R^{A7}$, $R^2 = R^{B2}$,
in $L_{A189}$: X=O, $R^E = R^{A8}$, $R^2 = R^{B1}$,
in $L_{A190}$: X=O, $R^E = R^{A8}$, $R^2 = R^{B2}$,
in $L_{A191}$: X=S, $R^E = R^{A5}$, $R^2 = R^{B1}$,
in $L_{A192}$: X=S, $R^E = R^{A5}$, $R^2 = R^{B2}$,
in $L_{A193}$: X=S, $R^E = R^{A6}$, $R^2 = R^{B1}$,
in $L_{A194}$: X=S, $R^E = R^{A6}$, $R^2 = R^{B2}$,
in $L_{A195}$: X=S, $R^E = R^{A7}$, $R^2 = R^{B1}$,
in $L_{A196}$: X=S, $R^E = R^{A7}$, $R^2 = R^{B2}$,
in $L_{A197}$: X=S, $R^E = R^{A8}$, $R^2 = R^{B1}$, and
in $L_{A198}$: X=S, $R^E = R^{A8}$, $R^2 = R^{B2}$., wherein
in $L_{A199}$: X=O, $R^E = R^{A5}$, $R^2 = R^{B1}$,
in $L_{A200}$: X=O, $R^E = R^{A5}$, $R^2 = R^{B2}$,
in $L_{A201}$: X=O, $R^E = R^{A6}$, $R^2 = R^{B1}$,
in $L_{A202}$: X=O, $R^E = R^{A6}$, $R^2 = R^{B2}$,
in $L_{A203}$: X=O, $R^E = R^{A7}$, $R^2 = R^{B1}$,
in $L_{A204}$: X=O, $R^E = R^{A7}$, $R^2 = R^{B2}$,
in $L_{A205}$: X=O, $R^E = R^{A8}$, $R^2 = R^{B1}$,
in $L_{A206}$: X=O, $R^E = R^{A8}$, $R^2 = R^{B2}$,
in $L_{A207}$: X=S, $R^E = R^{A5}$, $R^2 = R^{B1}$,
in $L_{A208}$: X=S, $R^E = R^{A5}$, $R^2 = R^{B2}$,
in $L_{A209}$: X=S, $R^E = R^{A6}$, $R^2 = R^{B1}$,
in $L_{A210}$: X=S, $R^E = R^{A6}$, $R^2 = R^{B2}$,
in $L_{A211}$: X=S, $R^E = R^{A7}$, $R^2 = R^{B1}$,
in $L_{A212}$: X=S, $R^E = R^{A7}$, $R^2 = R^{B2}$,
in $L_{A213}$: X=S, $R^E = R^{A8}$, $R^2 = R^{B1}$, and
in $L_{A214}$: X=S, $R^E = R^{A8}$, $R^2 = R^{B2}$.,

| $L_{A215}$ through $L_{A230}$, each represented by the formula: | $L_{A231}$ through $L_{A246}$, each represented by the formula: |
|---|---|
| 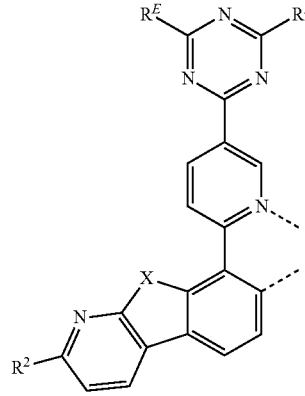 | 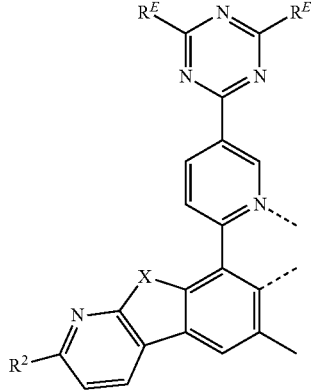 | wherein
in $L_{A215}$: X=O, $R^E = R^{45}$, $R^2 = R^{B1}$,
in $L_{A216}$: X=O, $R^E = R^{45}$, $R^2 = R^{B2}$,
in $L_{A217}$: X=O, $R^E = R^{46}$, $R^2 = R^{B1}$,
in $L_{A218}$: X=O, $R^E = R^{46}$, $R^2 = R^{B2}$,
in $L_{A219}$: X=O, $R^E = R^{47}$, $R^2 = R^{B1}$,
in $L_{A220}$: X=O, $R^E = R^{47}$, $R^2 = R^{B2}$,
in $L_{A221}$: X=O, $R^E = R^{48}$, $R^2 = R^{B1}$,
in $L_{A222}$: X=O, $R^E = R^{48}$, $R^2 = R^{B2}$,
in $L_{A223}$: X=S, $R^E = R^{45}$, $R^2 = R^{B1}$,
in $L_{A224}$: X=S, $R^E = R^{45}$, $R^2 = R^{B2}$,
in $L_{A225}$: X=S, $R^E = R^{46}$, $R^2 = R^{B1}$,
in $L_{A226}$: X=S, $R^E = R^{46}$, $R^2 = R^{B2}$,
in $L_{A227}$: X=S, $R^E = R^{47}$, $R^2 = R^{B1}$,
in $L_{A228}$: X=S, $R^E = R^{47}$, $R^2 = R^{B2}$,
in $L_{A229}$: X=S, $R^E = R^{48}$, $R^2 = R^{B1}$, and
in $L_{A230}$: X=S, $R^E = R^{48}$, $R^2 = R^{B2}$., wherein
in $L_{A231}$: X=O, $R^E = R^{45}$, $R^2 = R^{B1}$,
in $L_{A232}$: X=O, $R^E = R^{45}$, $R^2 = R^{B2}$,
in $L_{A233}$: X=O, $R^E = R^{46}$, $R^2 = R^{B1}$,
in $L_{A234}$: X=O, $R^E = R^{46}$, $R^2 = R^{B2}$,
in $L_{A235}$: X=O, $R^E = R^{47}$, $R^2 = R^{B1}$,
in $L_{A236}$: X=O, $R^E = R^{47}$, $R^2 = R^{B2}$,
in $L_{A237}$: X=O, $R^E = R^{48}$, $R^2 = R^{B1}$,
in $L_{A238}$: X=O, $R^E = R^{48}$, $R^2 = R^{B2}$,
in $L_{A239}$: X=S, $R^E = R^{45}$, $R^2 = R^{B1}$,
in $L_{A240}$: X=S, $R^E = R^{45}$, $R^2 = R^{B2}$,
in $L_{A241}$: X=S, $R^E = R^{46}$, $R^2 = R^{B1}$,
in $L_{A242}$: X=S, $R^E = R^{46}$, $R^2 = R^{B2}$,
in $L_{A243}$: X=S, $R^E = R^{47}$, $R^2 = R^{B1}$,
in $L_{A244}$: X=S, $R^E = R^{47}$, $R^2 = R^{B2}$,
in $L_{A245}$: X=S, $R^E = R^{48}$, $R^2 = R^{B1}$, and
in $L_{A246}$: X=S, $R^E = R^{48}$, $R^2 = R^{B2}$.,

| $L_{A247}$ through $L_{A262}$, each represented by the formula: | $L_{A263}$ through $L_{A278}$, each represented by the formula: |
|---|---|
| 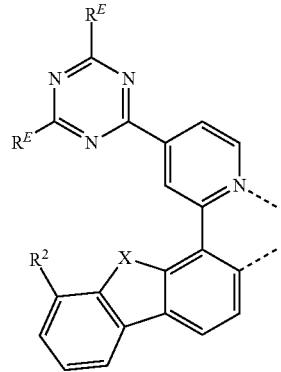 | 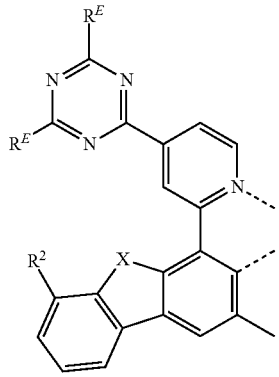 | wherein
in $L_{A247}$: X=O, $R^E = R^{45}$, $R^2 = R^{B1}$,
in $L_{A248}$: X=O, $R^E = R^{45}$, $R^2 = R^{B2}$,
in $L_{A249}$: X=O, $R^E = R^{46}$, $R^2 = R^{B1}$,
in $L_{A250}$: X=O, $R^E = R^{46}$, $R^2 = R^{B2}$,
in $L_{A251}$: X=O, $R^E = R^{47}$, $R^2 = R^{B1}$,
in $L_{A252}$: X=O, $R^E = R^{47}$, $R^2 = R^{B2}$,
in $L_{A253}$: X=O, $R^E = R^{48}$, $R^2 = R^{B1}$,
in $L_{A254}$: X=O, $R^E = R^{48}$, $R^2 = R^{B2}$,
in $L_{A255}$: X=S, $R^E = R^{45}$, $R^2 = R^{B1}$,
in $L_{A256}$: X=S, $R^E = R^{45}$, $R^2 = R^{B2}$,
in $L_{A257}$: X=S, $R^E = R^{46}$, $R^2 = R^{B1}$,
in $L_{A258}$: X=S, $R^E = R^{46}$, $R^2 = R^{B2}$,
in $L_{A259}$: X=S, $R^E = R^{47}$, $R^2 = R^{B1}$,
in $L_{A260}$: X=S, $R^E = R^{47}$, $R^2 = R^{B2}$,
in $L_{A261}$: X=S, $R^E = R^{48}$, $R^2 = R^{B1}$, and
in $L_{A262}$: X=S, $R^E = R^{48}$, $R^2 = R^{B2}$., wherein
in $L_{A263}$: X=O, $R^E = R^{45}$, $R^2 = R^{B1}$,
in $L_{A264}$: X=O, $R^E = R^{45}$, $R^2 = R^{B2}$,
in $L_{A265}$: X=O, $R^E = R^{46}$, $R^2 = R^{B1}$,
in $L_{A266}$: X=O, $R^E = R^{46}$, $R^2 = R^{B2}$,
in $L_{A267}$: X=O, $R^E = R^{47}$, $R^2 = R^{B1}$,
in $L_{A268}$: X=O, $R^E = R^{47}$, $R^2 = R^{B2}$,
in $L_{A269}$: X=O, $R^E = R^{48}$, $R^2 = R^{B1}$,
in $L_{A270}$: X=O, $R^E = R^{48}$, $R^2 = R^{B2}$,
in $L_{A271}$: X=S, $R^E = R^{45}$, $R^2 = R^{B1}$,
in $L_{A272}$: X=S, $R^E = R^{45}$, $R^2 = R^{B2}$,
in $L_{A273}$: X=S, $R^E = R^{46}$, $R^2 = R^{B1}$,
in $L_{A274}$: X=S, $R^E = R^{46}$, $R^2 = R^{B2}$,
in $L_{A275}$: X=S, $R^E = R^{47}$, $R^2 = R^{B1}$,
in $L_{A276}$: X=S, $R^E = R^{47}$, $R^2 = R^{B2}$,
in $L_{A277}$: X=S, $R^E = R^{48}$, $R^2 = R^{B1}$, and
in $L_{A278}$: X=S, $R^E = R^{48}$, $R^2 = R^{B2}$., -continued

| $L_{A279}$ through $L_{A294}$, each represented by the formula: | $L_{A295}$ through $L_{A310}$, each represented by the formula: |
|---|---|
| 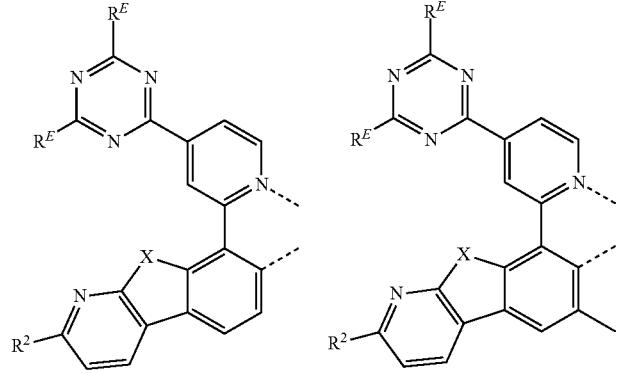 | | wherein
in $L_{A279}$: X=O, $R^E = R^{A5}$, $R^2 = R^{B1}$,
in $L_{A280}$: X=O, $R^E = R^{A5}$, $R^2 = R^{B2}$,
in $L_{A281}$: X=O, $R^E = R^{A6}$, $R^2 = R^{B1}$,
in $L_{A282}$: X=O, $R^E = R^{A6}$, $R^2 = R^{B2}$,
in $L_{A283}$: X=O, $R^E = R^{A7}$, $R^2 = R^{B1}$,
in $L_{A284}$: X=O, $R^E = R^{A7}$, $R^2 = R^{B2}$,
in $L_{A285}$: X=O, $R^E = R^{A8}$, $R^2 = R^{B1}$,
in $L_{A286}$: X=O, $R^E = R^{A8}$, $R^2 = R^{B2}$,
in $L_{A287}$: X=S, $R^E = R^{A5}$, $R^2 = R^{B1}$,
in $L_{A288}$: X=S, $R^E = R^{A5}$, $R^2 = R^{B2}$,
in $L_{A289}$: X=S, $R^E = R^{A6}$, $R^2 = R^{B1}$,
in $L_{A290}$: X=S, $R^E = R^{A6}$, $R^2 = R^{B2}$,
in $L_{A291}$: X=S, $R^E = R^{A7}$, $R^2 = R^{B1}$,
in $L_{A292}$: X=S, $R^E = R^{A7}$, $R^2 = R^{B2}$,
in $L_{A293}$: X=S, $R^E = R^{A8}$, $R^2 = R^{B1}$, and
in $L_{A294}$: X=S, $R^E = R^{A8}$, $R^2 = R^{B2}$., wherein
in $L_{A295}$: X=O, $R^E = R^{A5}$, $R^2 = R^{B1}$,
in $L_{A296}$: X=O, $R^E = R^{A5}$, $R^2 = R^{B2}$,
in $L_{A297}$: X=O, $R^E = R^{A6}$, $R^2 = R^{B1}$,
in $L_{A298}$: X=O, $R^E = R^{A6}$, $R^2 = R^{B2}$,
in $L_{A299}$: X=O, $R^E = R^{A7}$, $R^2 = R^{B1}$,
in $L_{A300}$: X=O, $R^E = R^{A7}$, $R^2 = R^{B2}$,
in $L_{A301}$: X=O, $R^E = R^{A8}$, $R^2 = R^{B1}$,
in $L_{A302}$: X=O, $R^E = R^{A8}$, $R^2 = R^{B2}$,
in $L_{A303}$: X=S, $R^E = R^{A5}$, $R^2 = R^{B1}$,
in $L_{A304}$: X=S, $R^E = R^{A5}$, $R^2 = R^{B2}$,
in $L_{A305}$: X=S, $R^E = R^{A6}$, $R^2 = R^{B1}$,
in $L_{A306}$: X=S, $R^E = R^{A6}$, $R^2 = R^{B2}$,
in $L_{A307}$: X=S, $R^E = R^{A7}$, $R^2 = R^{B1}$,
in $L_{A308}$: X=S, $R^E = R^{A7}$, $R^2 = R^{B2}$,
in $L_{A309}$: X=S, $R^E = R^{A8}$, $R^2 = R^{B1}$, and
in $L_{A310}$: X=S, $R^E = R^{A8}$, $R^2 = R^{B2}$.,

| $L_{A311}$ through $L_{A326}$, each represented by the formula: | $L_{A327}$ through $L_{A342}$, each represented by the formula: |
|---|---|
| 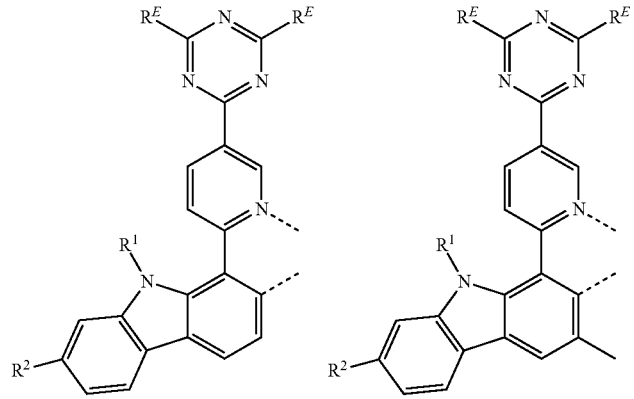 | | wherein
in $L_{A311}$: $R^E = R^{A5}$, $R^2 = R^{B1}$, $R^1 = R^{C1}$,
in $L_{A312}$: $R^E = R^{A5}$, $R^2 = R^{B2}$, $R^1 = R^{C1}$,
in $L_{A313}$: $R^E = R^{A6}$, $R^2 = R^{B1}$, $R^1 = R^{C1}$,
in $L_{A314}$: $R^E = R^{A6}$, $R^2 = R^{B2}$, $R^1 = R^{C1}$,
in $L_{A315}$: $R^E = R^{A7}$, $R^2 = R^{B1}$, $R^1 = R^{C1}$,
in $L_{A316}$: $R^E = R^{A7}$, $R^2 = R^{B2}$, $R^1 = R^{C1}$,
in $L_{A317}$: $R^E = R^{A8}$, $R^2 = R^{B1}$, $R^1 = R^{C1}$,
in $L_{A318}$: $R^E = R^{A8}$, $R^2 = R^{B2}$, $R^1 = R^{C1}$,
in $L_{A319}$: $R^E = R^{A5}$, $R^2 = R^{B1}$, $R^1 = R^{C2}$,
in $L_{A320}$: $R^E = R^{A5}$, $R^2 = R^{B2}$, $R^1 = R^{C2}$,
in $L_{A321}$: $R^E = R^{A6}$, $R^2 = R^{B1}$, $R^1 = R^{C2}$,
in $L_{A322}$: $R^E = R^{A6}$, $R^2 = R^{B2}$, $R^1 = R^{C2}$,
in $L_{A323}$: $R^E = R^{A7}$, $R^2 = R^{B1}$, $R^1 = R^{C2}$,
in $L_{A324}$: $R^E = R^{A7}$, $R^2 = R^{B2}$, $R^1 = R^{C2}$,
in $L_{A325}$: $R^E = R^{A8}$, $R^2 = R^{B1}$, $R^1 = R^{C2}$, and
in $L_{A326}$: $R^E = R^{A8}$, $R^2 = R^{B2}$, $R^1 = R^{C2}$., wherein
in $L_{A327}$: $R^E = R^{A5}$, $R^2 = R^{B1}$, $R^1 = R^{C1}$,
in $L_{A328}$: $R^E = R^{A5}$, $R^2 = R^{B2}$, $R^1 = R^{C1}$,
in $L_{A329}$: $R^E = R^{A6}$, $R^2 = R^{B1}$, $R^1 = R^{C1}$,
in $L_{A330}$: $R^E = R^{A6}$, $R^2 = R^{B2}$, $R^1 = R^{C1}$,
in $L_{A331}$: $R^E = R^{A7}$, $R^2 = R^{B1}$, $R^1 = R^{C1}$,
in $L_{A332}$: $R^E = R^{A7}$, $R^2 = R^{B2}$, $R^1 = R^{C1}$,
in $L_{A333}$: $R^E = R^{A8}$, $R^2 = R^{B1}$, $R^1 = R^{C1}$,
in $L_{A334}$: $R^E = R^{A8}$, $R^2 = R^{B2}$, $R^1 = R^{C1}$,
in $L_{A335}$: $R^E = R^{A5}$, $R^2 = R^{B1}$, $R^1 = R^{C2}$,
in $L_{A336}$: $R^E = R^{A5}$, $R^2 = R^{B2}$, $R^1 = R^{C2}$,
in $L_{A337}$: $R^E = R^{A6}$, $R^2 = R^{B1}$, $R^1 = R^{C2}$,
in $L_{A338}$: $R^E = R^{A6}$, $R^2 = R^{B2}$, $R^1 = R^{C2}$,
in $L_{A339}$: $R^E = R^{A7}$, $R^2 = R^{B1}$, $R^1 = R^{C2}$,
in $L_{A340}$: $R^E = R^{A7}$, $R^2 = R^{B2}$, $R^1 = R^{C2}$,
in $L_{A341}$: $R^E = R^{A8}$, $R^2 = R^{B1}$, $R^1 = R^{C2}$, and
in $L_{A342}$: $R^E = R^{A8}$, $R^2 = R^{B2}$, $R^1 = R^{C2}$., -continued

| $L_{A343}$ through $L_{A358}$, each represented by the formula: | $L_{A359}$ through $L_{A374}$, each represented by the formula: |
|---|---|
| 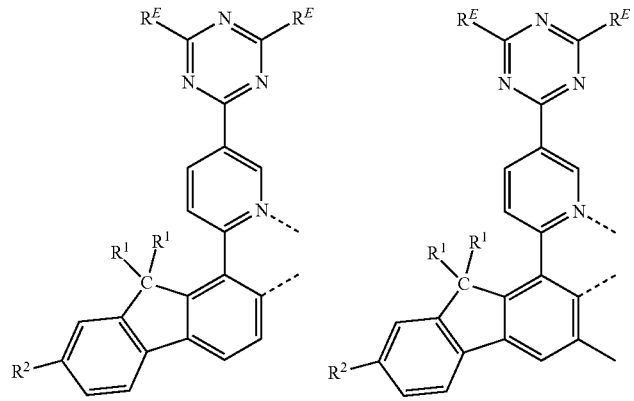 | | wherein
in $L_{A343}$: $R^E = R^{A5}$, $R^2 = R^{B1}$, $R^1 = R^{C1}$,
in $L_{A344}$: $R^E = R^{A5}$, $R^2 = R^{B2}$, $R^1 = R^{C1}$,
in $L_{A345}$: $R^E = R^{A6}$, $R^2 = R^{B1}$, $R^1 = R^{C1}$,
in $L_{A346}$: $R^E = R^{A6}$, $R^2 = R^{B2}$, $R^1 = R^{C1}$,
in $L_{A347}$: $R^E = R^{A7}$, $R^2 = R^{B1}$, $R^1 = R^{C1}$,
in $L_{A348}$: $R^E = R^{A7}$, $R^2 = R^{B2}$, $R^1 = R^{C1}$,
in $L_{A349}$: $R^E = R^{A8}$, $R^2 = R^{B1}$, $R^1 = R^{C1}$,
in $L_{A350}$: $R^E = R^{A8}$, $R^2 = R^{B2}$, $R^1 = R^{C1}$,
in $L_{A351}$: $R^E = R^{A5}$, $R^2 = R^{B1}$, $R^1 = R^{C2}$,
in $L_{A352}$: $R^E = R^{A5}$, $R^2 = R^{B2}$, $R^1 = R^{C2}$,
in $L_{A353}$: $R^E = R^{A6}$, $R^2 = R^{B1}$, $R^1 = R^{C2}$,
in $L_{A354}$: $R^E = R^{A6}$, $R^2 = R^{B2}$, $R^1 = R^{C2}$,
in $L_{A355}$: $R^E = R^{A7}$, $R^2 = R^{B1}$, $R^1 = R^{C2}$,
in $L_{A356}$: $R^E = R^{A7}$, $R^2 = R^{B2}$, $R^1 = R^{C2}$,
in $L_{A357}$: $R^E = R^{A8}$, $R^2 = R^{B1}$, $R^1 = R^{C2}$, and
in $L_{A358}$: $R^E = R^{A8}$, $R^2 = R^{B2}$, $R^1 = R^{C2}$., wherein
in $L_{A359}$: $R^E = R^{A5}$, $R^2 = R^{B1}$, $R^1 = R^{C1}$,
in $L_{A360}$: $R^E = R^{A5}$, $R^2 = R^{B2}$, $R^1 = R^{C1}$,
in $L_{A361}$: $R^E = R^{A6}$, $R^2 = R^{B1}$, $R^1 = R^{C1}$,
in $L_{A362}$: $R^E = R^{A6}$, $R^2 = R^{B2}$, $R^1 = R^{C1}$,
in $L_{A363}$: $R^E = R^{A7}$, $R^2 = R^{B1}$, $R^1 = R^{C1}$,
in $L_{A364}$: $R^E = R^{A7}$, $R^2 = R^{B2}$, $R^1 = R^{C1}$,
in $L_{A365}$: $R^E = R^{A8}$, $R^2 = R^{B1}$, $R^1 = R^{C1}$,
in $L_{A366}$: $R^E = R^{A8}$, $R^2 = R^{B2}$, $R^1 = R^{C1}$,
in $L_{A367}$: $R^E = R^{A5}$, $R^2 = R^{B1}$, $R^1 = R^{C2}$,
in $L_{A368}$: $R^E = R^{A5}$, $R^2 = R^{B2}$, $R^1 = R^{C2}$,
in $L_{A369}$: $R^E = R^{A6}$, $R^2 = R^{B1}$, $R^1 = R^{C2}$,
in $L_{A370}$: $R^E = R^{A6}$, $R^2 = R^{B2}$, $R^1 = R^{C2}$,
in $L_{A371}$: $R^E = R^{A7}$, $R^2 = R^{B1}$, $R^1 = R^{C2}$,
in $L_{A372}$: $R^E = R^{A7}$, $R^2 = R^{B2}$, $R^1 = R^{C2}$,
in $L_{A373}$: $R^E = R^{A8}$, $R^2 = R^{B1}$, $R^1 = R^{C2}$, and
in $L_{A374}$: $R^E = R^{A8}$, $R^2 = R^{B2}$, $R^1 = R^{C2}$.,

| $L_{A375}$ through $L_{A382}$, each represented by the formula: | $L_{A383}$ through $L_{A390}$, each represented by the formula: |
|---|---|
| 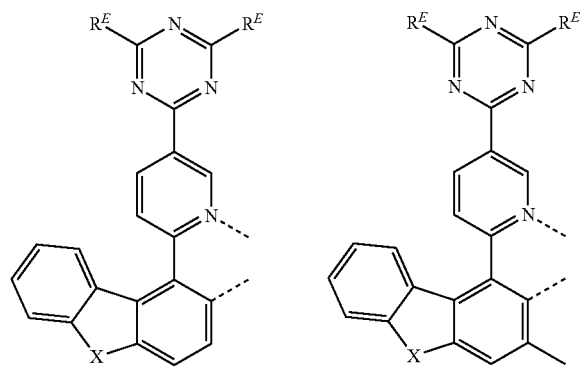 | | wherein
in $L_{A375}$: X=O, $R^E = R^{A5}$,
in $L_{A376}$: X=O, $R^E = R^{A6}$,
in $L_{A377}$: X=O, $R^E = R^{A7}$,
in $L_{A378}$: X=O, $R^E = R^{A8}$,
in $L_{A379}$: X=S, $R^E = R^{A5}$,
in $L_{A380}$: X=S, $R^E = R^{A5}$,
in $L_{A381}$: X=S, $R^E = R^{A7}$, and
in $L_{A382}$: X=S, $R^E = R^{A8}$., wherein
in $L_{A383}$: X=O, $R^E = R^{A5}$,
in $L_{A384}$: X=O, $R^E = R^{A6}$,
in $L_{A385}$: X=O, $R^E = R^{A7}$,
in $L_{A386}$: X=O, $R^E = R^{A8}$,
in $L_{A387}$: X=S, $R^E = R^{A5}$,
in $L_{A388}$: X=S, $R^E = R^{A5}$,
in $L_{A389}$: X=S, $R^E = R^{A7}$, and
in $L_{A390}$: X=S, $R^E = R^{A8}$., L$_{A391}$ through L$_{A406}$, each represented by the formula:

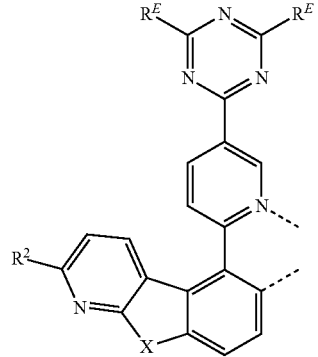

L$_{A407}$ through L$_{A422}$, each represented by the formula:

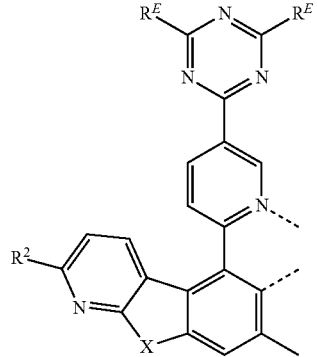

wherein
in L$_{A391}$: X=O, R$^E$ = R$^{A5}$, R$^2$ = R$^{B1}$,
in L$_{A392}$: X=O, R$^E$ = R$^{A5}$, R$^2$ = R$^{B2}$,
in L$_{A393}$: X=O, R$^E$ = R$^{A6}$, R$^2$ = R$^{B1}$,
in L$_{A394}$: X=O, R$^E$ = R$^{A6}$, R$^2$ = R$^{B2}$,
in L$_{A395}$: X=O, R$^E$ = R$^{A7}$, R$^2$ = R$^{B1}$,
in L$_{A396}$: X=O, R$^E$ = R$^{A7}$, R$^2$ = R$^{B2}$,
in L$_{A397}$: X=O, R$^E$ = R$^{A8}$, R$^2$ = R$^{B1}$,
in L$_{A398}$: X=O, R$^E$ = R$^{A8}$, R$^2$ = R$^{B2}$,
in L$_{A399}$: X=S, R$^E$ = R$^{A5}$, R$^2$ = R$^{B1}$,
in L$_{A400}$: X=S, R$^E$ = R$^{A5}$, R$^2$ = R$^{B2}$,
in L$_{A401}$: X=S, R$^E$ = R$^{A6}$, R$^2$ = R$^{B1}$,
in L$_{A402}$: X=S, R$^E$ = R$^{A6}$, R$^2$ = R$^{B2}$,
in L$_{A403}$: X=S, R$^E$ = R$^{A7}$, R$^2$ = R$^{B1}$,
in L$_{A404}$: X=S, R$^E$ = R$^{A7}$, R$^2$ = R$^{B2}$,
in L$_{A405}$: X=S, R$^E$ = R$^{A8}$, R$^2$ = R$^{B1}$, and
in L$_{A406}$: X=S, R$^E$ = R$^{A8}$, R$^2$ = R$^{B2}$., wherein
in L$_{A407}$: X=O, R$^E$ = R$^{A5}$, R$^2$ = R$^{B1}$,
in L$_{A408}$: X=O, R$^E$ = R$^{A5}$, R$^2$ = R$^{B2}$,
in L$_{A409}$: X=O, R$^E$ = R$^{A6}$, R$^2$ = R$^{B1}$,
in L$_{A410}$: X=O, R$^E$ = R$^{A6}$, R$^2$ = R$^{B2}$,
in L$_{A411}$: X=O, R$^E$ = R$^{A7}$, R$^2$ = R$^{B1}$,
in L$_{A412}$: X=O, R$^E$ = R$^{A7}$, R$^2$ = R$^{B2}$,
in L$_{A413}$: X=O, R$^E$ = R$^{A8}$, R$^2$ = R$^{B1}$,
in L$_{A414}$: X=O, R$^E$ = R$^{A8}$, R$^2$ = R$^{B2}$,
in L$_{A415}$: X=S, R$^E$ = R$^{A5}$, R$^2$ = R$^{B1}$,
in L$_{A416}$: X=S, R$^E$ = R$^{A5}$, R$^2$ = R$^{B2}$,
in L$_{A417}$: X=S, R$^E$ = R$^{A6}$, R$^2$ = R$^{B1}$,
in L$_{A418}$: X=S, R$^E$ = R$^{A6}$, R$^2$ = R$^{B2}$,
in L$_{A419}$: X=S, R$^E$ = R$^{A7}$, R$^2$ = R$^{B1}$,
in L$_{A420}$: X=S, R$^E$ = R$^{A7}$, R$^2$ = R$^{B2}$,
in L$_{A421}$: X=S, R$^E$ = R$^{A8}$, R$^2$ = R$^{B1}$, and
in L$_{A422}$: X=S, R$^E$ = R$^{A8}$, R$^2$ = R$^{B2}$., L$_{A423}$ through L$_{A438}$, each represented by the formula:

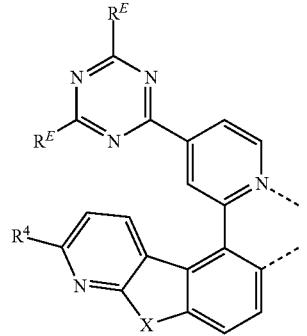

L$_{A439}$ through L$_{A454}$, each represented by the formula:

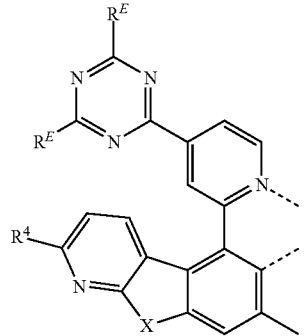

wherein
in L$_{A423}$: X=O, R$^E$ = R$^{A5}$, R$^2$ = R$^{B1}$,
in L$_{A424}$: X=O, R$^E$ = R$^{A5}$, R$^2$ = R$^{B2}$,
in L$_{A425}$: X=O, R$^E$ = R$^{A6}$, R$^2$ = R$^{B1}$,
in L$_{A426}$: X=O, R$^E$ = R$^{A6}$, R$^2$ = R$^{B2}$,
in L$_{A427}$: X=O, R$^E$ = R$^{A7}$, R$^2$ = R$^{B1}$,
in L$_{A428}$: X=O, R$^E$ = R$^{A7}$, R$^2$ = R$^{B2}$,
in L$_{A429}$: X=O, R$^E$ = R$^{A8}$, R$^2$ = R$^{B1}$,
in L$_{A430}$: X=O, R$^E$ = R$^{A8}$, R$^2$ = R$^{B2}$,
in L$_{A431}$: X=S, R$^E$ = R$^{A5}$, R$^2$ = R$^{B1}$,
in L$_{A432}$: X=S, R$^E$ = R$^{A5}$, R$^2$ = R$^{B2}$,
in L$_{A433}$: X=S, R$^E$ = R$^{A6}$, R$^2$ = R$^{B1}$,
in L$_{A434}$: X=S, R$^E$ = R$^{A6}$, R$^2$ = R$^{B2}$,
in L$_{A435}$: X=S, R$^E$ = R$^{A7}$, R$^2$ = R$^{B1}$,
in L$_{A436}$: X=S, R$^E$ = R$^{A7}$, R$^2$ = R$^{B2}$,
in L$_{A437}$: X=S, R$^E$ = R$^{A8}$, R$^2$ = R$^{B1}$, and
in L$_{A438}$: X=S, R$^E$ = R$^{A8}$, R$^2$ = R$^{B2}$., wherein
in L$_{A439}$: X=O, R$^E$ = R$^{A5}$, R$^2$ = R$^{B1}$,
in L$_{A440}$: X=O, R$^E$ = R$^{A5}$, R$^2$ = R$^{B2}$,
in L$_{A441}$: X=O, R$^E$ = R$^{A6}$, R$^2$ = R$^{B1}$,
in L$_{A442}$: X=O, R$^E$ = R$^{A6}$, R$^2$ = R$^{B2}$,
in L$_{A443}$: X=O, R$^E$ = R$^{A7}$, R$^2$ = R$^{B1}$,
in L$_{A444}$: X=O, R$^E$ = R$^{A7}$, R$^2$ = R$^{B2}$,
in L$_{A445}$: X=O, R$^E$ = R$^{A8}$, R$^2$ = R$^{B1}$,
in L$_{A446}$: X=O, R$^E$ = R$^{A8}$, R$^2$ = R$^{B2}$,
in L$_{A447}$: X=S, R$^E$ = R$^{A5}$, R$^2$ = R$^{B1}$,
in L$_{A448}$: X=S, R$^E$ = R$^{A5}$, R$^2$ = R$^{B2}$,
in L$_{A449}$: X=S, R$^E$ = R$^{A6}$, R$^2$ = R$^{B1}$,
in L$_{A450}$: X=S, R$^E$ = R$^{A6}$, R$^2$ = R$^{B2}$,
in L$_{A451}$: X=S, R$^E$ = R$^{A7}$, R$^2$ = R$^{B1}$,
in L$_{A452}$: X=S, R$^E$ = R$^{A7}$, R$^2$ = R$^{B2}$,
in L$_{A453}$: X=S, R$^E$ = R$^{A8}$, R$^2$ = R$^{B1}$, and
in L$_{A454}$: X=S, R$^E$ = R$^{A8}$, R$^2$ = R$^{B2}$., L$_{A455}$ through L$_{A462}$, each represented by the formula:

L$_{A463}$ through L$_{A470}$, each represented by the formula:

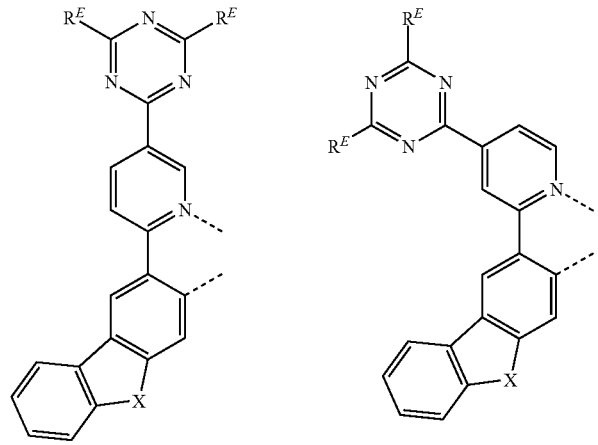

wherein
in L$_{A455}$: X=O, R$^E$ = R$^{A5}$,
in L$_{A456}$: X=O, R$^E$ = R$^{A6}$,
in L$_{A457}$: X=O, R$^E$ = R$^{A7}$,
in L$_{A458}$: X=O, R$^E$ = R$^{A8}$,
in L$_{A459}$: X=S, R$^E$ = R$^{A5}$,
in L$_{A460}$: X=S, R$^E$ = R$^{A6}$,
in L$_{A461}$: X=S, R$^E$ = R$^{A7}$, and
in L$_{A462}$: X=S, R$^E$ = R$^{A8}$.

wherein
in L$_{A463}$: X=O, R$^E$ = R$^{A5}$,
in L$_{A464}$: X=O, R$^E$ = R$^{A6}$,
in L$_{A465}$: X=O, R$^E$ = R$^{A7}$,
in L$_{A466}$: X=O, R$^E$ = R$^{A8}$,
in L$_{A467}$: X=S, R$^E$ = R$^{A5}$,
in L$_{A468}$: X=S, R$^E$ = R$^{A6}$,
in L$_{A469}$: X=S, R$^E$ = R$^{A7}$, and
in L$_{A470}$: X=S, R$^E$ = R$^{A8}$., L$_{A471}$ through L$_{A478}$, each represented by the formula:

L$_{A479}$ through L$_{A486}$, each represented by the formula:

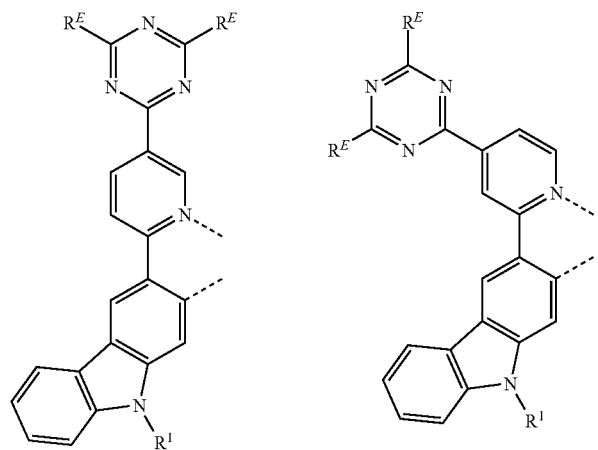

wherein
in L$_{A471}$: R$^E$ = R$^{A5}$, R$^1$ = R$^{C1}$,
in L$_{A472}$: R$^E$ = R$^{A6}$, R$^1$ = R$^{C1}$,
in L$_{A473}$: R$^E$ = R$^{A7}$, R$^1$ = R$^{C1}$,
in L$_{A474}$: R$^E$ = R$^{A8}$, R$^1$ = R$^{C1}$,
in L$_{A475}$: R$^E$ = R$^{A5}$, R$^1$ = R$^{C2}$,
in L$_{A476}$: R$^E$ = R$^{A6}$, R$^1$ = R$^{C2}$,
in L$_{A477}$: R$^E$ = R$^{A7}$, R$^1$ = R$^{C2}$, and
in L$_{A478}$: R$^E$ = R$^{A8}$, R$^1$ = R$^{C2}$.

wherein
in L$_{A463}$: R$^E$ = R$^{A5}$, R$^1$ = R$^{C1}$,
in L$_{A464}$: R$^E$ = R$^{A6}$, R$^1$ = R$^{C1}$,
in L$_{A465}$: R$^E$ = R$^{A7}$, R$^1$ = R$^{C1}$,
in L$_{A466}$: R$^E$ = R$^{A8}$, R$^1$ = R$^{C1}$,
in L$_{A467}$: R$^E$ = R$^{A5}$, R$^1$ = R$^{C2}$,
in L$_{A468}$: R$^E$ = R$^{A6}$, R$^1$ = R$^{C2}$,
in L$_{A469}$: R$^E$ = R$^{A7}$, R$^1$ = R$^{C2}$, and
in L$_{A470}$: R$^E$ = R$^{A8}$, R$^1$ = R$^{C2}$., -continued

| $L_{A487}$ through $L_{A494}$, each represented by the formula: | $L_{A495}$ through $L_{A502}$, each represented by the formula: |
|---|---|
| 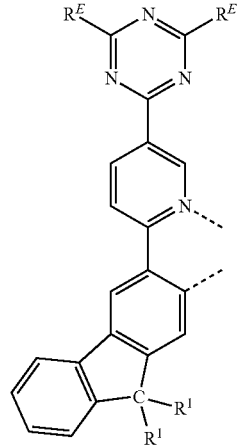 | 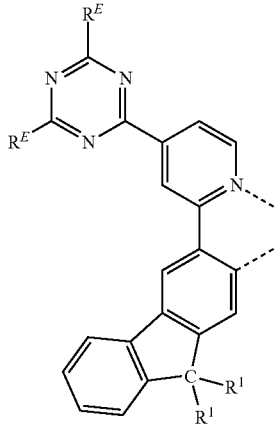 |
| wherein<br>in $L_{A487}$: $R^E = R^{45}$, $R^1 = R^{C1}$,<br>in $L_{A488}$: $R^E = R^{46}$, $R^1 = R^{C1}$,<br>in $L_{A489}$: $R^E = R^{47}$, $R^1 = R^{C1}$,<br>in $L_{A490}$: $R^E = R^{48}$, $R^1 = R^{C1}$,<br>in $L_{A491}$: $R^E = R^{45}$, $R^1 = R^{C2}$,<br>in $L_{A492}$: $R^E = R^{46}$, $R^1 = R^{C2}$,<br>in $L_{A493}$: $R^E = R^{47}$, $R^1 = R^{C2}$, and<br>in $L_{A494}$: $R^E = R^{48}$, $R^1 = R^{C2}$. | wherein<br>in $L_{A495}$: $R^E = R^{45}$, $R^1 = R^{C1}$,<br>in $L_{A496}$: $R^E = R^{46}$, $R^1 = R^{C1}$,<br>in $L_{A497}$: $R^E = R^{47}$, $R^1 = R^{C1}$,<br>in $L_{A498}$: $R^E = R^{48}$, $R^1 = R^{C1}$,<br>in $L_{A499}$: $R^E = R^{45}$, $R^1 = R^{C2}$,<br>in $L_{A500}$: $R^E = R^{46}$, $R^1 = R^{C2}$,<br>in $L_{A501}$: $R^E = R^{47}$, $R^1 = R^{C2}$, and<br>in $L_{A502}$: $R^E = R^{48}$, $R^1 = R^{C2}$., |

| $L_{A503}$ through $L_{A518}$, each represented by the formula: | $L_{A519}$ through $L_{A534}$, each represented by the formula: |
|---|---|
| 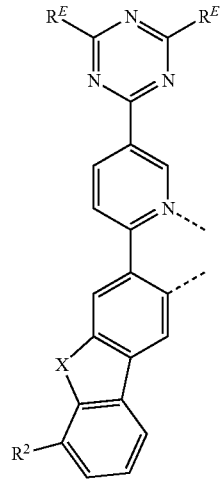 | 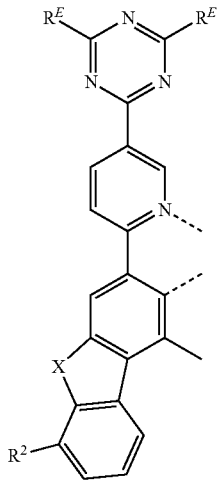 |
| wherein<br>in $L_{A503}$: X=O, $R^E = R^{45}$, $R^2 = R^{B1}$,<br>in $L_{A504}$: X=O, $R^E = R^{45}$, $R^2 = R^{B2}$,<br>in $L_{A505}$: X=O, $R^E = R^{46}$, $R^2 = R^{B1}$,<br>in $L_{A506}$: X=O, $R^E = R^{46}$, $R^2 = R^{B2}$,<br>in $L_{A507}$: X=O, $R^E = R^{47}$, $R^2 = R^{B1}$,<br>in $L_{A508}$: X=O, $R^E = R^{47}$, $R^2 = R^{B2}$,<br>in $L_{A509}$: X=O, $R^E = R^{48}$, $R^2 = R^{B1}$,<br>in $L_{A510}$: X=O, $R^E = R^{48}$, $R^2 = R^{B2}$,<br>in $L_{A511}$: X=S, $R^E = R^{45}$, $R^2 = R^{B1}$,<br>in $L_{A512}$: X=S, $R^E = R^{45}$, $R^2 = R^{B2}$,<br>in $L_{A513}$: X=S, $R^E = R^{46}$, $R^2 = R^{B1}$,<br>in $L_{A514}$: X=S, $R^E = R^{46}$, $R^2 = R^{B2}$,<br>in $L_{A515}$: X=S, $R^E = R^{47}$, $R^2 = R^{B1}$,<br>in $L_{A516}$: X=S, $R^E = R^{47}$, $R^2 = R^{B2}$,<br>in $L_{A517}$: X=S, $R^E = R^{48}$, $R^2 = R^{B1}$, and<br>in $L_{A518}$: X=S, $R^E = R^{48}$, $R^2 = R^{B2}$., | wherein<br>in $L_{A519}$: X=O, $R^E = R^{45}$, $R^2 = R^{B1}$,<br>in $L_{A520}$: X=O, $R^E = R^{45}$, $R^2 = R^{B2}$,<br>in $L_{A521}$: X=O, $R^E = R^{46}$, $R^2 = R^{B1}$,<br>in $L_{A522}$: X=O, $R^E = R^{46}$, $R^2 = R^{B2}$,<br>in $L_{A523}$: X=O, $R^E = R^{47}$, $R^2 = R^{B1}$,<br>in $L_{A524}$: X=O, $R^E = R^{47}$, $R^2 = R^{B2}$,<br>in $L_{A525}$: X=O, $R^E = R^{48}$, $R^2 = R^{B1}$,<br>in $L_{A526}$: X=O, $R^E = R^{48}$, $R^2 = R^{B2}$,<br>in $L_{A527}$: X=S, $R^E = R^{45}$, $R^2 = R^{B1}$,<br>in $L_{A528}$: X=S, $R^E = R^{45}$, $R^2 = R^{B2}$,<br>in $L_{A529}$: X=S, $R^E = R^{46}$, $R^2 = R^{B1}$,<br>in $L_{A530}$: X=S, $R^E = R^{46}$, $R^2 = R^{B2}$,<br>in $L_{A531}$: X=S, $R^E = R^{47}$, $R^2 = R^{B1}$,<br>in $L_{A532}$: X=S, $R^E = R^{47}$, $R^2 = R^{B2}$,<br>in $L_{A533}$: X=S, $R^E = R^{48}$, $R^2 = R^{B1}$, and<br>in $L_{A534}$: X=S, $R^E = R^{48}$, $R^2 = R^{B2}$., |

| $L_{A535}$ through $L_{A550}$, each represented by the formula: | $L_{A551}$ through $L_{A566}$, each represented by the formula: |
|---|---|

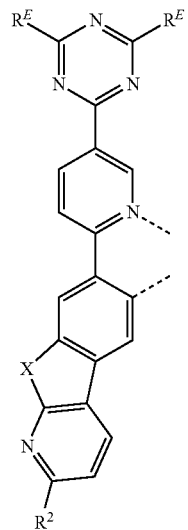
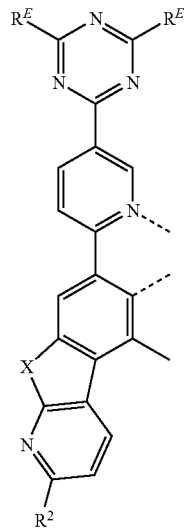

wherein
in $L_{A535}$: X=O, $R^E = R^{45}$, $R^2 = R^{B1}$,
in $L_{A536}$: X=O, $R^E = R^{45}$, $R^2 = R^{B2}$,
in $L_{A537}$: X=O, $R^E = R^{46}$, $R^2 = R^{B1}$,
in $L_{A538}$: X=O, $R^E = R^{46}$, $R^2 = R^{B2}$,
in $L_{A539}$: X=O, $R^E = R^{47}$, $R^2 = R^{B1}$,
in $L_{A540}$: X=O, $R^E = R^{47}$, $R^2 = R^{B2}$,
in $L_{A541}$: X=O, $R^E = R^{48}$, $R^2 = R^{B1}$,
in $L_{A542}$: X=O, $R^E = R^{48}$, $R^2 = R^{B2}$,
in $L_{A543}$: X=S, $R^E = R^{45}$, $R^2 = R^{B1}$,
in $L_{A544}$: X=S, $R^E = R^{45}$, $R^2 = R^{B2}$,
in $L_{A545}$: X=S, $R^E = R^{46}$, $R^2 = R^{B1}$,
in $L_{A546}$: X=S, $R^E = R^{46}$, $R^2 = R^{B2}$,
in $L_{A547}$: X=S, $R^E = R^{47}$, $R^2 = R^{B1}$,
in $L_{A548}$: X=S, $R^E = R^{47}$, $R^2 = R^{B2}$,
in $L_{A549}$: X=S, $R^E = R^{48}$, $R^2 = R^{B1}$, and
in $L_{A550}$: X=S, $R^E = R^{48}$, $R^2 = R^{B2}$., wherein
in $L_{A551}$: X=O, $R^E = R^{45}$, $R^2 = R^{B1}$,
in $L_{A552}$: X=O, $R^E = R^{45}$, $R^2 = R^{B2}$,
in $L_{A553}$: X=O, $R^E = R^{46}$, $R^2 = R^{B1}$,
in $L_{A554}$: X=O, $R^E = R^{46}$, $R^2 = R^{B2}$,
in $L_{A555}$: X=O, $R^E = R^{47}$, $R^2 = R^{B1}$,
in $L_{A556}$: X=O, $R^E = R^{47}$, $R^2 = R^{B2}$,
in $L_{A557}$: X=O, $R^E = R^{48}$, $R^2 = R^{B1}$,
in $L_{A558}$: X=O, $R^E = R^{48}$, $R^2 = R^{B2}$,
in $L_{A559}$: X=S, $R^E = R^{45}$, $R^2 = R^{B1}$,
in $L_{A560}$: X=S, $R^E = R^{45}$, $R^2 = R^{B2}$,
in $L_{A561}$: X=S, $R^E = R^{46}$, $R^2 = R^{B1}$,
in $L_{A562}$: X=S, $R^E = R^{46}$, $R^2 = R^{B2}$,
in $L_{A563}$: X=S, $R^E = R^{47}$, $R^2 = R^{B1}$,
in $L_{A564}$: X=S, $R^E = R^{47}$, $R^2 = R^{B2}$,
in $L_{A565}$: X=S, $R^E = R^{48}$, $R^2 = R^{B1}$, and
in $L_{A566}$: X=S, $R^E = R^{48}$, $R^2 = R^{B2}$., -continued

| $L_{A567}$ through $L_{A582}$, each represented by the formula: | $L_{A551}$ through $L_{A598}$, each represented by the formula: |
|---|---|

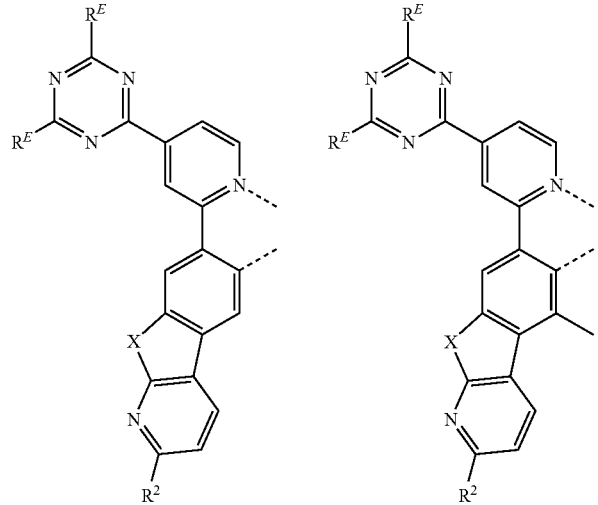

wherein
in $L_{A567}$: X=O, $R^E$ = $R^{45}$, $R^2$ = $R^{B1}$,
in $L_{A568}$: X=O, $R^E$ = $R^{45}$, $R^2$ = $R^{B2}$,
in $L_{A569}$: X=O, $R^E$ = $R^{46}$, $R^2$ = $R^{B1}$,
in $L_{A570}$: X=O, $R^E$ = $R^{46}$, $R^2$ = $R^{B2}$,
in $L_{A571}$: X=O, $R^E$ = $R^{47}$, $R^2$ = $R^{B1}$,
in $L_{A572}$: X=O, $R^E$ = $R^{47}$, $R^2$ = $R^{B2}$,
in $L_{A573}$: X=O, $R^E$ = $R^{48}$, $R^2$ = $R^{B1}$,
in $L_{A574}$: X=O, $R^E$ = $R^{48}$, $R^2$ = $R^{B2}$,
in $L_{A575}$: X=S, $R^E$ = $R^{45}$, $R^2$ = $R^{B1}$,
in $L_{A576}$: X=S, $R^E$ = $R^{45}$, $R^2$ = $R^{B2}$,
in $L_{A577}$: X=S, $R^E$ = $R^{46}$, $R^2$ = $R^{B1}$,
in $L_{A578}$: X=S, $R^E$ = $R^{46}$, $R^2$ = $R^{B2}$,
in $L_{A579}$: X=S, $R^E$ = $R^{47}$, $R^2$ = $R^{B1}$,
in $L_{A580}$: X=S, $R^E$ = $R^{47}$, $R^2$ = $R^{B2}$,
in $L_{A581}$: X=S, $R^E$ = $R^{48}$, $R^2$ = $R^{B1}$, and
in $L_{A582}$: X=S, $R^E$ = $R^{48}$, $R^2$ = $R^{B2}$., wherein
in $L_{A583}$: X=O, $R^E$ = $R^{45}$, $R^2$ = $R^{B1}$,
in $L_{A584}$: X=O, $R^E$ = $R^{45}$, $R^2$ = $R^{B2}$,
in $L_{A585}$: X=O, $R^E$ = $R^{46}$, $R^2$ = $R^{B1}$,
in $L_{A586}$: X=O, $R^E$ = $R^{46}$, $R^2$ = $R^{B2}$,
in $L_{A587}$: X=O, $R^E$ = $R^{47}$, $R^2$ = $R^{B1}$,
in $L_{A588}$: X=O, $R^E$ = $R^{47}$, $R^2$ = $R^{B2}$,
in $L_{A589}$: X=O, $R^E$ = $R^{48}$, $R^2$ = $R^{B1}$,
in $L_{A590}$: X=O, $R^E$ = $R^{48}$, $R^2$ = $R^{B2}$,
in $L_{A591}$: X=S, $R^E$ = $R^{45}$, $R^2$ = $R^{B1}$,
in $L_{A592}$: X=S, $R^E$ = $R^{45}$, $R^2$ = $R^{B2}$,
in $L_{A593}$: X=S, $R^E$ = $R^{46}$, $R^2$ = $R^{B1}$,
in $L_{A594}$: X=S, $R^E$ = $R^{46}$, $R^2$ = $R^{B2}$,
in $L_{A595}$: X=S, $R^E$ = $R^{47}$, $R^2$ = $R^{B1}$,
in $L_{A596}$: X=S, $R^E$ = $R^{47}$, $R^2$ = $R^{B2}$,
in $L_{A597}$: X=S, $R^E$ = $R^{48}$, $R^2$ = $R^{B1}$, and
in $L_{A598}$: X=S, $R^E$ = $R^{48}$, $R^2$ = $R^{B2}$., L$_{A599}$ through L$_{A606}$, each represented by the formula:

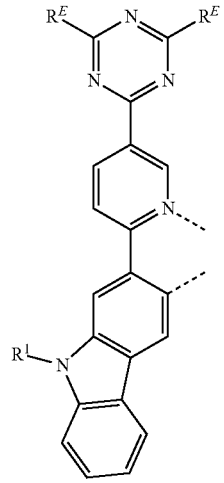

wherein
in L$_{A599}$: R$^E$ = R$^{A5}$, R$^1$ = R$^{C1}$,
in L$_{A600}$: R$^E$ = R$^{A6}$, R$^1$ = R$^{C1}$,
in L$_{A601}$: R$^E$ = R$^{A7}$, R$^1$ = R$^{C1}$,
in L$_{A602}$: R$^E$ = R$^{A8}$, R$^1$ = R$^{C1}$,
in L$_{A603}$: R$^E$ = R$^{A5}$, R$^1$ = R$^{C2}$,
in L$_{A604}$: R$^E$ = R$^{A6}$, R$^1$ = R$^{C2}$,
in L$_{A605}$: R$^E$ = R$^{A7}$, R$^1$ = R$^{C2}$, and
in L$_{A606}$: R$^E$ = R$^{A8}$, R$^1$ = R$^{C2}$., L$_{A607}$ through L$_{A614}$, each represented by the formula:

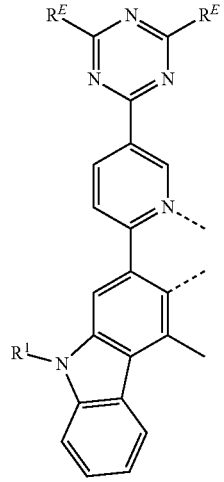

wherein
in L$_{A607}$: R$^E$ = R$^{A5}$, R$^1$ = R$^{C1}$,
in L$_{A608}$: R$^E$ = R$^{A6}$, R$^1$ = R$^{C1}$,
in L$_{A609}$: R$^E$ = R$^{A7}$, R$^1$ = R$^{C1}$,
in L$_{A610}$: R$^E$ = R$^{A8}$, R$^1$ = R$^{C1}$,
in L$_{A611}$: R$^E$ = R$^{A5}$, R$^1$ = R$^{C2}$,
in L$_{A612}$: R$^E$ = R$^{A6}$, R$^1$ = R$^{C2}$,
in L$_{A613}$: R$^E$ = R$^{A7}$, R$^1$ = R$^{C2}$, and
in L$_{A613}$: R$^E$ = R$^{A8}$, R$^1$ = R$^{C2}$., L$_{A615}$ through L$_{A622}$, each represented by the formula:

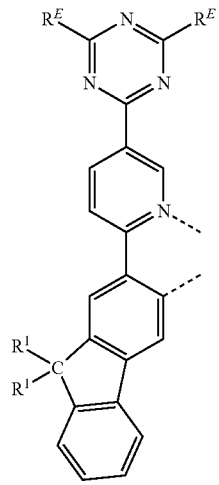

wherein
in L$_{A615}$: R$^E$ = R$^{A5}$, R$^1$ = R$^{C1}$,
in L$_{A616}$: R$^E$ = R$^{A6}$, R$^1$ = R$^{C1}$,
in L$_{A617}$: R$^E$ = R$^{A7}$, R$^1$ = R$^{C1}$,
in L$_{A618}$: R$^E$ = R$^{A8}$, R$^1$ = R$^{C1}$,
in L$_{A619}$: R$^E$ = R$^{A5}$, R$^1$ = R$^{C2}$,
in L$_{A620}$: R$^E$ = R$^{A6}$, R$^1$ = R$^{C2}$,
in L$_{A621}$: R$^E$ = R$^{A7}$, R$^1$ = R$^{C2}$, and
in L$_{A622}$: R$^E$ = R$^{A8}$, R$^1$ = R$^{C2}$., L$_{A623}$ through L$_{A630}$, each represented by the formula:

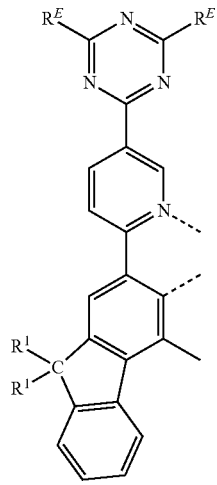

wherein
in L$_{A623}$: R$^E$ = R$^{A5}$, R$^1$ = R$^{C1}$,
in L$_{A624}$: R$^E$ = R$^{A6}$, R$^1$ = R$^{C1}$,
in L$_{A625}$: R$^E$ = R$^{A7}$, R$^1$ = R$^{C1}$,
in L$_{A626}$: R$^E$ = R$^{A8}$, R$^1$ = R$^{C1}$,
in L$_{A627}$: R$^E$ = R$^{A5}$, R$^1$ = R$^{C2}$,
in L$_{A628}$: R$^E$ = R$^{A6}$, R$^1$ = R$^{C2}$,
in L$_{A629}$: R$^E$ = R$^{A7}$, R$^1$ = R$^{C2}$, and
in L$_{A630}$: R$^E$ = R$^{A8}$, R$^1$ = R$^{C2}$., wherein R^{A5} to R^{A8} have the following structures:
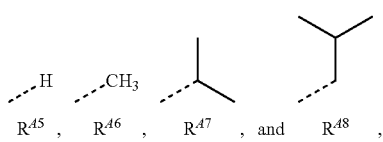
wherein R^{B1} and R^{B2} have the following structures:
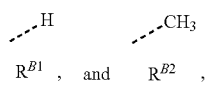
and wherein R^{C1} to R^{C2} have the following structures:
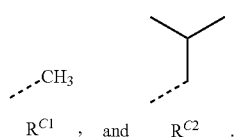
The Triazine embodiment wherein $L_B$ is selected from the group consisting of:
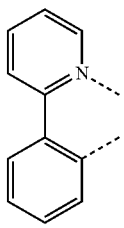
$L_{B1}$
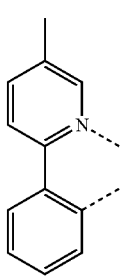
$L_{B2}$
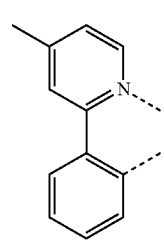
$L_{B3}$
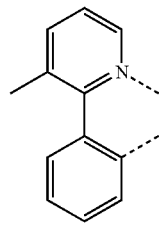
$L_{B4}$
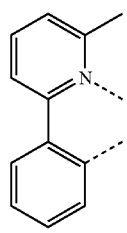
$L_{B5}$
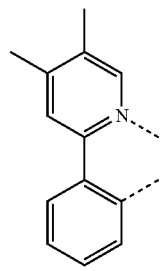
$L_{B6}$
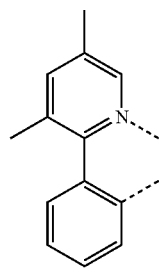
$L_{B7}$
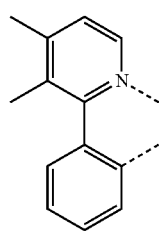
$L_{B8}$
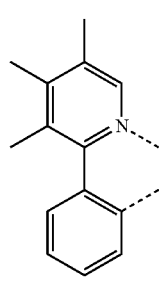
$L_{B9}$ L_{B10}
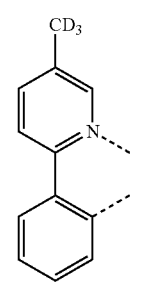
L_{B11}
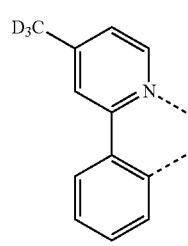
L_{B12}
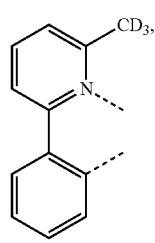
L_{B13}
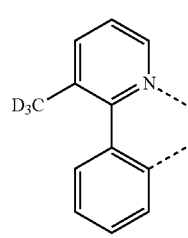
L_{B14}
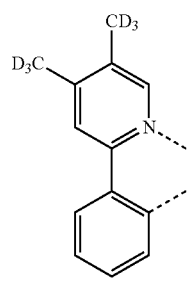
L_{B15}
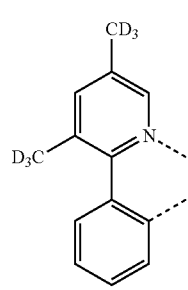
L_{B16}
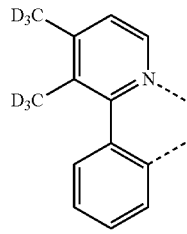
L_{B17}
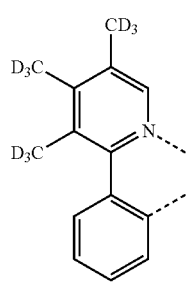
L_{B18}
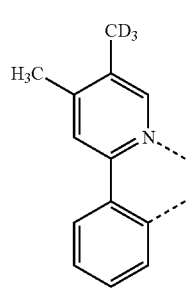
L_{B19}
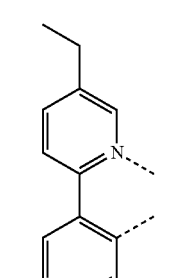
L_{B20}
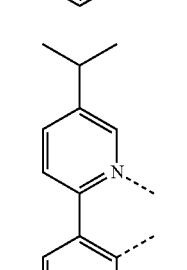
L_{B21}
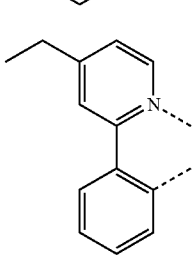

L_{B22}
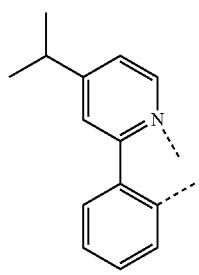
L_{B23}
L_{B24}
L_{B25}
L_{B26}
L_{B27}
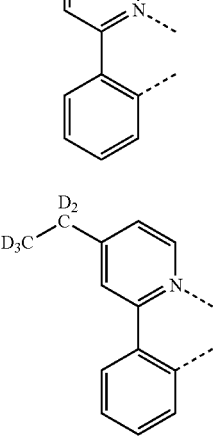
L_{B28}
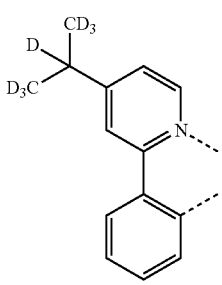
L_{B30}
L_{B31}
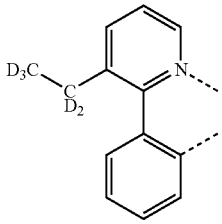
L_{B32}
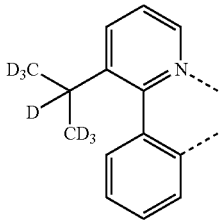
L_{B33}
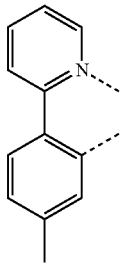
L_{B34}
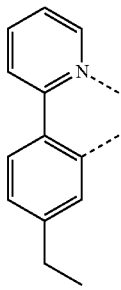
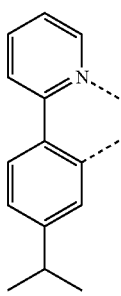

-continued
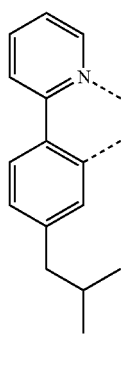
L_{B35}
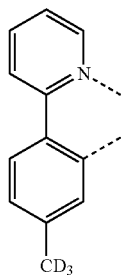
L_{B36}
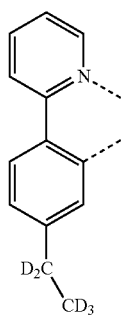
L_{B37}
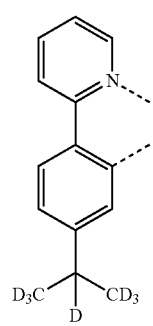
L_{B38}
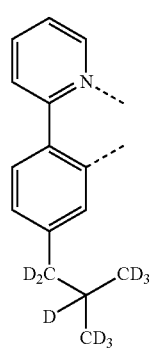
L_{B39}
-continued
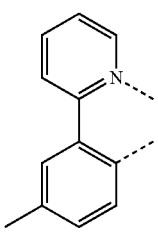
L_{B40}
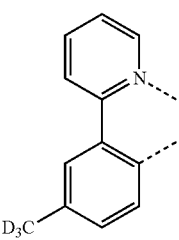
L_{B41}
The Triazine embodiment wherein $L_C$ is selected from the group consisting of:
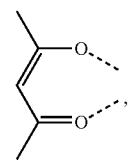
L_{C1}
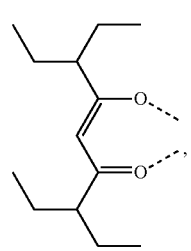
L_{C2}
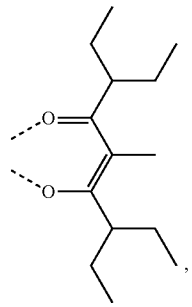
L_{C3}
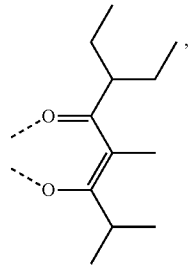
L_{C4}

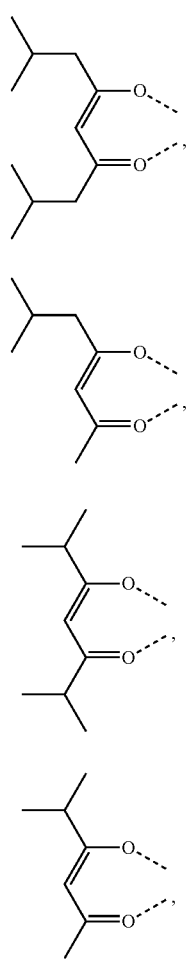
L<sub>C5</sub>
L<sub>C6</sub>
L<sub>C7</sub>
L<sub>C8</sub>

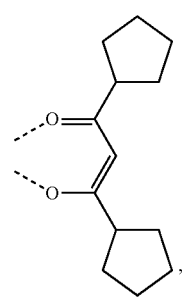
L<sub>C9</sub>

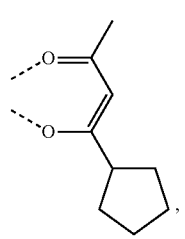
L<sub>C10</sub>

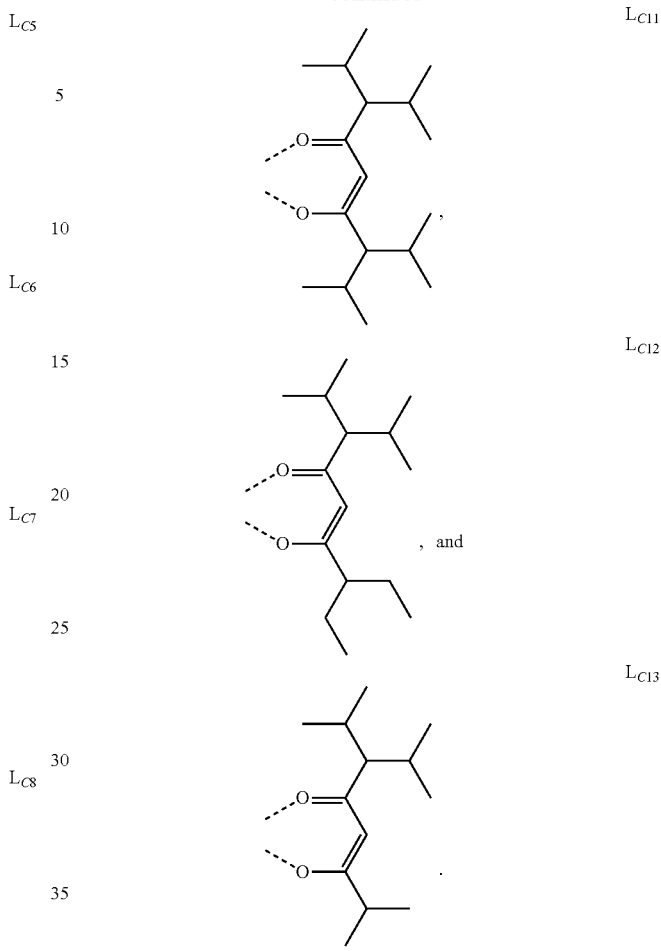
L<sub>C11</sub>, L<sub>C12</sub>, and L<sub>C13</sub>

In some embodiments, the compound is selected from the group consisting of Compound 1 through Compound 25,830, wherein each Compound x has the formula Ir(L$_{Ak}$)(L$_{Bj}$)$_2$, wherein x=630j+k−630, k is an integer from 1 to 630, and j is an integer from 1 to 41.

In some embodiments, the compound is selected from the group consisting of Compound 25,831 through Compound 34,020, wherein each Compound x has the formula Ir(L$_{Ak}$)$_2$(L$_{Ci}$), wherein x=(630i+k−630)+25,830, k is an integer from 1 to 630, and i is an integer from 1 to 13.

According to another aspect of the present disclosure, a device that includes one or more organic light emitting devices is also provided. At least one of the one or more organic light emitting devices can include an anode, a cathode, and an organic layer disposed between the anode and the cathode. The organic layer may include a host and a phosphorescent dopant. The emissive layer can include the compound according to Formula M(L$_A$)$_x$(L$_B$)$_y$(L$_C$)$_z$, and its variations as described herein.

The device can be one or more of a consumer product, an electronic component module, an organic light-emitting device and a lighting panel. The organic layer can be an emissive layer and the compound can be an emissive dopant in some embodiments, while the compound can be a non-emissive dopant in other embodiments.

The organic layer can also include a host. In some embodiments, the host can include a metal complex. The host can be a triphenylene containing benzo-fused thiophene or benzo-fused furan. Any substituent in the triphenylene containing benzo-fused thiophene or benzo-fused furan host can be an unfused substituent independently selected from the group consisting of $CH_{2n+1}$, $OC_nH_{2n+1}$, $OAr_1$, $N(C_nH_{2n+1})_2$, $N(Ar_1)(Ar_2)$, $CH=CH-CH_{2n+1}$, $C\equiv C-C_nH_{2n+1}$, $Ar_1$, $Ar_1$-$Ar_2$, and $CH_2$-$Ar_1$, or no substitution. In the preceding substituents, n can range from 1 to 10; and $Ar_1$ and $Ar_2$ can be independently selected from the group consisting of benzene, biphenyl, naphthalene, triphenylene, carbazole, and heteroaromatic analogs thereof.

The host can be a compound comprising at least one chemical group selected from the group consisting of triphenylene, carbazole, dibenzothiphene, dibenzofuran, dibenzoselenophene, azatriphenylene, azacarbazole, aza-dibenzothiophene, aza-dibenzofuran, and aza-dibenzoselenophene. The host can be a specific compound selected from the group consisting of:

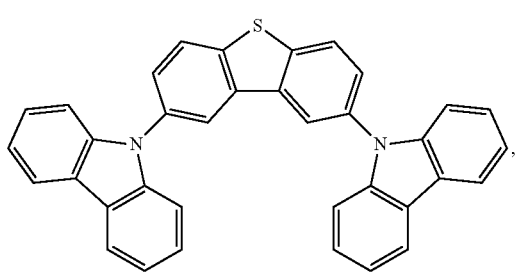

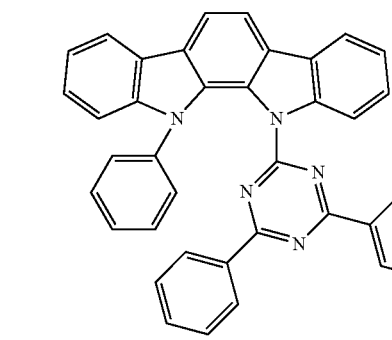

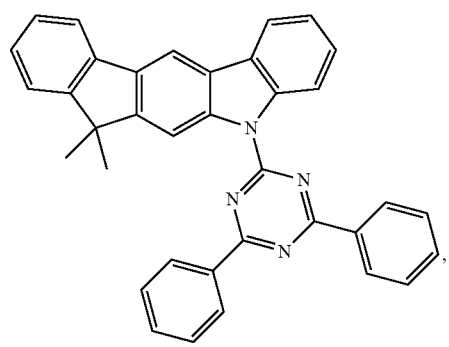

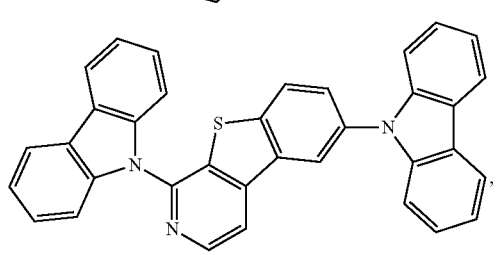

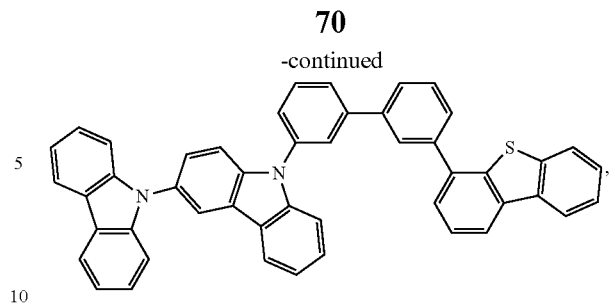

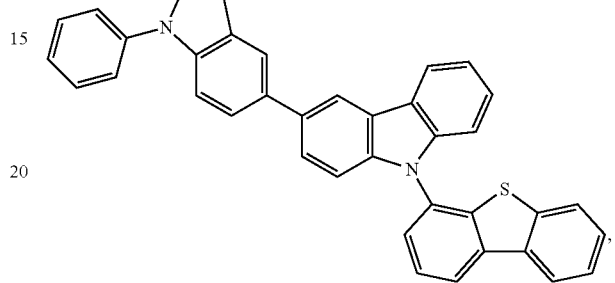

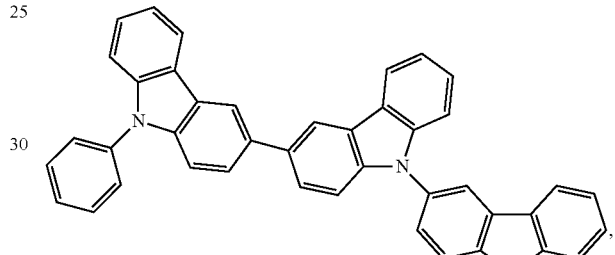

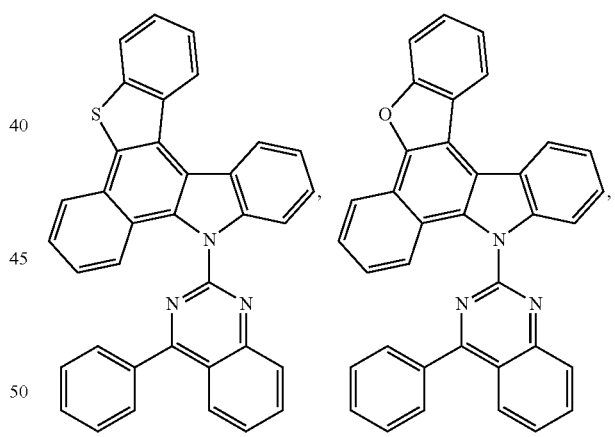

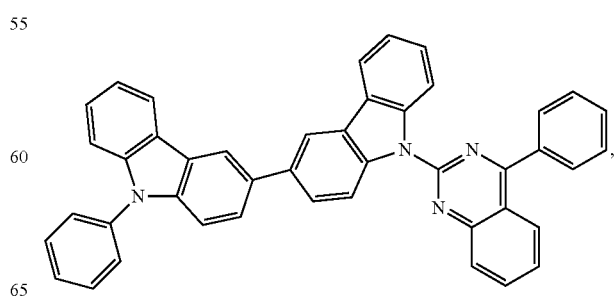

71
-continued
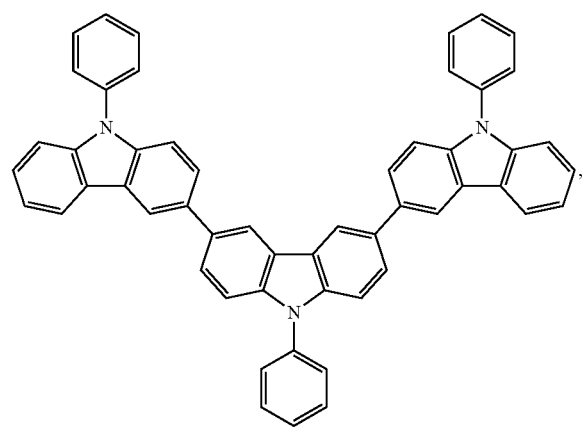
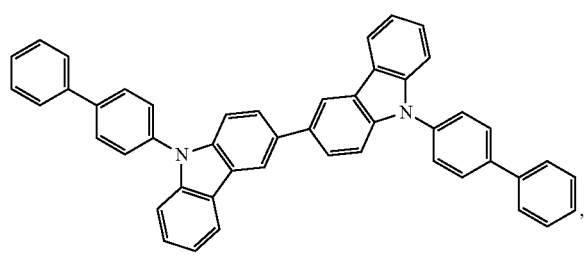
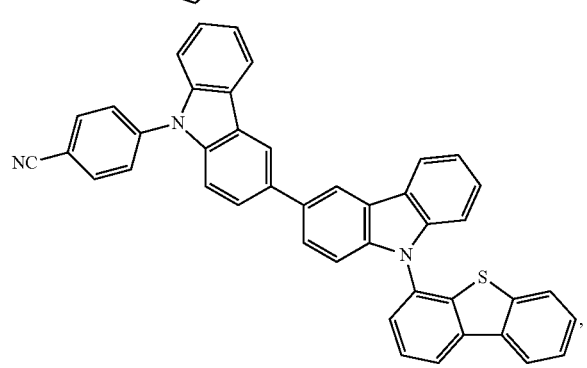
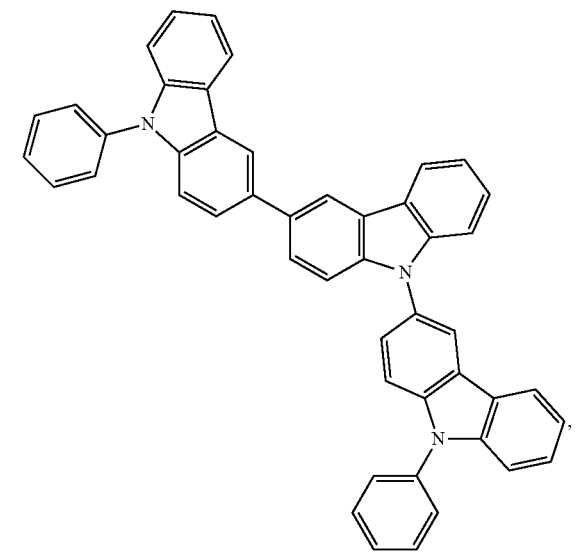
72
-continued
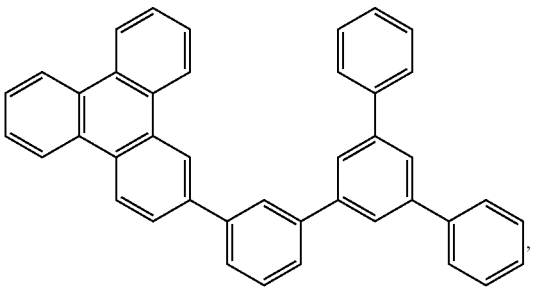
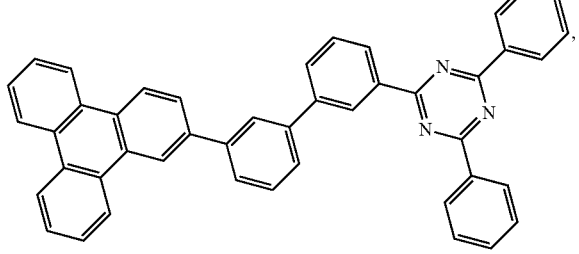
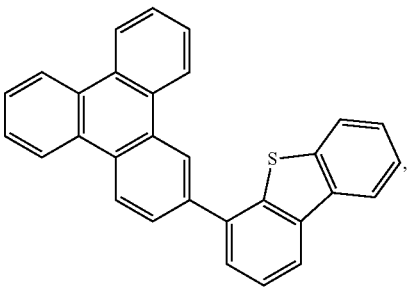
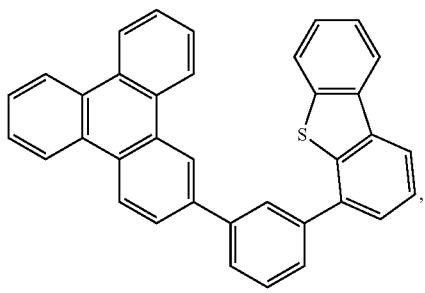
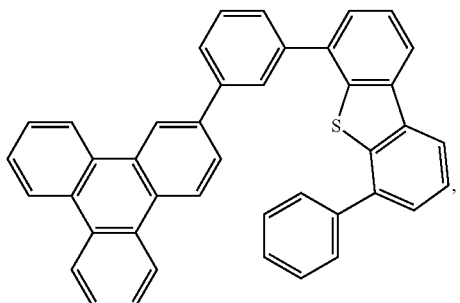
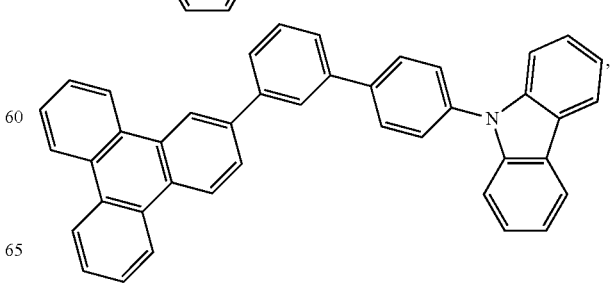

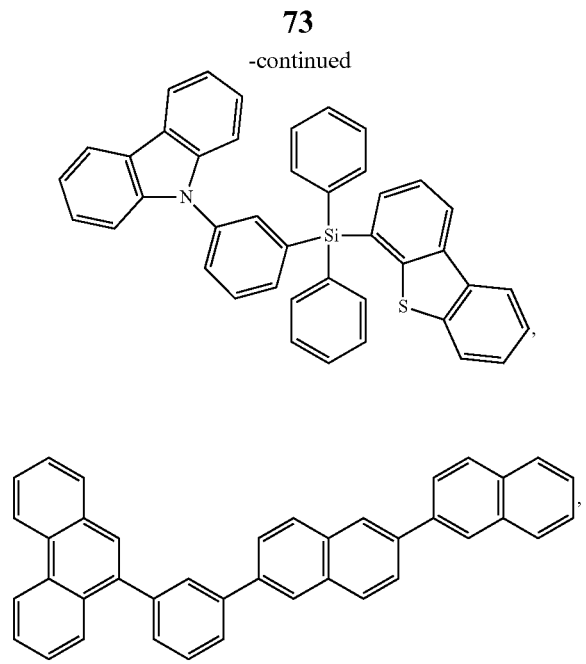

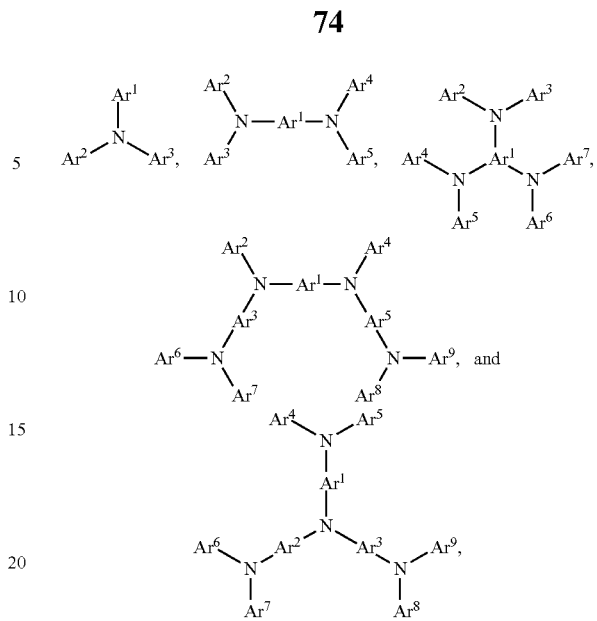

and combinations thereof.

In yet another aspect of the present disclosure, a formulation that comprises the compound according to Formula $M(L_A)_x(L_B)_y(L_C)_z$ is described and its variants described herein. The formulation can include one or more components selected from the group consisting of a solvent, a host, a hole injection material, hole transport material, and an electron transport layer material, disclosed herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compounds.

Examples of aromatic amine derivatives used in HIL or HTL include, but are not limited to, the following general structures:

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

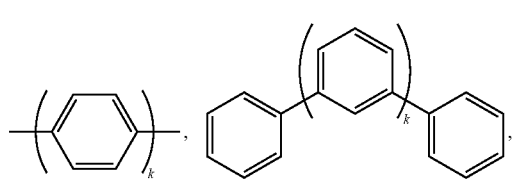

-continued

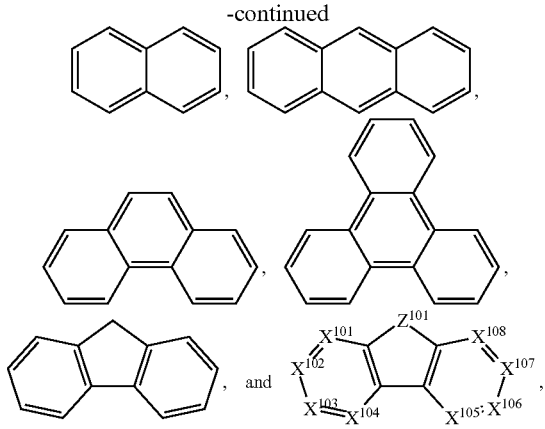

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but are not limited to, the following general formula:

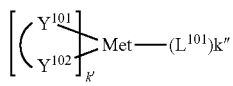

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

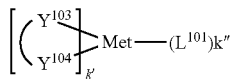

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

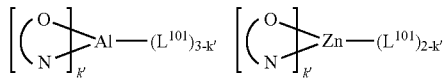

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, the host compound contains at least one of the following groups in the molecule:

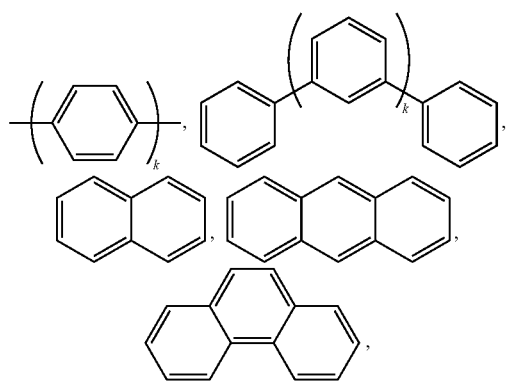

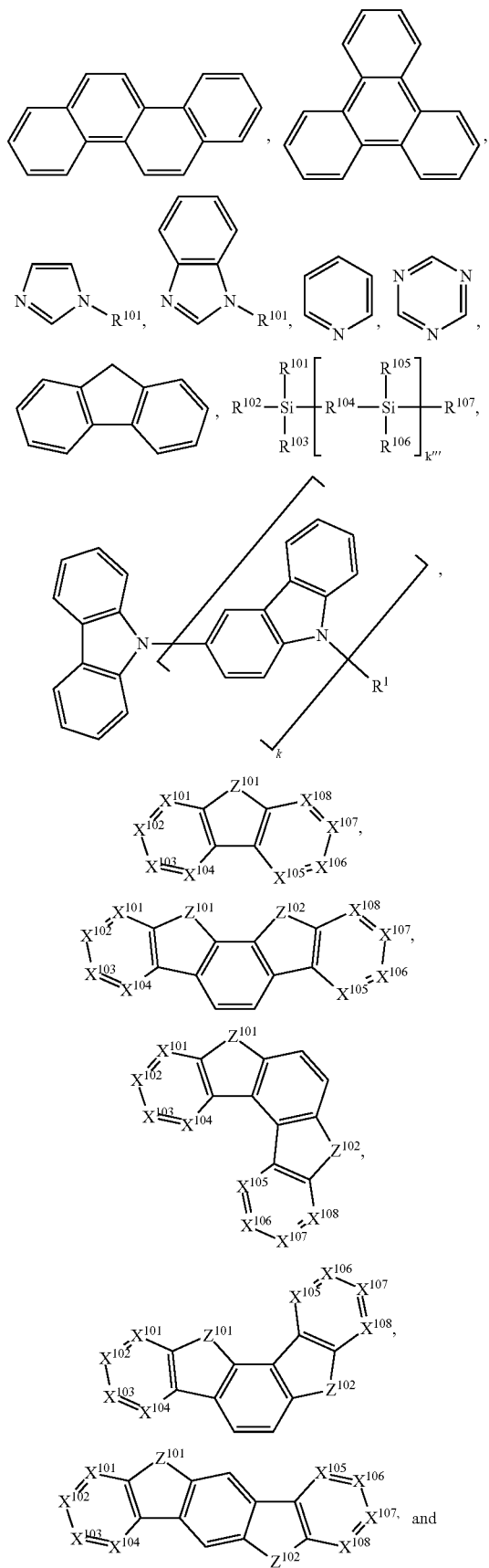

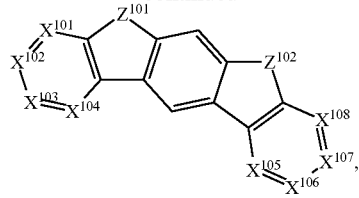

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20; k''' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

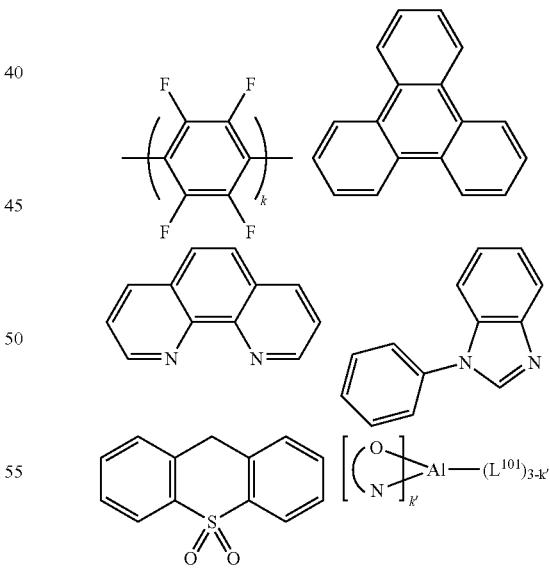

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

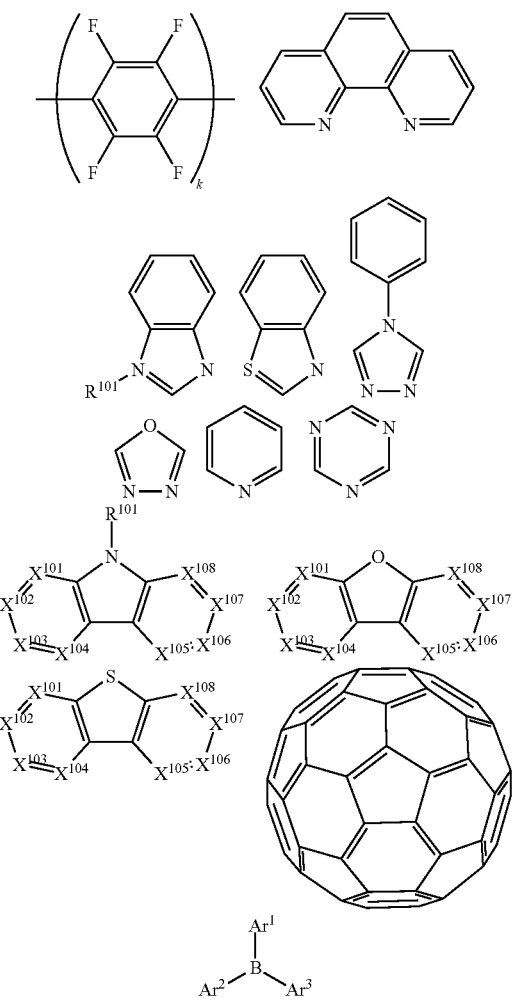

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL contains, but are not limited to, the following general formula:

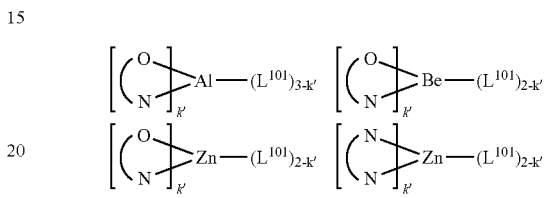

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
| --- | --- | --- |
| | Hole injection materials | |
| Phthalocyanine and porphyrin compounds | | Appl. Phys. Lett. 69, 2160 (1996) |

TABLE A-continued
| MATERIAL | EXAMPLES OF MATERIAL | PUBLICATIONS |
|---|---|---|
| Starburst triarylamines | 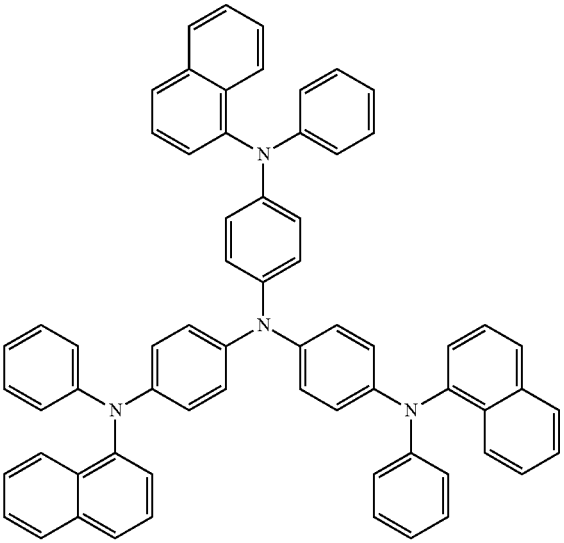 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 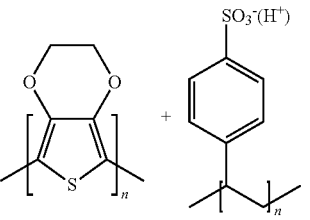 | Synth. Met. 87, 171 (1997)<br>WO2007002683 |
| Phosphonic acid and silane SAMs | 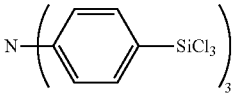 | US20030162053 |
| Triarylamine or polythiophene polymers with conductivity dopants | 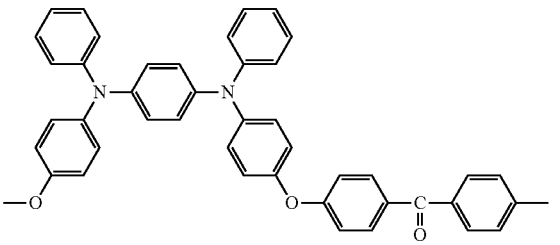 and 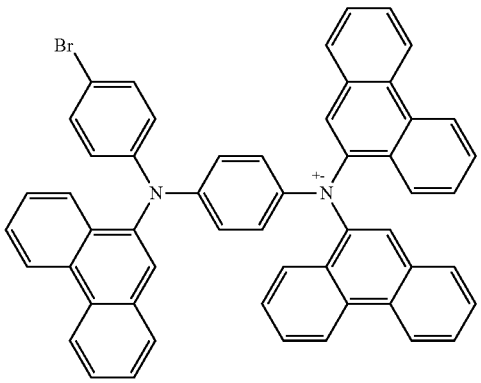 [SMILES: Brc1ccc(N(c2ccc(N(c3cc4ccccc4c4ccccc34)c3cc4ccccc4c4ccccc34)cc2)c2cc3ccccc3c3ccccc23)cc1] | EP1725079A1 |

| MATERIAL | EXAMPLES OF MATERIAL | PUBLICATIONS |
|---|---|---|
| | 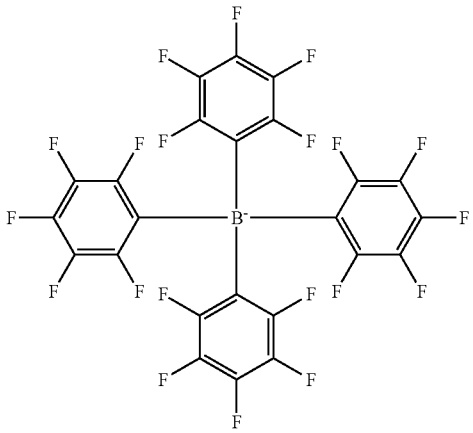 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 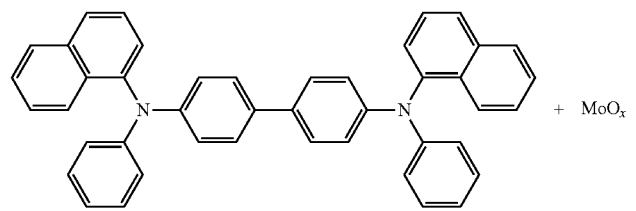 [SMILES: c1ccc(N(c2ccc(-c3ccc(N(c4ccccc4)c4cccc5ccccc45)cc3)cc2)c2cccc3ccccc23)cc1] + MoO$_x$ | US20050123751 SID Symposium Digest, 37, 923 (2006) WO2009018009 |
| n-type semiconducting organic complexes | 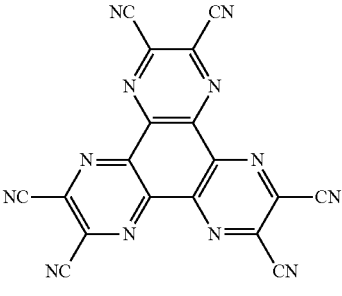 [SMILES: N#Cc1nc2c3nc(C#N)c(C#N)nc3c3nc(C#N)c(C#N)nc3c2nc1C#N] | US20020158242 |
| Metal organometallic complexes | 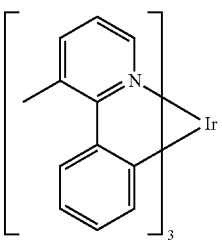 | US20060240279 |

TABLE A-continued

| MATERIAL | EXAMPLES OF MATERIAL | PUBLICATIONS |
| --- | --- | --- |
| Cross-linkable compounds | | US20080220265 |
| Polythiophene based polymers and copolymers | | WO 2011075644<br>EP2350216 |
| Hole transporting materials | | |
| Triarylamines (e.g., TPD, α-NPD) | | Appl. Phys. Lett. 51, 913 (1987) |
| | | U.S. Pat. No. 5,061,569 |

TABLE A-continued
| MATERIAL | EXAMPLES OF MATERIAL | PUBLICATIONS |
|---|---|---|
| | 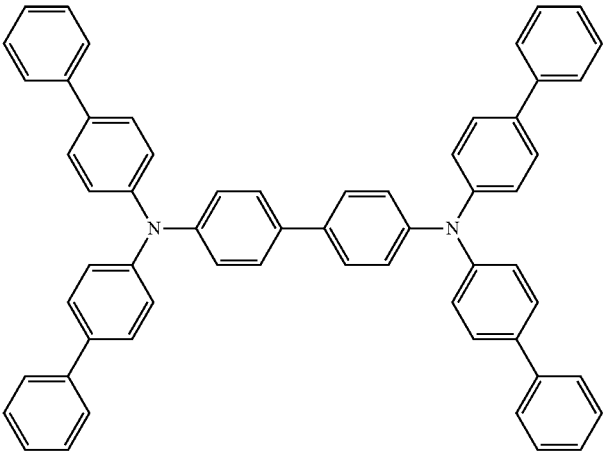 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 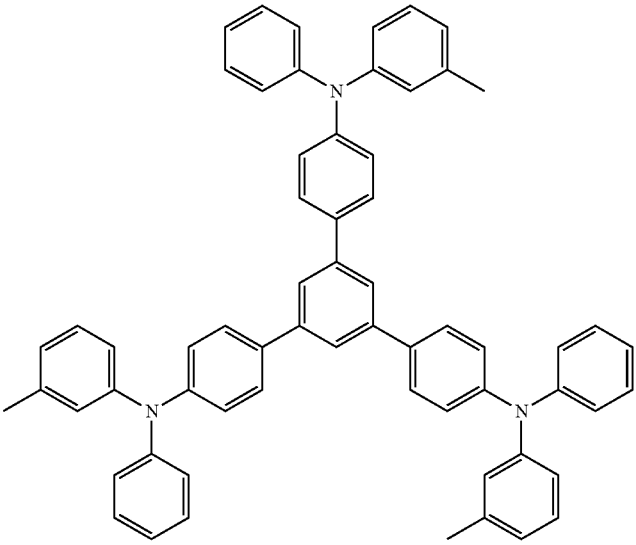 [SMILES: Cc1cccc(N(c2ccccc2)c2ccc(-c3cc(-c4ccc(N(c5ccccc5)c5cccc(C)c5)cc4)cc(-c4ccc(N(c5ccccc5)c5cccc(C)c5)cc4)c3)cc2)c1] | J. Mater. Chem. 3, 319 (1993) |
| | 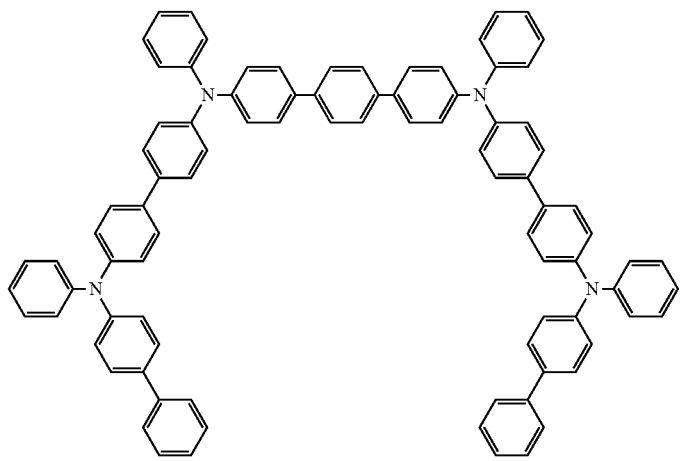 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE A-continued

| MATERIAL | EXAMPLES OF MATERIAL | PUBLICATIONS |
|---|---|---|
|  |  | Appl. Phys. Lett. 90, 183503 (2007) |
| Triarylamine on spirofluorene core |  | Synth. Met. 91, 209 (1997) |
| Arylamine carbazole compounds |  | Adv. Mater. 6, 677 (1994), US20080124572 |
| Triarylamine with (di)benzothiophene/ (di)benzofuran |  | US20070278938, US20080106190 US20110163302 |

| MATERIAL | EXAMPLES OF MATERIAL | PUBLICATIONS |
|---|---|---|
| Indolocarbazoles | 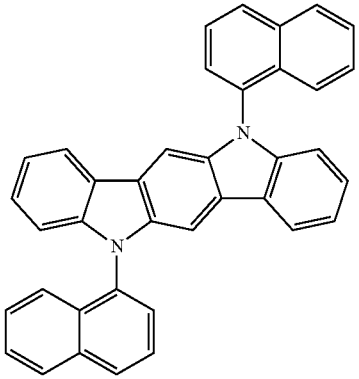 [SMILES: c1ccc2c(-n3c4ccccc4c4cc5c(cc43)c3ccccc3n5-c3cccc4ccccc34)cccc2c1] | Synth. Met. 111, 421 (2000) |
| Isoindole compounds | 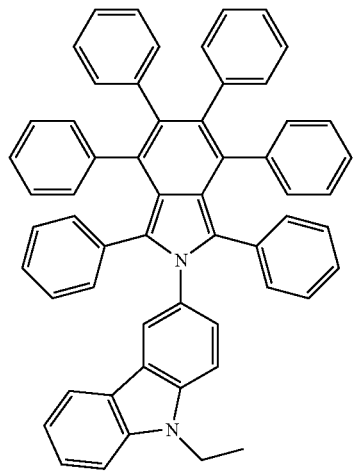 [SMILES: CCn1c2ccccc2c2cc(-n3c(-c4ccccc4)c4c(-c5ccccc5)c(-c5ccccc5)c(-c5ccccc5)c(-c5ccccc5)c4c3-c3ccccc3)ccc21] | Chem. Mater. 15, 3148 (2003) |
| Metal carbene complexes | 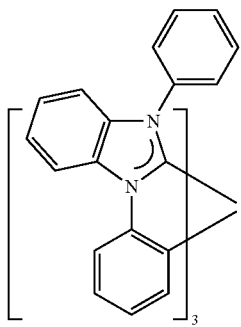 | US20080018221 |
Phosphorescent OLED host materials
Red hosts
| | | |
|---|---|---|
| Arylcarbazoles | 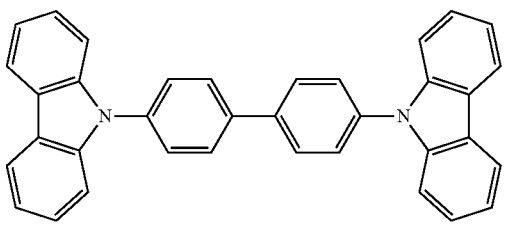 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |

TABLE A-continued

| MATERIAL | EXAMPLES OF MATERIAL | PUBLICATIONS |
|---|---|---|
| Metal 8-hydroxyquinolates (e.g., Alq₃, BAlq) | | Nature 395, 151 (1998) |
| | | US20060202194 |
| | | WO2005014551 |
| | | WO2006072002 |
| Metal phenoxy-benzothiazole compounds | | Appl. Phys. Lett. 90, 123509 (2007) |
| Conjugated oligomers and polymers (e.g., polyfluorene) | | Org. Electron. 1, 15 (2000) |
| Aromatic fused rings | | WO2009066779, WO2009066778, WO2009063833, US20090045731, US20090045730, WO2009008311, US20090008605, US20090009065 |

TABLE A-continued

| MATERIAL | EXAMPLES OF MATERIAL | PUBLICATIONS |
| --- | --- | --- |
| Zinc complexes | | WO2010056066 |
| Chrysene based compounds | | WO2011086863 |
| Green hosts | | |
| Arylcarbazoles | | Appl. Phys. Lett. 78, 1622 (2001) |
| | | US20030175553 |
| | | WO2001039234 |
| Aryltriphenylene compounds | | US20060280965 |

| MATERIAL | EXAMPLES OF MATERIAL | PUBLICATIONS |
|---|---|---|
| | 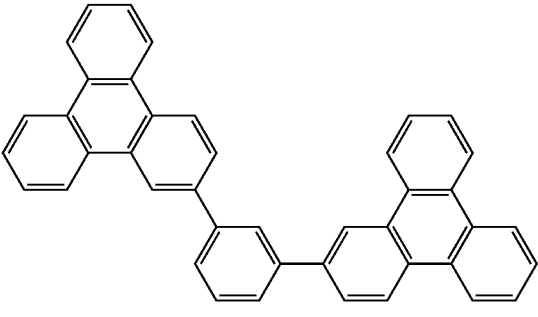 [SMILES: c1cc(-c2ccc3c4ccccc4c4ccccc4c3c2)cc(-c2ccc3c4ccccc4c4ccccc4c3c2)c1] | US20060280965 |
| | 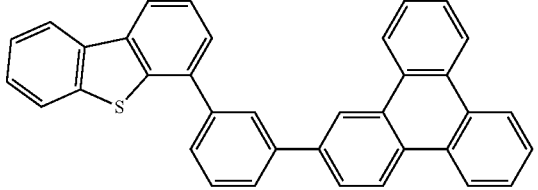 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 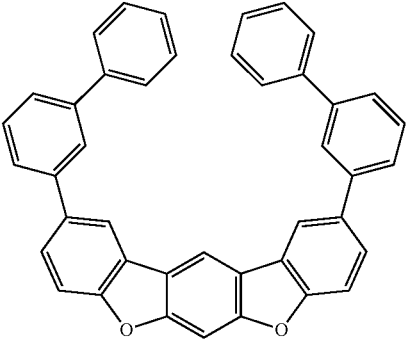 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 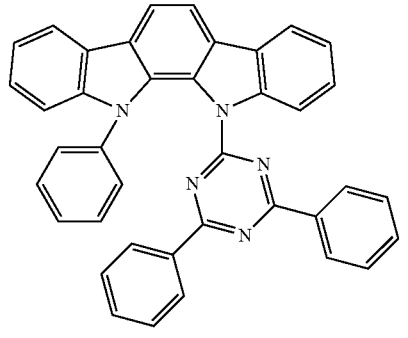 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 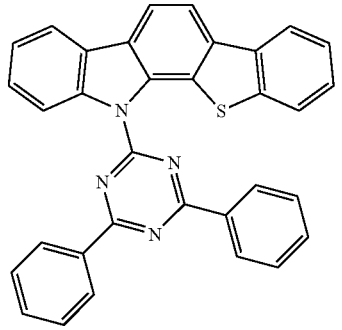 [SMILES: c1ccc(-c2nc(-c3ccccc3)nc(-n3c4ccccc4c4ccc5c6ccccc6sc5c43)n2)cc1] | WO2010107244 |

TABLE A-continued
| MATERIAL | EXAMPLES OF MATERIAL | PUBLICATIONS |
|---|---|---|
| Aza-carbazole/DBT/ DBF | 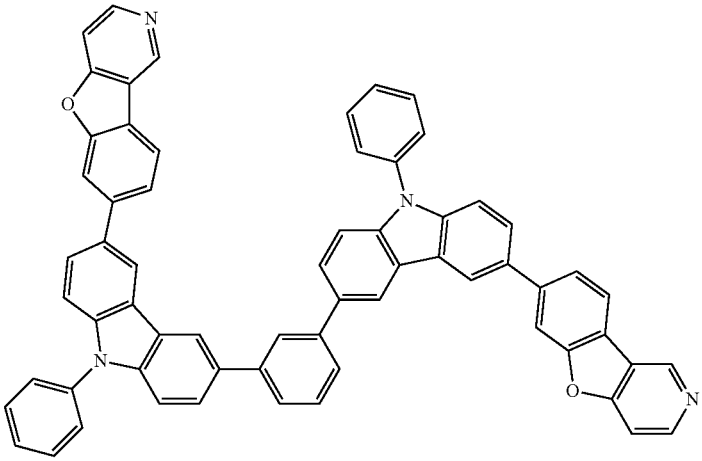 [SMILES: c1ccc(-n2c3ccc(-c4cccc(-c5ccc6c(c5)c5cc(-c7ccc8c(c7)oc7ccncc78)ccc5n6-c5ccccc5)c4)cc3c3cc(-c4ccc5c(c4)oc4ccncc45)ccc32)cc1] | JP2008074939 |
| | 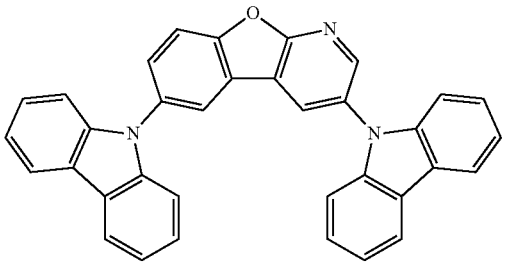 [SMILES: c1ccc2c(c1)c1ccccc1n2-c1ccc2oc3ncc(-n4c5ccccc5c5ccccc54)cc3c2c1] | US20100187984 |
| Polymers (e.g., PVK) | 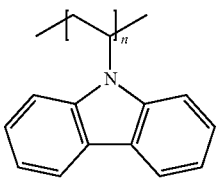 | Appl. Phys. Lett. 77, 2280 (2000) |
| Spirofluorene compounds | 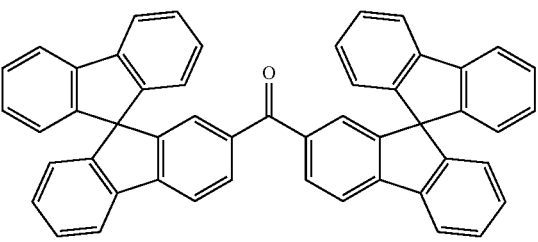 [SMILES: O=C(c1ccc2c(c1)C1(c3ccccc3-c3ccccc31)c1ccccc1-2)c1ccc2c(c1)C1(c3ccccc3-c3ccccc31)c1ccccc1-2] | WO2004093207 |
| Metal phenoxy-benzooxazole compounds | 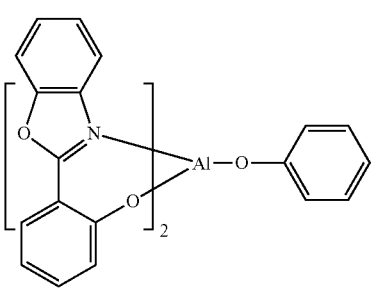 | WO2005089025 |

TABLE A-continued
| MATERIAL | EXAMPLES OF MATERIAL | PUBLICATIONS |
|---|---|---|
| | 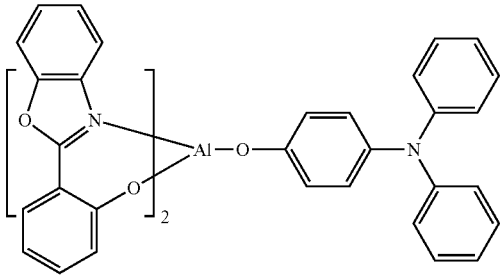 | WO2006132173 |
| | 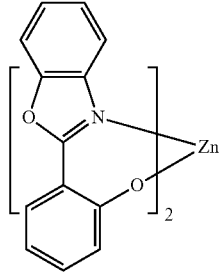 | JP200511610 |
| Spirofluorene-carbazole compounds | 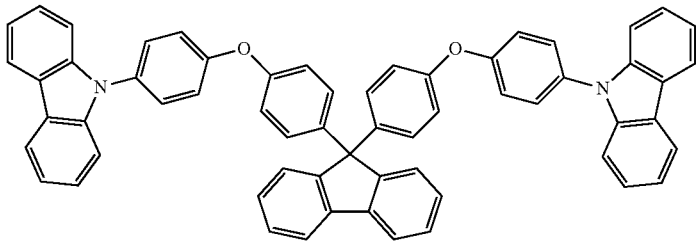 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 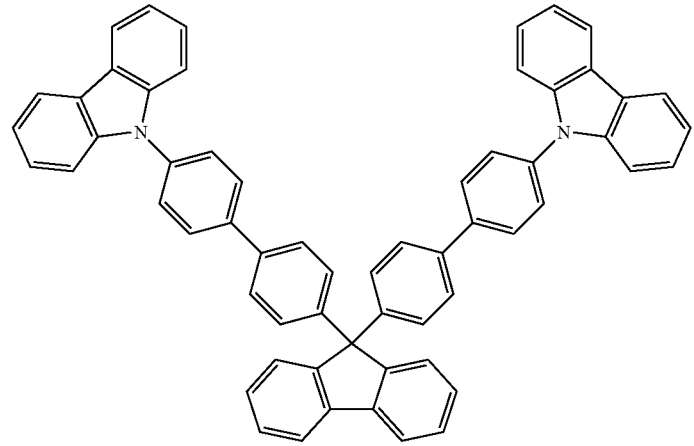 [SMILES: c1ccc2c(c1)-c1ccccc1C2(c1ccc(-c2ccc(-n3c4ccccc4c4ccccc43)cc2)cc1)c1ccc(-c2ccc(-n3c4ccccc4c4ccccc43)cc2)cc1] | JP2007254297 |
| Indolocarbazoles | 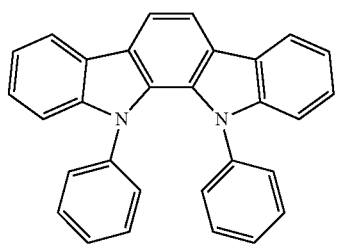 [SMILES: c1ccc(-n2c3ccccc3c3ccc4c5ccccc5n(-c5ccccc5)c4c32)cc1] | WO2007063796 |

| MATERIAL | EXAMPLES OF MATERIAL | PUBLICATIONS |
|---|---|---|
| | 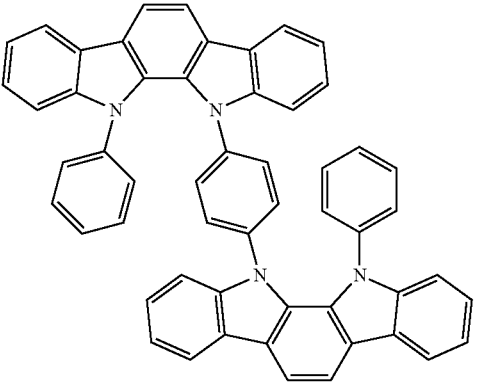 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 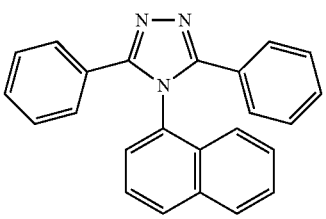 [SMILES: c1ccc(-c2nnc(-c3ccccc3)n2-c2cccc3ccccc23)cc1] | J. Appl. Phys. 90, 5048 (2001) |
| | 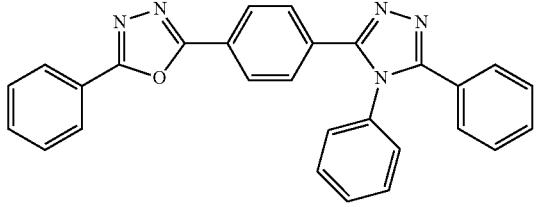 [SMILES: c1ccc(-c2nnc(-c3ccc(-c4nnc(-c5ccccc5)n4-c4ccccc4)cc3)o2)cc1] | WO2004107822 |
| Tetraphenylene complexes | 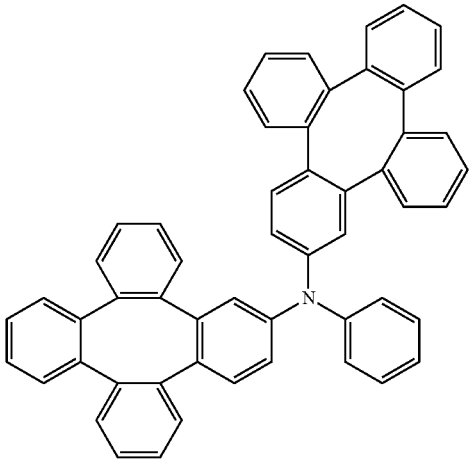 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxy pyridine compounds | 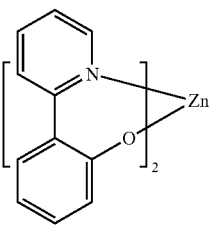 | WO200503900 |

TABLE A-continued

| MATERIAL | EXAMPLES OF MATERIAL | PUBLICATIONS |
| --- | --- | --- |
| Metal coordination complexes (e.g., Zn, Al with N^N ligands) | | US20040137268, US20040137267 |

Blue hosts

| MATERIAL | EXAMPLES OF MATERIAL | PUBLICATIONS |
| --- | --- | --- |
| Arylcarbazoles | | Appl. Phys. Lett. 82, 2422 (2003) |
| | | US20070190359 |
| Dibenzothiophene/ Dibenzofuran- carbazole compounds | | WO2006114966, US20090167162 |
| | | US20090167162 |
| | | WO2009086028 |

TABLE A-continued
| MATERIAL | EXAMPLES OF MATERIAL | PUBLICATIONS |
|---|---|---|
| | 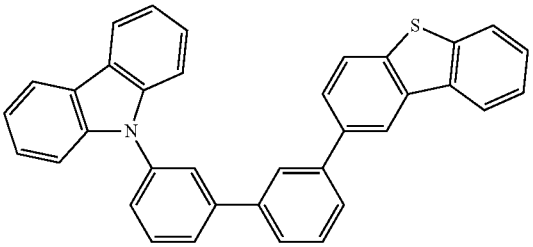 [SMILES: c1cc(-c2cccc(-n3c4ccccc4c4ccccc43)c2)cc(-c2ccc3sc4ccccc4c3c2)c1] | US20090030202, US20090017330 |
| | 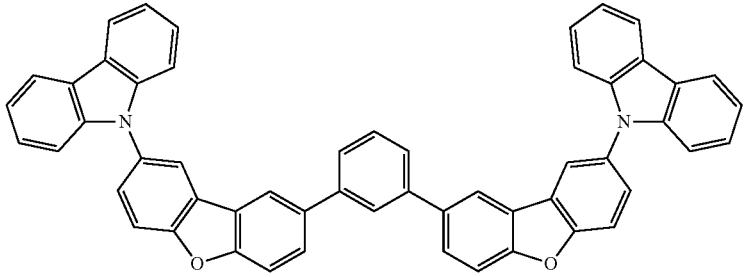 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 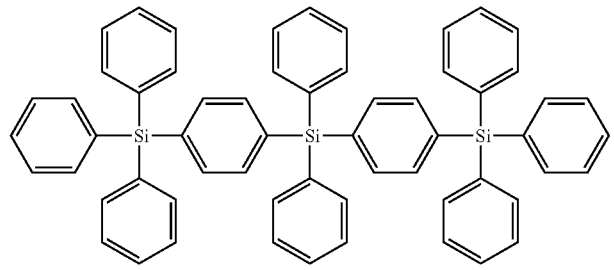 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 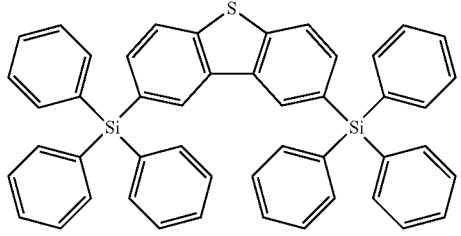 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 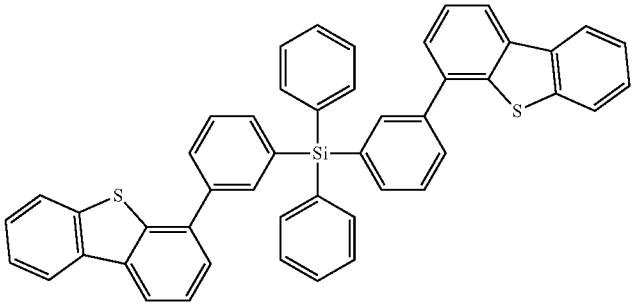 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 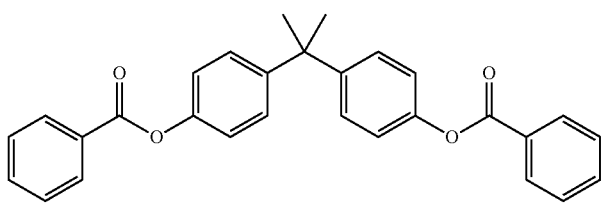 [SMILES: CC(C)(c1ccc(OC(=O)c2ccccc2)cc1)c1ccc(OC(=O)c2ccccc2)cc1] | WO2006100298 |

TABLE A-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium (III) organometallic complexes | | Appl. Phys. Lett. 78, 1622 (2001) |
| | | US20030072964 |

TABLE A-continued

| MATERIAL | EXAMPLES OF MATERIAL | PUBLICATIONS |
|---|---|---|
| | | US20030072964 |
| | | US20060202194 |
| | | US20060202194 |
| | | US20070087321 |
| | | US20080261076<br>US20100090591 |

TABLE A-continued
| MATERIAL | EXAMPLES OF MATERIAL | PUBLICATIONS |
|---|---|---|
| | 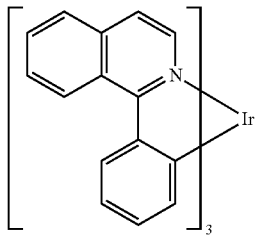 | US20070087321 |
| | 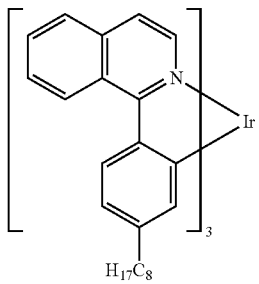 | Adv. Mater. 19, 739 (2007) |
| | 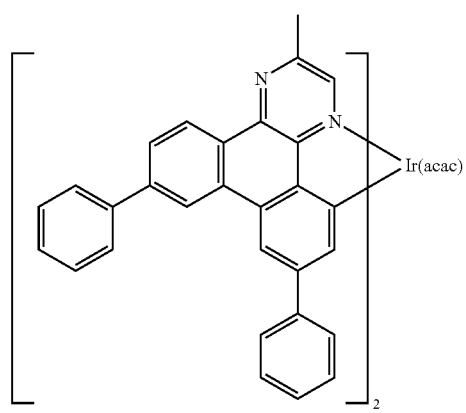 | WO2009100991 |
| | 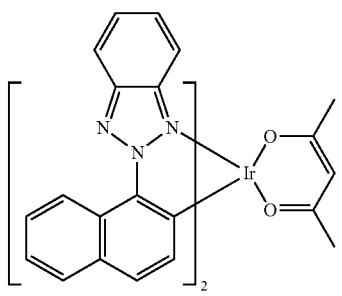 | WO2008101842 |
| | 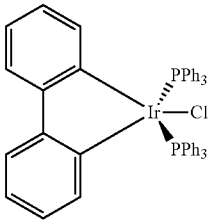 | U.S. Pat. No. 7,232,618 |

TABLE A-continued
| MATERIAL | EXAMPLES OF MATERIAL | PUBLICATIONS |
|---|---|---|
| Platinum (II) organometallic complexes | 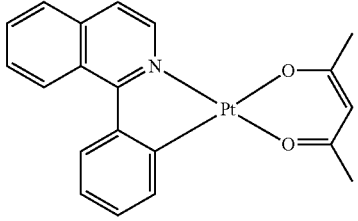 | WO2003040257 |
| | 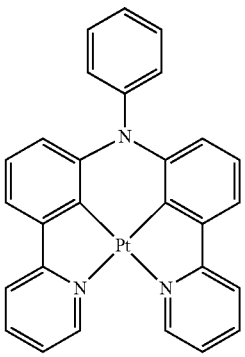 | US20070103060 |
| Osmium (III) complexes | 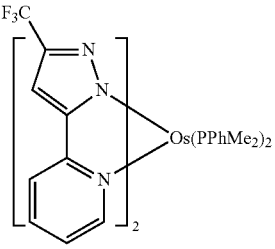 | Chem. Mater. 17, 3532 (2005) |
| Ruthenium (II) complexes | 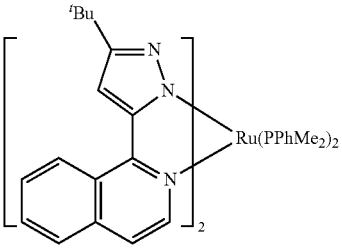 | Adv. Mater. 17, 1059 (2005) |
| Rhenium (I), (II), and (III) complexes | 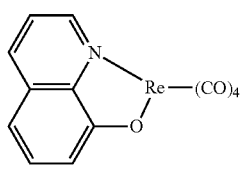 | US20050244673 |
Green dopants TABLE A-continued
| MATERIAL | EXAMPLES OF MATERIAL | PUBLICATIONS |
|---|---|---|
| Iridium (III) organometallic complexes | 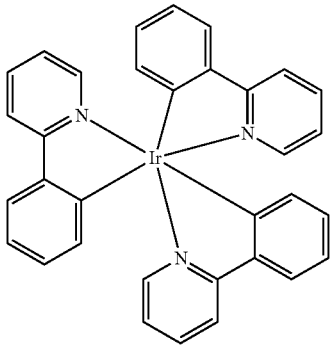<br>and its derivatives | Inorg. Chem. 40, 1704 (2001) |
| | 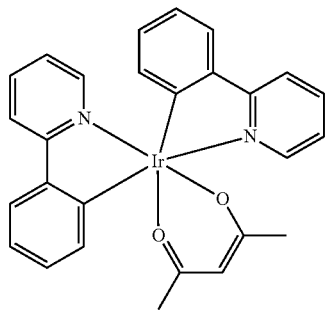 | US20020034656 |
| | 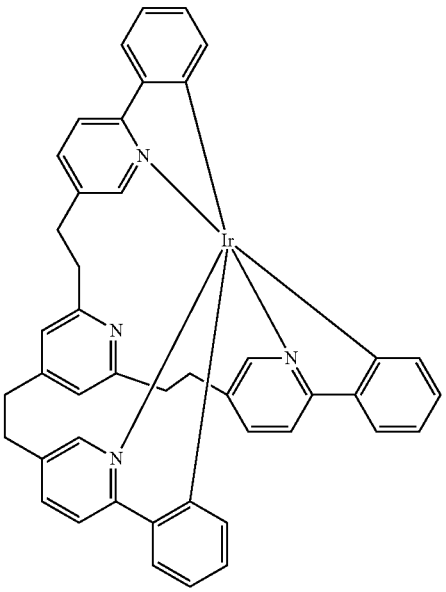 | U.S. Pat. No. 7,332,232 |

TABLE A-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE A-continued

| MATERIAL | EXAMPLES OF MATERIAL | PUBLICATIONS |
|---|---|---|
|  |  | U.S. Pat. No. 6,921,915 |
|  |  | US20100244004 |
|  |  | U.S. Pat. No. 6,687,266 |
|  |  | Chem. Mater. 16, 2480 (2004) |
|  |  | US20070190359 |

TABLE A-continued

| MATERIAL | EXAMPLES OF MATERIAL | PUBLICATIONS |
|---|---|---|
| | | US 20060008670 JP2007123392 |
| | | WO2010086089, US2011044988 |
| | | Adv. Mater. 16, 2003 (2004) |
| | | Angew. Chem. Int. Ed. 2006, 45, 7800 |
| | | WO2009050290 |
| | | US20090165846 |

TABLE A-continued
| MATERIAL | EXAMPLES OF MATERIAL | PUBLICATIONS |
|---|---|---|
| | 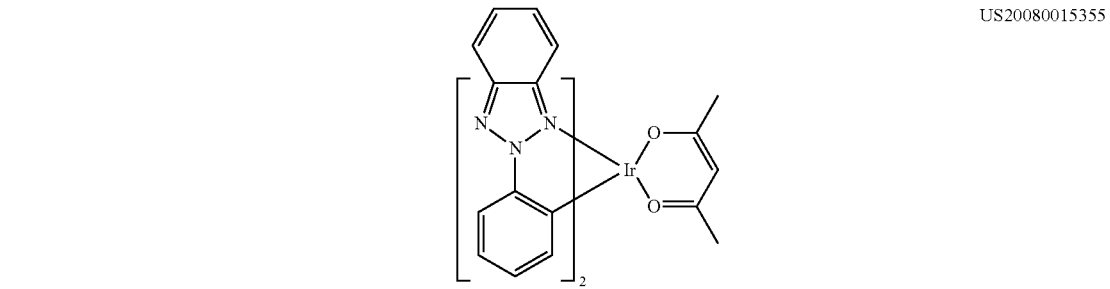 | US20080015355 |
| | 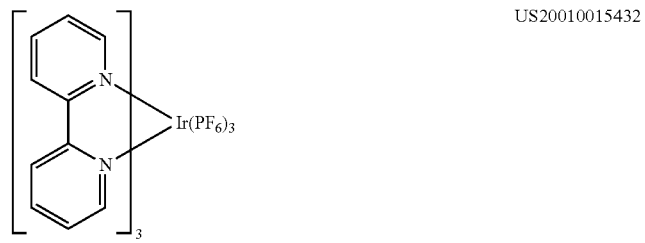 | US20010015432 |
| | 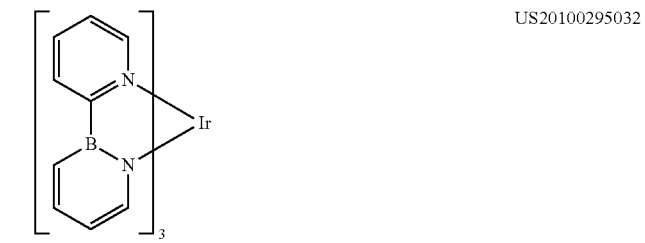 | US20100295032 |
| Monomer for polymeric metal organometallic compounds | 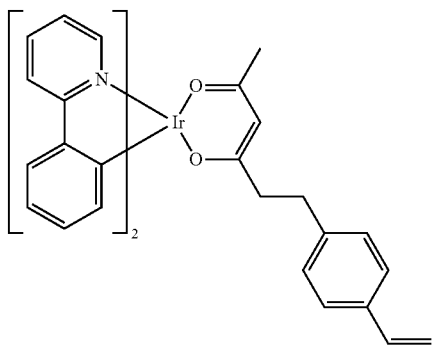 | U.S. Pat. No. 7,250,226, U.S. Pat. No. 7,396,598 |
| Pt (II) organometallic complexes, including polydentated ligands | 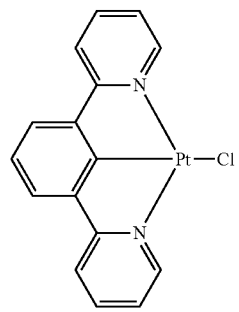 | Appl. Phys. Lett. 86, 153505 (2005) |

| MATERIAL | EXAMPLES OF MATERIAL | PUBLICATIONS |
|---|---|---|
| | 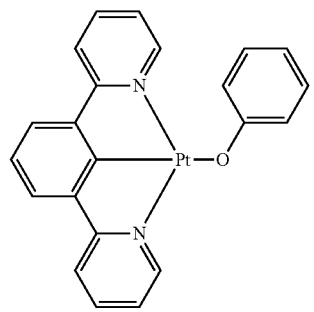 | Appl. Phys. Lett. 86, 153505 (2005) |
| | 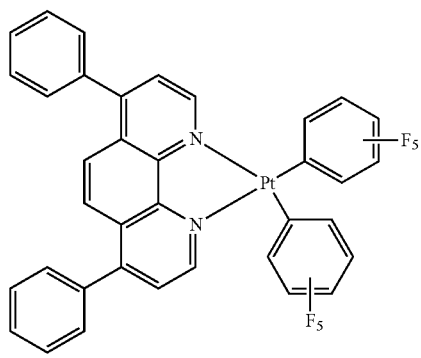 | Chem. Lett. 34, 592 (2005) |
| | 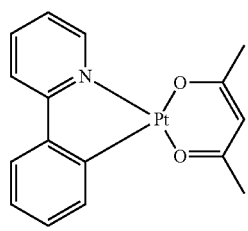 | WO2002015645 |
| | 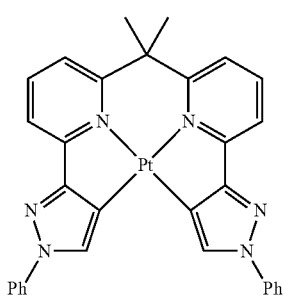 | US20060263635 |
| | 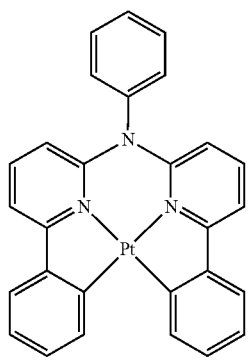 | US20060182992<br>US20070103060 |

TABLE A-continued
| MATERIAL | EXAMPLES OF MATERIAL | PUBLICATIONS |
|---|---|---|
| Cu complexes | 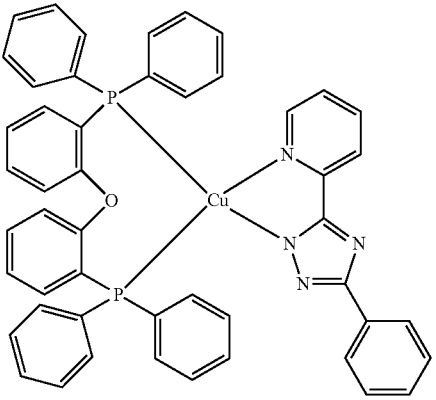 | WO2009000673 |
| | 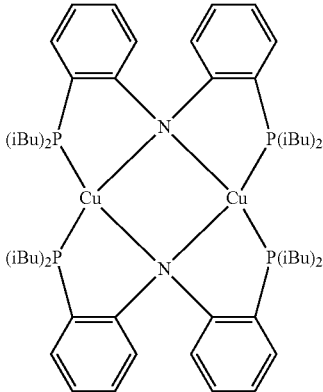 | US20070111026 |
| Gold complexes | 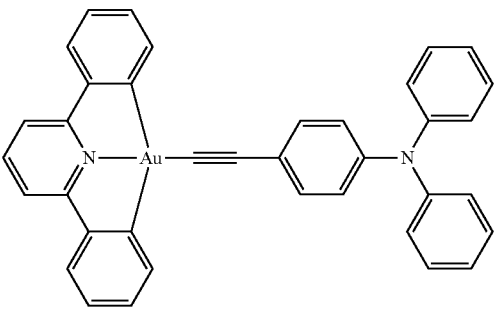 | Chem. Commun. 2906 (2005) |
| Rhenium (III) complexes | 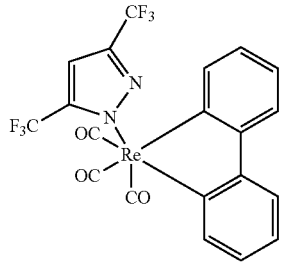 | Inorg. Chem. 42, 1248 (2003) |

TABLE A-continued

| MATERIAL | EXAMPLES OF MATERIAL | PUBLICATIONS |
| --- | --- | --- |
| Osmium (II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

Blue dopants

TABLE A-continued

| MATERIAL | EXAMPLES OF MATERIAL | PUBLICATIONS |
|---|---|---|
| Iridium (III) organometallic complexes | | WO2002002714 |
| | | WO2006009024 |
| | | US20060251923<br>US20110057559<br>US20110204333 |
| | | U.S. Pat. No. 7,393,599,<br>WO2006056418,<br>US20050260441,<br>WO2006019373 |
| | | U.S. Pat. No. 7,534,505 |
| | | WO2011051404 |

TABLE A-continued
| MATERIAL | EXAMPLES OF MATERIAL | PUBLICATIONS |
|---|---|---|
| | 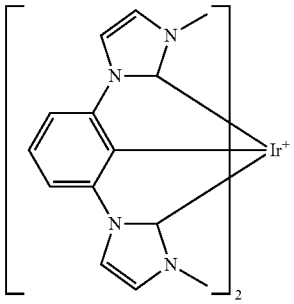 | U.S. Pat. No. 7,445,855 |
| | 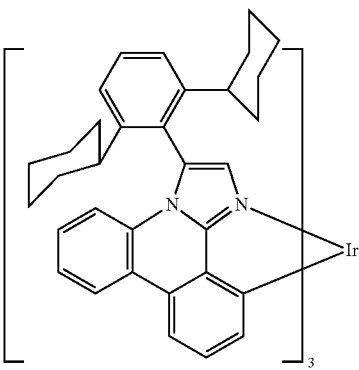 | US20070190359, US20080297033 US20100148663 |
| | 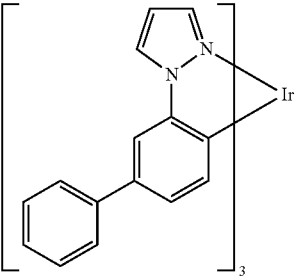 | U.S. Pat. No. 7,338,722 |
| | 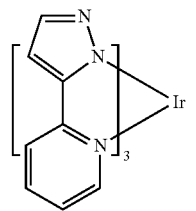 | US20020134984 |
| | 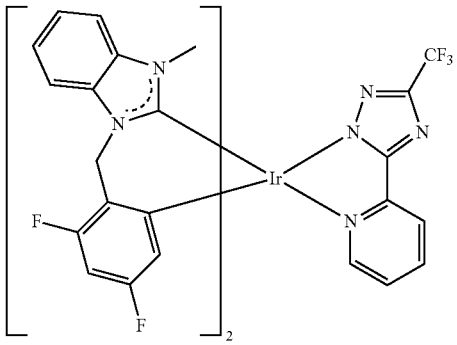 | Angew. Chem. Int. Ed. 47, 4542 (2008) |

TABLE A-continued
| MATERIAL | EXAMPLES OF MATERIAL | PUBLICATIONS |
|---|---|---|
| | 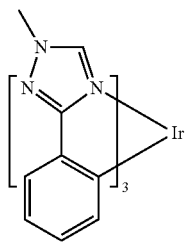 | Chem. Mater. 18, 5119 (2006) |
| | 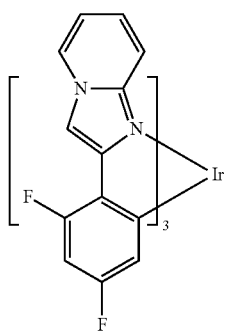 | Inorg. Chem. 46, 4308 (2007) |
| | 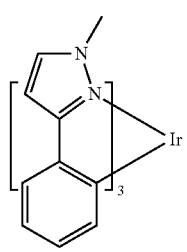 | WO2005123873 |
| | 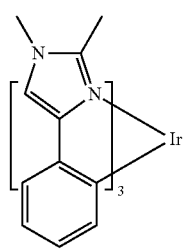 | WO2005123873 |
| | 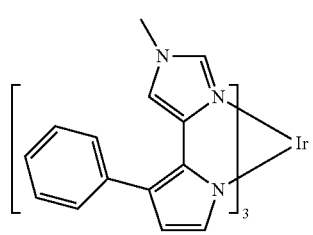 | WO2007004380 |

TABLE A-continued

| MATERIAL | EXAMPLES OF MATERIAL | PUBLICATIONS |
|---|---|---|
| | | WO2006082742 |
| Osmium (II) complexes | | U.S. Pat. No. 7,279,704 |
| | | Organometallics 23, 3745 (2004) |
| Gold complexes | | Appl. Phys. Lett. 74, 1361 (1999) |
| Platinum (II) complexes | | WO2006098120, WO2006103874 |

TABLE A-continued

| MATERIAL | EXAMPLES OF MATERIAL | PUBLICATIONS |
| --- | --- | --- |
| Pt tetradentate complexes with at least one metal-carbene bond | 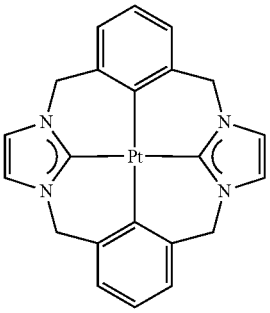 | U.S. Pat. No. 7,655,323 |
| Exciton/hole blocking layer materials | | |
| Bathocuprine compounds (e.g., BCP, BPhen) | 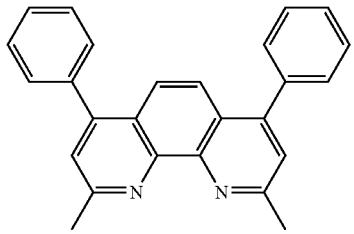 [SMILES: Cc1cc(-c2ccccc2)c2ccc3c(-c4ccccc4)cc(C)nc3c2n1] | Appl. Phys. Lett. 75, 4 (1999) |
| | 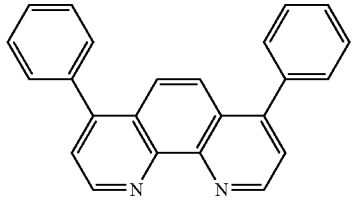 [SMILES: c1ccc(-c2ccnc3c2ccc2c(-c4ccccc4)ccnc23)cc1] | Appl. Phys. Lett. 79, 449 (2001) |
| Metal 8-hydroxyquinolates (e.g., BAlq) | 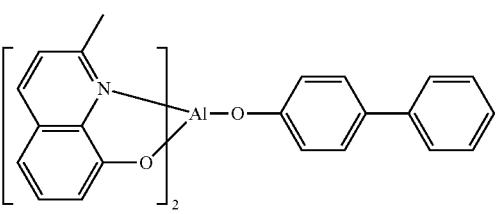 | Appl. Phys. Lett. 81, 162 (2002) |
| 5-membered ring electron deficient heterocycles such as triazole, oxadiazole, imidazole, benzoimidazole | 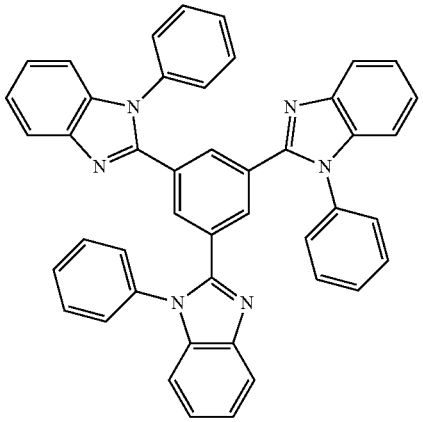 [SMILES: c1ccc(-n2c(-c3cc(-c4nc5ccccc5n4-c4ccccc4)cc(-c4nc5ccccc5n4-c4ccccc4)c3)nc3ccccc32)cc1] | Appl. Phys. Lett. 81, 162 (2002) |

TABLE A-continued

| MATERIAL | EXAMPLES OF MATERIAL | PUBLICATIONS |
| --- | --- | --- |
| Triphenylene compounds | | US20050025993 |
| Fluorinated aromatic compounds | | Appl. Phys. Lett. 79, 156 (2001) |
| Phenothiazine-S-oxide | | WO2008132085 |
| Silylated five-membered nitrogen, oxygen, sulfur or phosphorus dibenzohetereocycles | | WO2010079051 |

TABLE A-continued
| MATERIAL | EXAMPLES OF MATERIAL | PUBLICATIONS |
|---|---|---|
| Aza-carbazoles | 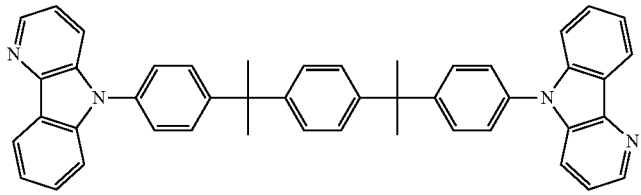 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |乙
| Electron transporting materials | | |
| Anthracene-benzoimidazole compounds | 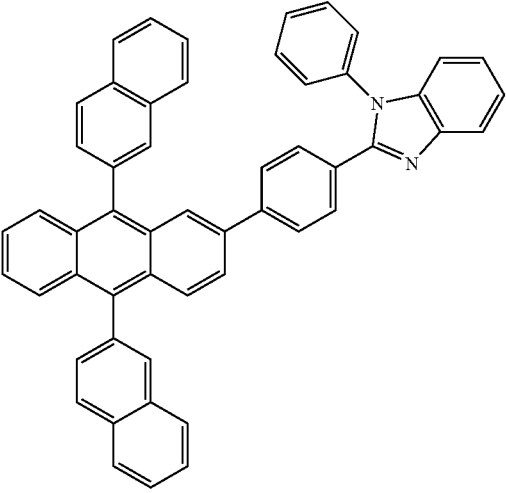 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 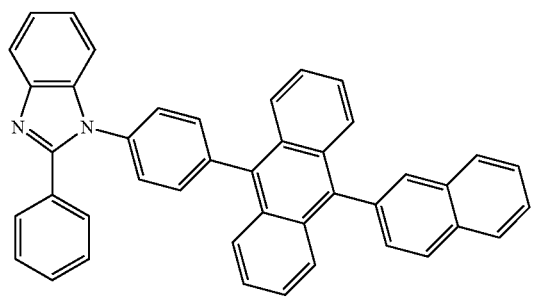 [SMILES: c1ccc(-c2nc3ccccc3n2-c2ccc(-c3c4ccccc4c(-c4ccc5ccccc5c4)c4ccccc34)cc2)cc1] | US20090179554 |
| Aza-triphenylene derivatives | 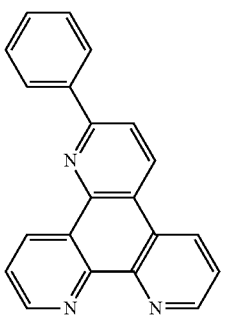 [SMILES: c1ccc(-c2ccc3c4cccnc4c4ncccc4c3n2)cc1] | US20090115316 |
| Anthracene-benzothiazole compounds | 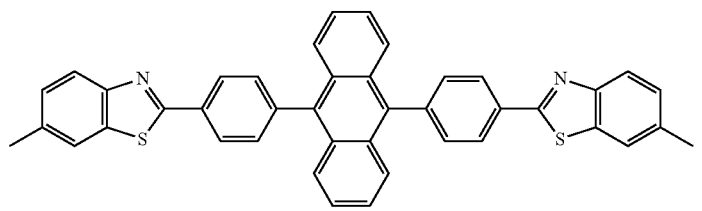 | Appl. Phys. Lett. 89, 063504 (2006) |

TABLE A-continued

| MATERIAL | EXAMPLES OF MATERIAL | PUBLICATIONS |
| --- | --- | --- |
| Metal 8-hydroxy-quinolates (e.g. Alq$_3$, Zrq$_4$) | | Appl. Phys. Lett. 51, 913 (1987)<br>U.S. Pat. No. 7,230,107 |
| Metal hydroxy-benzoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-membered ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE A-continued
| MATERIAL | EXAMPLES OF MATERIAL | PUBLICATIONS |
|---|---|---|
| | 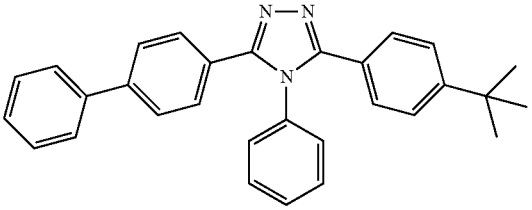 [SMILES: CC(C)(C)c1ccc(-c2nnc(-c3ccc(-c4ccccc4)cc3)n2-c2ccccc2)cc1] | Jpn. J. Apply. Phys. 32, L917 (1993) |
| Silole compounds | 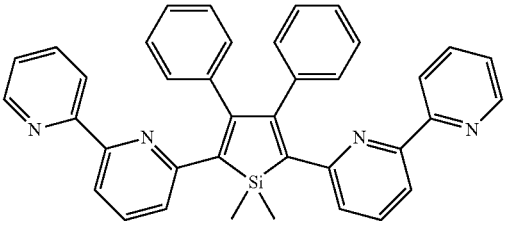 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 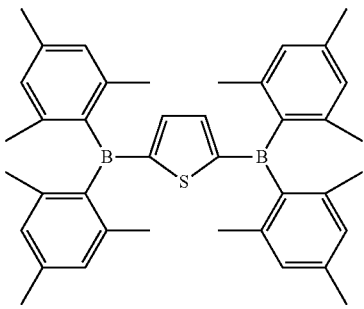 | J. Am. Chem. Soc. 120, 9714 (1998) |
| Fluorinated aromatic compounds | 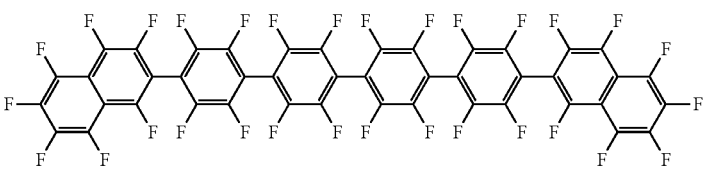 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 122, 1832 (2000) |
| Fullerene (e.g., C60) | 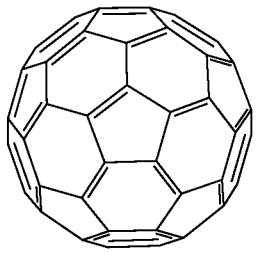 [SMILES: c1cc2c3ccc4c5ccc6c7ccc8c9ccc%10c1c1c2c2c3c4c3c5c6c4c7c8c5c9c%10c1c1c2c3c4c51] | US20090101870 |
| Triazine complexes | 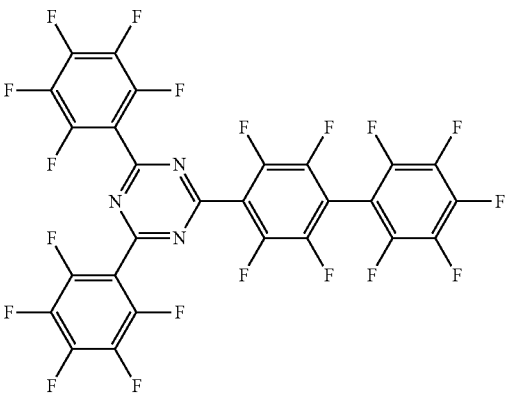 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20040036077 |

TABLE A-continued

| MATERIAL | EXAMPLES OF MATERIAL | PUBLICATIONS |
|---|---|---|
| Zn (N^N) complexes | 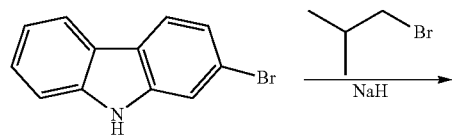 | U.S. Pat. No. 6,528,187 |

EXPERIMENTAL

Material Synthesis

All reactions were carried out under nitrogen protections unless specified otherwise. All solvents for reactions are anhydrous and used as received from commercial sources.

Synthesis of Compound 2,523 [IrL$_{A3}$(L$_{B5}$)$_2$]

Synthesis of 2-bromo-9-isobutyl-9H-carbazole 2-bromo-9H-carbazole (15.0 g, 61.0 mmol) was dissolved in dimethylformamide (DMF) (200 mL) under nitrogen and sodium hydride (6.70 g, 170 mmol) was added in portions then stirred for 15 minutes at room temperature. 1-bromo-2-methylpropane (21.7 g, 160 mmol) was added to the mixture via syringe and the reaction mixture was heated to 60° C. for 4 hours, then left at room temperature overnight. The reaction mixture was concentrated down using a rotary evaporator and the residue was extracted twice with ethyl acetate. The combined organics were washed with brine. The crude material was purified via column chromatography using a heptane/ethyl acetate (90/10) solvent system to obtain 19.0 g of 2-bromo-9-isobutyl-9H-carbazole as a white solid.

Synthesis of 9-isobutyl-2-(4,4,5,5-tetramethyl-1,3,2-dioxaborolan-2-yl)-9H-carbazole 2-bromo-9-isobutyl-9H-carbazole (19.0 g, 62.9 mmol), 4,4,4',4',5,5,5',5'-octamethyl-2,2'-bi(1,3,2-dioxaborolane) (31.9 g, 130 mmol), dicyclohexyl(2',6'-dimethoxy-[1,1'-biphenyl]-3-yl)phosphine (2.07 g, 5.03 mmol), potassium acetate (15.4 g, 160 mmol), and dioxane (500 mL) were mixed in a flask. The mixture was degassed by bubbling with nitrogen gas for 15 minutes, then the reaction mixture was heated to reflux overnight. The reaction mixture was then filtered through Celite and washed well with ethyl acetate to remove a gray precipitate. The filtrate was washed with brine, dried with sodium sulfate, and filtered, then concentrated down to an orange oil. That oil was placed on a Kugelrohr and heated to 180° C. to remove the bis-pinacolate. The crude material was purified via column chromatography using a heptane/dichloromethane (DCM) solvent system (75/25 to 25/75) to obtain 17.46 g of 9-isobutyl-2-(4,4,5,5-tetramethyl-1,3,2-dioxaborolan-2-yl)-9H-carbazole as a white solid for an 80% yield.

153
Synthesis of 9-isobutyl-2-(6-methyl-[2,3'-bipyridin]-6'-yl)-9H-carbazole

154
Synthesis of Compound 2,523

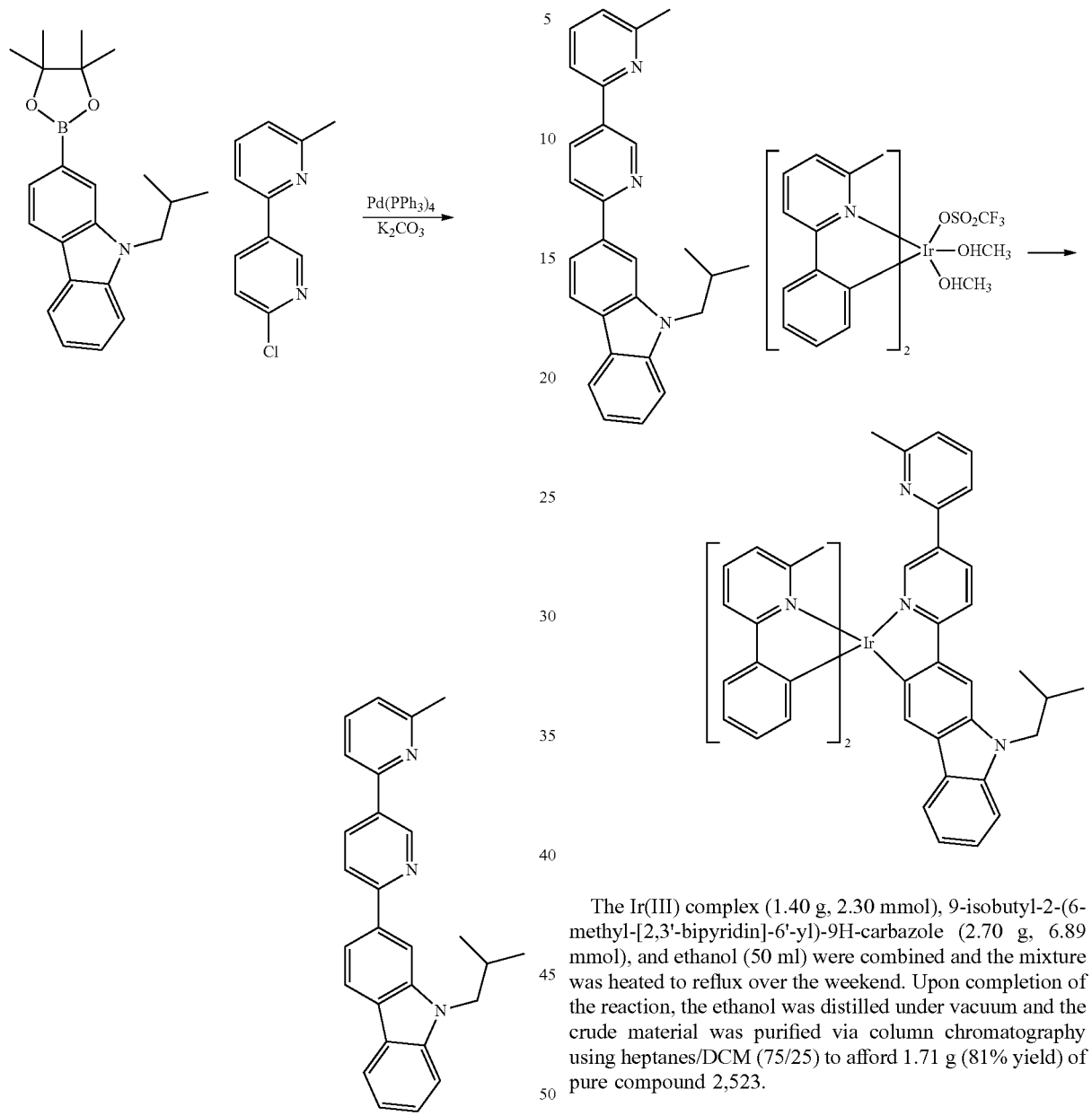

6'-chloro-6-methyl-2,3'-bipyridine (2.50 g, 12.2 mmol), 9-isobutyl-2-(4,4,5,5-tetramethyl-1,3,2-dioxaborolan-2-yl)-9H-carbazole (5.12 g, 14.7 mmol), palladium tetrakis Pd(PPh$_3$)$_4$ (0.42 g, 0.37 mmol), dimethoxyethane (DME) (80 mL), and water (20 mL) were combined in a flask. The mixture was degassed by bubbling with nitrogen gas for 15 minutes, then the reaction mixture was heated to reflux overnight. The reaction mixture was extracted with ethyl acetate and washed with water. The crude material was purified via column chromatography using a DCM/ethyl acetate solvent system (97.5/2.5 to 95/5) to afford a light yellow solid. The product was further purified by reverse phase (C18) chromatography using acetonitrile and water (90/10) to afford 3.92 (83% yield) of 9-isobutyl-2-(6-methyl-[2,3'-bipyridin]-6'-yl)-9H-carbazole as a pale yellow solid.

The Ir(III) complex (1.40 g, 2.30 mmol), 9-isobutyl-2-(6-methyl-[2,3'-bipyridin]-6'-yl)-9H-carbazole (2.70 g, 6.89 mmol), and ethanol (50 ml) were combined and the mixture was heated to reflux over the weekend. Upon completion of the reaction, the ethanol was distilled under vacuum and the crude material was purified via column chromatography using heptanes/DCM (75/25) to afford 1.71 g (81% yield) of pure compound 2,523.

Synthesis of Compound 26,471 [Ir(L$_{A11}$)$_2$L$_{C2}$]

Synthesis of 4-chloro-2-methyl-2'-nitro-1,1'-biphenyl

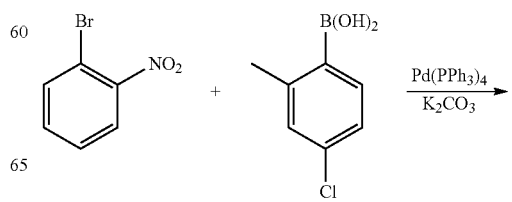

-continued

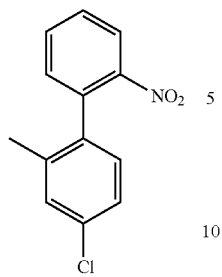

1-bromo-2-nitrobenzene (20.0 g, 99 mmol), (4-chloro-2-methylphenyl)boronic acid (18.6 g, 110 mmol), potassium carbonate (34.2 g, 250 mmol), palladium tetrakis (3.43 g, 2.97 mmol), DME (400 ml), and water (100 ml) were combined in a round bottom flask. The mixture was degassed by bubbling with nitrogen gas for 15 minutes, then the reaction was heated to reflux overnight. Upon completion, the reaction mixture was extracted with ethyl acetate three times and the organic layer was washed with brine twice, dried with sodium sulfate, filtered, and concentrated down to a brown oil. The crude material was purified with silica gel using a heptane/DCM (75/25) solvent system to isolate 23.2 g (95% yield) of 4-chloro-2-methyl-2'-nitro-1,1'-biphenyl as a yellow oil.

Synthesis of 2-chloro-4-methyl-9H-carbazole

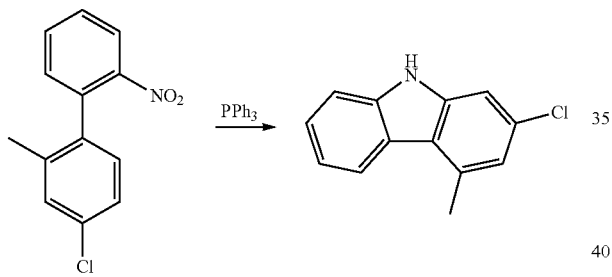

4-chloro-2-methyl-2'-nitro-1,1'-biphenyl (23.2 g, 94 mmol), triphenylphosphine (73.7 g, 280 mmol), and 1,2 dichlorobenzene (450 ml) were combined in a round bottom flask. A condenser was attached, then the system was evacuated and purged with nitrogen three times. The reaction mixture was heated to reflux overnight. Upon completion, the dichlorobenzene was removed by Kugelrohr at 110° C. The crude product was purified by filtering through a silica gel plug using a heptanes/ethyl acetate (100/0 to 90/10) solvent system. The sample was purified via column chromatography using a heptane/ethyl acetate (95/5 to 90/10) solvent system to obtain 18.0 g of 2-chloro-4-methyl-9H-carbazole as a beige solid for a 89% yield.

Synthesis of 2-chloro-9-isobutyl-4-methyl-9H-carbazole

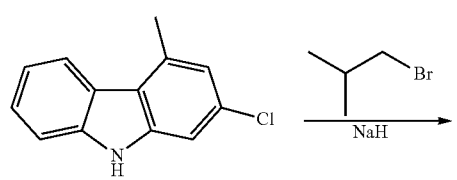

2-chloro-4-methyl-9H-carbazole (9.00 g, 41.7 mmol) was dissolved in DMF (150 ml) in a round bottom flask and placed under nitrogen. Sodium hydride (2.50 g, 62.6 mmol) was added in portions then stirred for 15 minutes after addition was complete. 1-bromo-2-methylpropane (6.81 ml, 62.6 mmol) was added and the reaction mixture was heated to 60° C. for 4 hours, then stirred at room temperature overnight. The reaction mixture was concentrated down on a rotovap then transferred to separatory funnel, extracted with ethyl acetate, and washed water. The organics were washed once with water and twice with brine, then dried with sodium sulfate, filtered, and concentrated down. The brown solid was purified via column chromatography using Heptanes/Ethyl Acetate (95/5) solvent system to obtain 9.1 g of 2-chloro-9-isobutyl-4-methyl-9H-carbazole as a white solid for an 80% yield.

Synthesis of 9-isobutyl-4-methyl-2-(4,4,5,5-tetramethyl-1,3,2-dioxaborolan-2-yl)-9H-carbazole

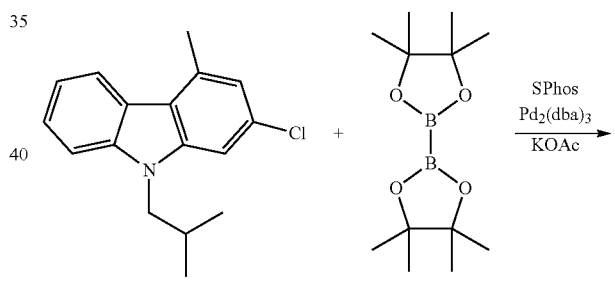

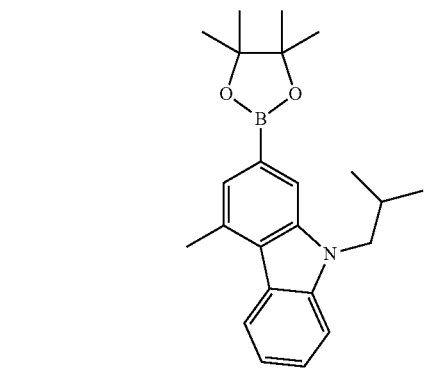

2-chloro-9-isobutyl-4-methyl-9H-carbazole (9.00 g, 33.1 mmol), 4,4,4',4',5,5,5',5'-octamethyl-2,2'-bi(1,3,2-dioxaborolane) (16.8 g, 66.2 mmol), dicyclohexyl(2',6'-dimethoxy-[1,1'-biphenyl]-3-yl)phosphine (1.09 g, 2.65 mmol), potassium acetate (8.12 g, 83.0 mmol), and dioxane (200 mL) were combined in a round bottom flask. The mixture was degassed by bubbling with nitrogen gas for 15 minutes, then the reaction mixture was heated to reflux overnight. The reaction mixture was then filtered through a Celite plug and washed with ethyl acetate. The filtrate was washed twice with brine, dried with sodium sulfate, filtered, and then concentrated down. The oil was purified using a Kugelrohr apparatus at 180° C. to remove the bis-pinacolate. The dark brown solid was dissolved in DCM, filtered through a Celite plug then concentrated down. The brown solid was purified via column chromatography using heptane/DCM (75/25 to 25/75) solvent system to obtain 10.3 g of 9-isobutyl-4-methyl-2-(4,4,5,5-tetramethyl-1,3,2-dioxaborolan-2-yl)-9H-carbazole as a white solid for an 86% yield.

Synthesis of 9-isobutyl-4-methyl-2-(6-methyl-[2,3'-bipyridin]-6'-yl)-9H-carbazole

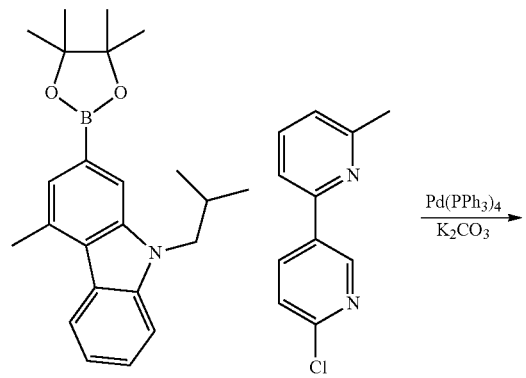

-continued

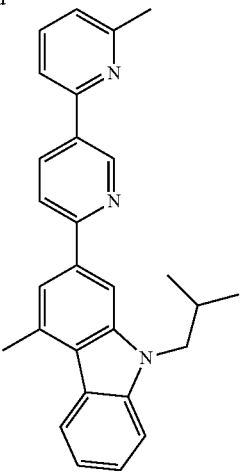

6'-chloro-6-methyl-2,3'-bipyridine (3.20 g, 15.6 mmol), 9-isobutyl-4-methyl-2-(4,4,5,5-tetramethyl-1,3,2-dioxaborolan-2-yl)-9H-carbazole (6.25 g, 17.2 mmol), palladium tetrakis (0.542 g, 0.469 mmol), DME (120 mL) and water (30 mL) were combined in a round bottom flask. The mixture was degassed by bubbling nitrogen gas for 15 minutes and the reaction was heated to reflux overnight. Upon completion, the reaction was extracted using ethyl acetate, washed with water and Brine, dried with sodium sulfate, filtered through Celite then concentrated down to an orange oil. The crude material was purified via column chromatography using a DCM/ethyl acetate (100/0 to 85/15) solvent system. The isolated product was further purified by reverse phase chromatography using an acetonitrile/water (85/15 to 100/0) solvent system to isolate 4.2 g (66% yield) of 9-isobutyl-4-methyl-2-(6-methyl-[2,3'-bipyridin]-6'-yl)-9H-carbazole as an off white solid.

Synthesis of the Ir(III) Dimer

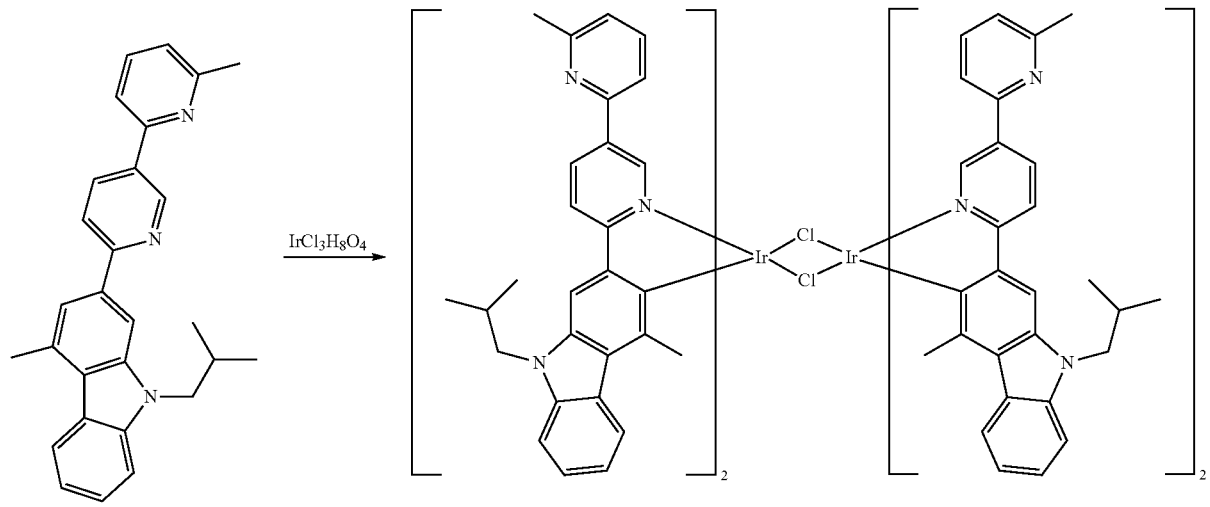

9-isobutyl-4-methyl-2-(6-methyl-[2,3'-bipyridin]-6'-yl)-9H-carbazole (4.23 g, 10.4 mmol) was placed in a round bottom flask (RBF) and solubilized in ethoxythanol (35 mL) and water (12 mL). The mixture was degassed by bubbling with nitrogen gas for 15 minutes and then iridium chloride (1.03 g, 2.78 mmol) was added and the reaction mixture was heated at 105° C. for 24 hours. The reaction mixture was cooled down to room temperature, diluted with 10 mL of MeOH, filtered and washed with MeOH. The Ir(III) Dimer (3.2 g, 111% yield) was isolated.

Synthesis of Compound 26,471

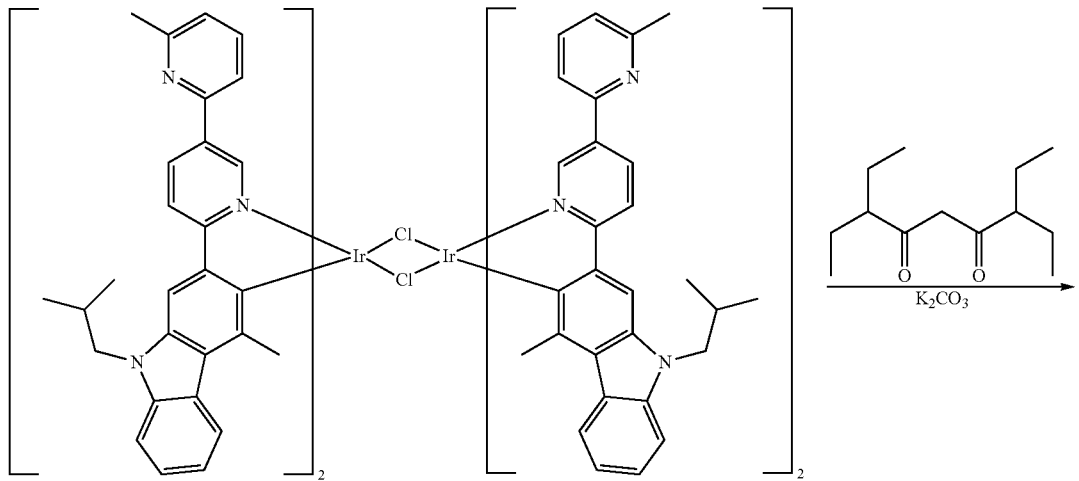

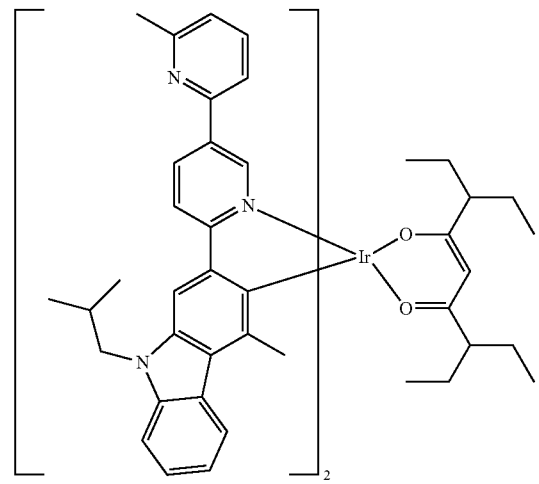

The Ir(III) Dimer (1.60 g, 0.77 mmol), 3,7-diethylnonane-4,6-dione (1.64 g, 7.72 mmol), and 2-ethoxyethanol (25 ml) were combined and the mixture was degassed by bubbling with nitrogen gas for 15 minutes. Potassium carbonate (1.07 g, 7.72 mmol) was added and the reaction mixture was stirred at room temperature overnight. Upon completion, the reaction mixture was filtered through Celite and washed with DCM. The red product was triturated in heptanes and the red solid was purified via column chromatography (pretreated with triethylamine) using a heptanes/DCM (90/10 to 50/50) solvent system. The combined fraction was concentrated down and the red solid was triturated from methanol to yield 0.65 g (36% yield) of compound 26,471 as a red solid.

Synthesis of Compound 2,740 [IrL$_{A220}$(L$_{B5}$)$_2$]

Synthesis of Compound 2,740

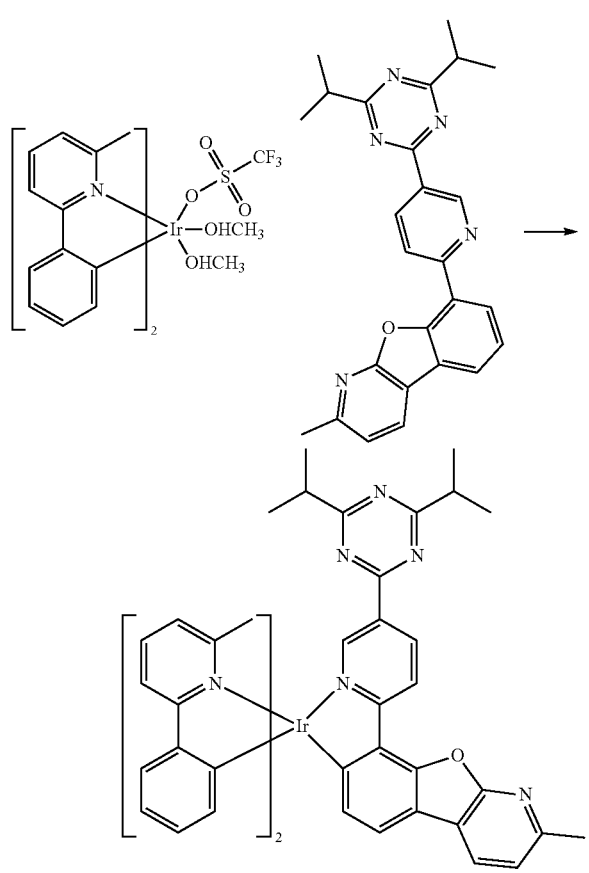

The Ir(III) complex (1.20 g, 1.61 mmol) and 8-(5-(4,6-diisopropyl-1,3,5-triazin-2-yl)pyridin-2-yl)-2-methylbenzofuro[2,3-b]pyridine (2.05 g, 4.84 mmol) were mixed in Ethanol (32 mL). The reaction was heated to reflux overnight. Upon completion of the reaction, orange solid precipitated out of the (mixture. The reaction was filtered over a pad of Celite and washed with methanol until the wash was clear. The filtering flask was then changed and the solids on the Celite were washed with Dichloromethane until the wash was colorless. The crude product was purified via column chromatography using Heptanes/Ethyl Acetate 60/40) solvent system. The collected fractions were combined and the orange product was triturated from Methanol to afford the pure emitter (1.20 g, 78% yield).

Synthesis of Compound 21,010 [IrL$_{A220}$(L$_{B34}$)$_2$]

Synthesis of Compound 21,010

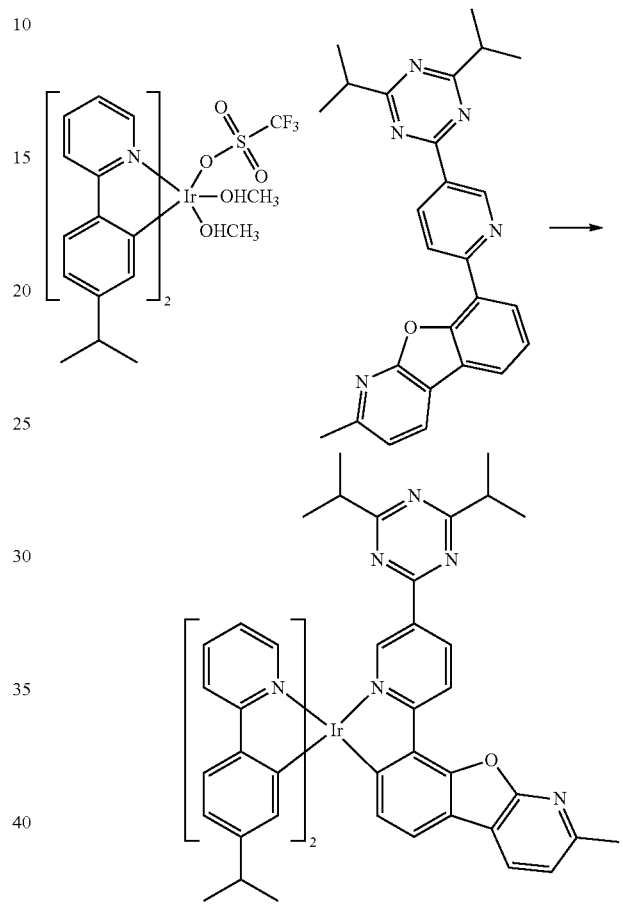

Ir(III) complex (0.90 g, 1.13 mmol) and 8-(5-(4,6-diisopropyl-1,3,5-triazin-2-yl)pyridin-2-yl)-2-methylbenzofuro[2,3-b]pyridine (1.43 g, 3.38 mmol) were mixed in Ethanol (23 mL). The reaction was heated to gentle reflux overnight. Upon completion of the reaction, orange solid precipitated out of the mixture. The reaction was filtered over a pad of Celite and washed with methanol until the wash was clear. The filtering flask was then changed and the solids on the Celite were washed with Dichloromethane until the wash was colorless. The crude product was purified via column chromatography using DCM/Ethyl Acetate (100/0 to 98/2) solvent system. The collected fractions were combined and the orange product was triturated from Methanol to afford the pure dopant (0.48 g, 42% yield).

Device Examples

All example devices were fabricated by high vacuum (<10$^{-7}$ Torr) thermal evaporation. The anode electrode was 1200 Å of indium tin oxide (ITO). The cathode consisted of 10 Å of LiF followed by 1,000 Å of Al. All devices were encapsulated with a glass lid sealed with an epoxy resin in a nitrogen glove box (<1 ppm of H$_2$O and O$_2$) immediately after fabrication, and a moisture getter was incorporated inside the package. The organic stack of the device examples consisted of sequentially, from the ITO surface, 100 Å of LG101 (purchased from LG chem) as the hole injection layer (HIL); 400 Å of 4,4'-bis[N-(1-naphthyl)-N-phenylamino]biphenyl (NPD) as the hole transporting layer (HTL); 300 Å of an emissive layer (EML) containing Compound H as a host (79%), a stability dopant (SD) (18%), and Compound 401 or Compound 24 as an emitter; 100 Å of Compound H as a blocking layer; and 450 Å of Alq$_3$ (tris-8-hydroxyquinoline aluminum) as the ETL. The emitter was selected to provide the desired color and the stability dopant (SD) was mixed with the electron-transporting host and the emitter to help transport positive charge in the emissive layer. Table 1 shows the composition of the EML in the device, while the device results and data are summarized in Table 2.

As used herein, NPD, compound H, SD, and AlQ$_3$ have the following structures:

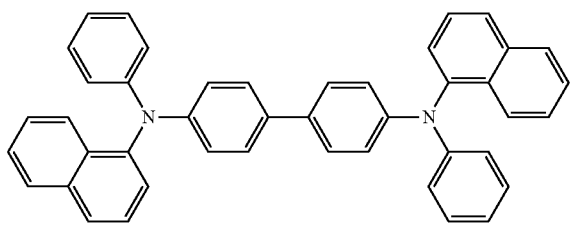
NPD

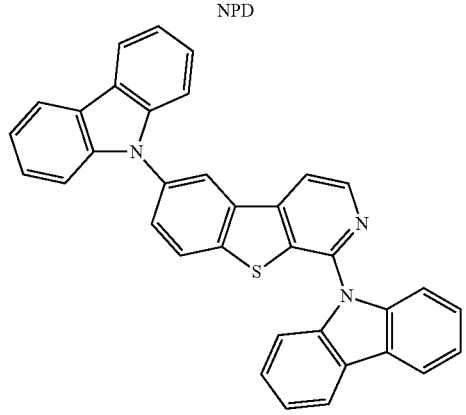
Compound H

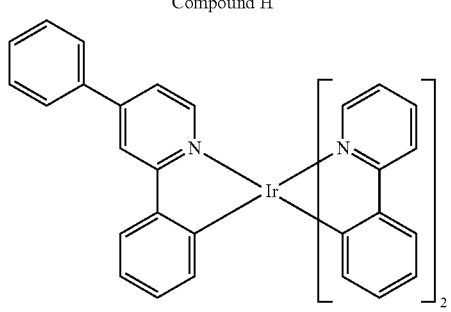
SD

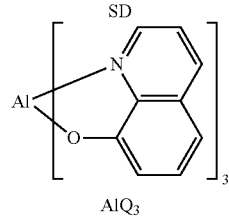
AlQ$_3$

Table 1. Compounds of EML in the Devices

| Example | Emitter |
| --- | --- |
| Device Example 1 | Compound 2,523 |
| Device Example 2 | Compound 26,471 |
| Device Example 3 | Compound 2,740 |
| Device Example 4 | Compound 21,010 |

TABLE 2

Device results of Device examples 1 and 2.

| | 1931 CIE | | λ max | FWHM | EQE at 1,000 nits | LT$_{95\%}$ at 1,000 nits |
| --- | --- | --- | --- | --- | --- | --- |
| | x | y | [nm] | [nm] | [%] | [hours] |
| Device Example 1 | 0.63 | 0.36 | 614 | 81 | 17.0 | 5,500 |
| Device Example 2 | 0.69 | 0.31 | 652 | 70 | 11.0 | 1,000 |
| Device Example 3 | 0.59 | 0.41 | 600 | 74 | 18.7 | 16,600 |
| Device Example 4 | 0.60 | 0.40 | 606 | 81 | 18.1 | 12,700 |

Table 2 summarizes the performance of the devices. The 1931 CIE values were measured at 10 mA/cm$^2$. The luminous efficiency and the lifetime (LT$_{95\%}$) were measured at 1000 cd/m$^2$. The device examples show that combining L$_A$ with either L$_B$ or L$_C$ changes the device properties. L$_B$ combined with L$_A$ tends to provide dopants with broader emission. The broad FWHM is useful for lighting applications. On the other hand, the emission spectrum from dopant based on the combination of L$_A$ and L$_C$ is narrower which helps to provide a better color quality. Therefore, iridium complexes described in this invention provide a broad range of useful materials for both lighting and display applications.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:
1. A compound having a formula $M(L_A)_x(L_B)_y(L_C)_z$:
wherein the ligand $L_A$ is

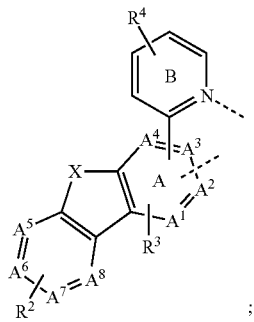

wherein the ligand $L_B$ is

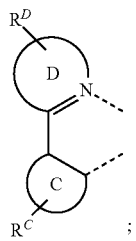

wherein the ligand $L_C$ is

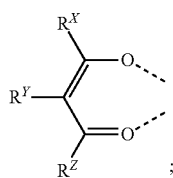

wherein M is a metal having an atomic number greater than 40;
wherein x is 1, or 2;
wherein y is 0, 1, or 2;
wherein z is 0, 1, or 2;
wherein x+y+z is the oxidation state of the metal M;
wherein $A^1$, $A^2$, $A^3$, $A^4$, $A^5$, $A^6$, $A^7$, and $A^8$ are carbon or nitrogen;
wherein ring B is bonded to ring A through a C—C bond;
wherein M is bonded to ring A through an M-C bond;
wherein X is selected from the group consisting of O, S, Se, CRR', and $NR^1$;
wherein rings C and D are each independently a 5 or 6-membered carbocyclic or heterocyclic ring;
wherein $R^3$ represents mono, or di-substitution, or no substitution;
wherein $R^2$, $R^C$, and $R^D$ each independently represent mono, di, tri, or tetra-substitution, or no substitution;
wherein $R^4$ represents mono, di, tri, or tetra-substitution;
wherein at least one $R^4$ is a triazine ring which is further substituted by $R^E$;
wherein $R^E$ represents mono or di-substitution;
wherein each of R, R', $R^1$, $R^2$, $R^3$, $R^4$, $R^C$, $R^D$, $R^X$, $R^Y$, $R^Z$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one $R^E$ is selected from the group consisting of alkyl, cycloalkyl, heteroalkyl, arylalkyl, silyl, alkenyl, cycloalkenyl, heteroalkenyl, alkynyl, aryl, heteroaryl, sulfanyl, sulfinyl, sulfonyl, phosphino, partially or fully deuterated variations thereof, and combinations thereof;
wherein any adjacent substitutents of R, R', $R^1$, $R^2$, $R^3$, $R^4$, $R^C$, $R^D$, $R^X$, $R^Y$, $R^Z$, and $R^E$ are optionally joined to form a ring; and
at least one of the following is true:
(i) at least one $R^E$ is selected from the group consisting of alkyl, cycloalkyl, partially or fully deuterated variations thereof, partially or fully fluorinated variations thereof, and combinations thereof, and
(ii) exactly one of $A^1$, $A^2$, $A^3$, $A^4$, $A^5$, $A^6$, $A^7$, and $A^8$ is nitrogen.

2. The compound of claim 1, wherein M is selected from the group consisting of Ir, Rh, Re, Ru, Os, Pt, Au, and Cu.

3. The compound of claim 1, wherein the compound has the formula $M(L_A)_2(L_C)$.

4. The compound of claim 1, wherein the compound has the formula $M(L_A)(L_B)_2$.

5. The compound of claim 1, wherein $A^1$, $A^2$, $A^3$, $A^4$, $A^5$, $A^6$, $A^7$, and $A^8$ are carbon.

6. The compound of claim 1, wherein exactly one of $A^1$, $A^2$, $A^3$, $A^4$, $A^5$, $A^6$, $A^7$, and $A^8$ is nitrogen.

7. The compound of claim 1, wherein X is O or $NR^1$.

8. The compound of claim 1, wherein ring C is benzene, and ring D is pyridine.

9. The compound of claim 1, wherein $L_A$ is selected from the group consisting of:

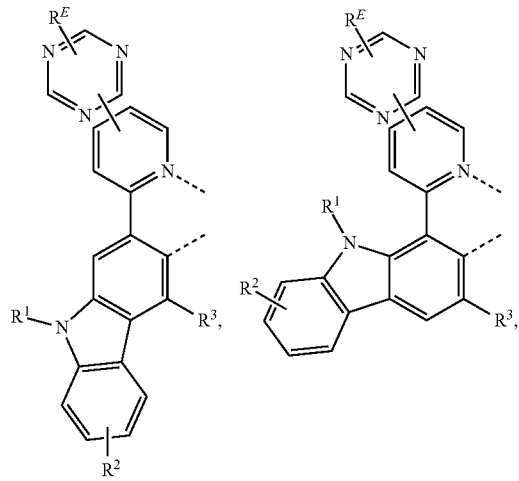

-continued
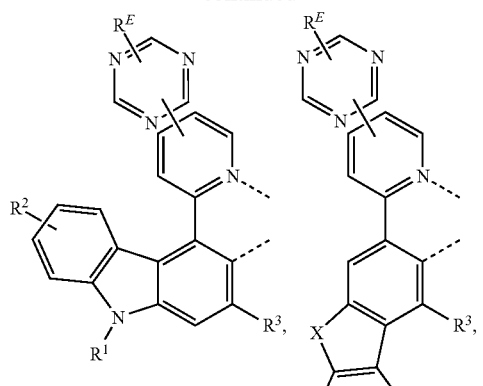
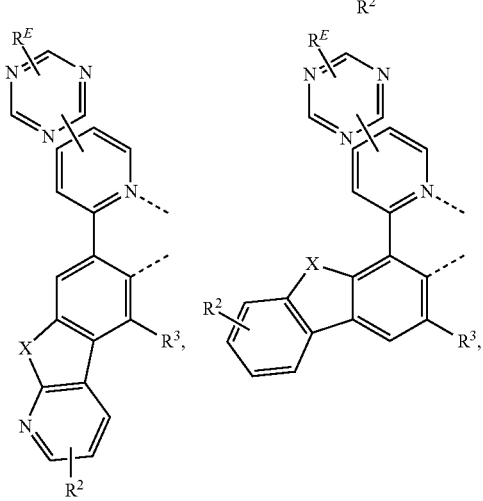
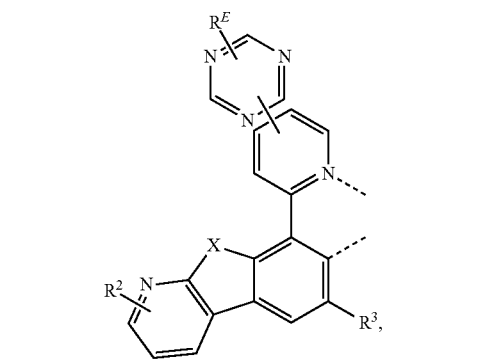
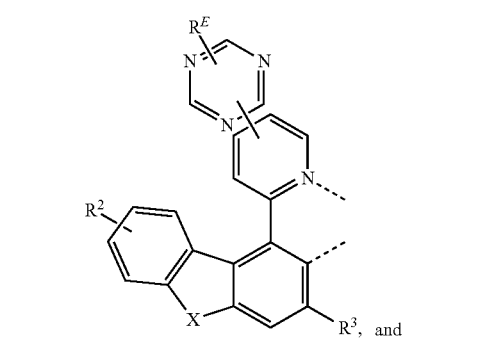
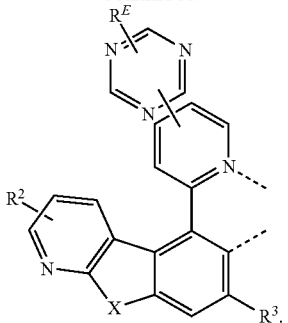
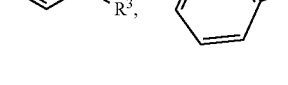
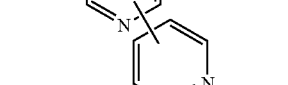

10. The compound of claim 1, wherein $L_B$ is selected from the group consisting of:
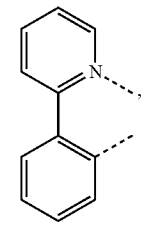  $L_{B1}$
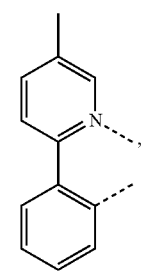  $L_{B2}$
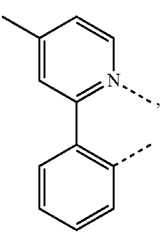  $L_{B3}$
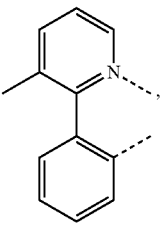  $L_{B4}$
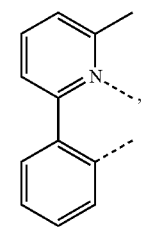  $L_{B5}$
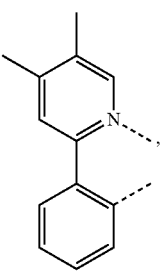  $L_{B6}$
-continued
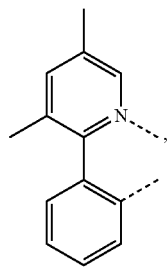  $L_{B7}$
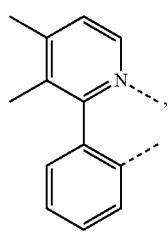  $L_{B8}$
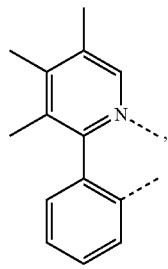  $L_{B9}$
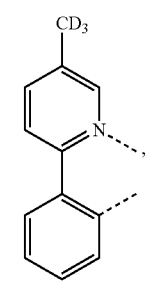  $L_{B10}$
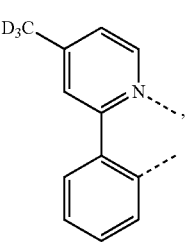  $L_{B11}$
$L_{B12}$ L_{B13}
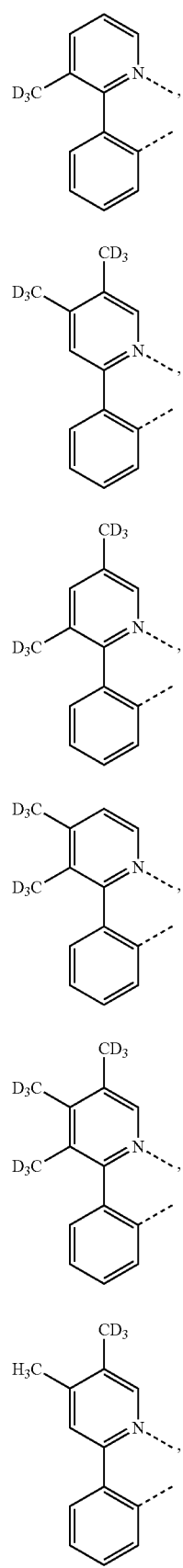
L_{B14}
L_{B15}
L_{B16}
L_{B17}
L_{B18}
L_{B19}
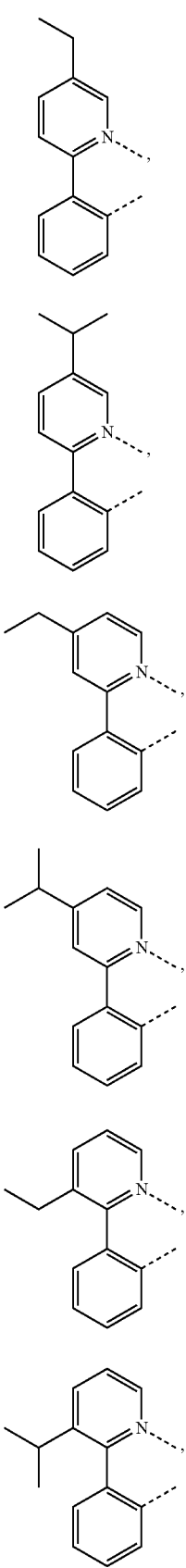
L_{B20}
L_{B21}
L_{B22}
L_{B23}
L_{B24}

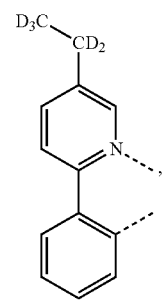 L_{B25}
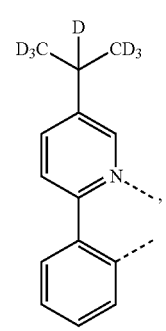 L_{B26}
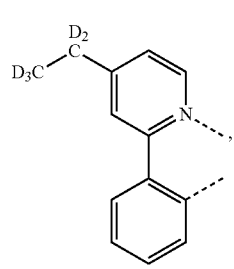 L_{B27}
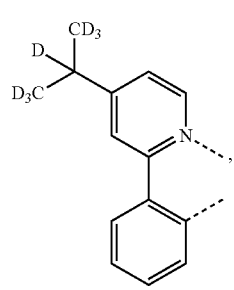 L_{B28}
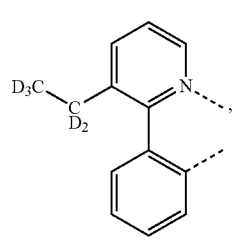 L_{B30}
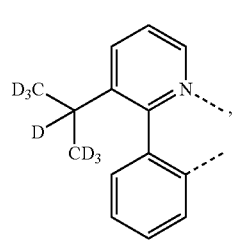 L_{B31}
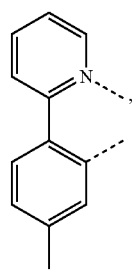 L_{B32}
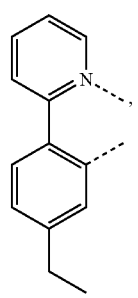 L_{B33}
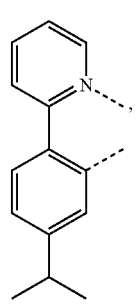 L_{B34}
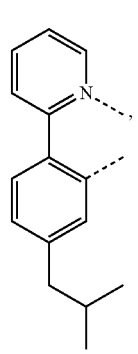 L_{B35}
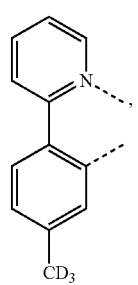 L_{B36}

-continued
L<sub>B37</sub>
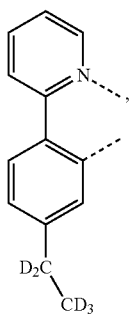
L<sub>B38</sub>
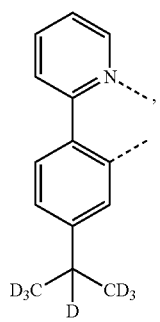
L<sub>B39</sub>
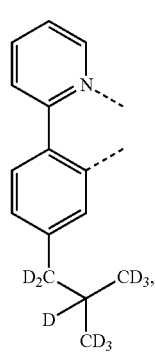
L<sub>B40</sub>
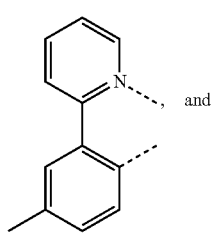
, and
L<sub>B41</sub>
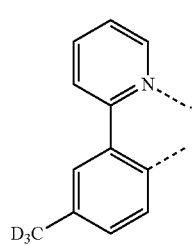
11. The compound of claim 1, where $L_C$ is selected from the group consisting of:
$L_{C1}$
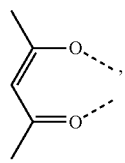
$L_{C2}$
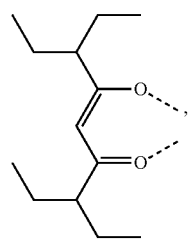
$L_{C3}$
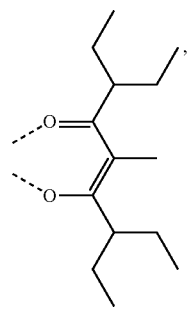
$L_{C4}$
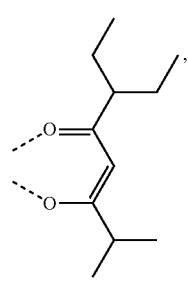
$L_{C5}$
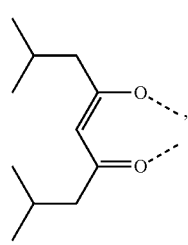
$L_{C6}$
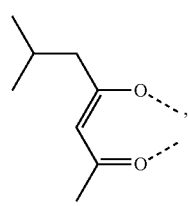

-continued

L_{C7}

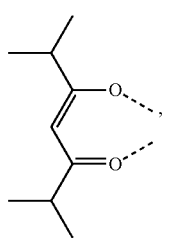

L_{C8}

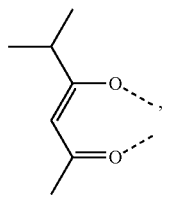

L_{C9}

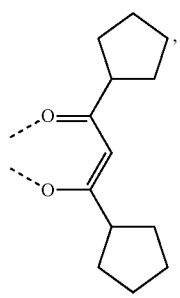

L_{C10}

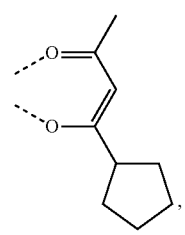

L_{C11}

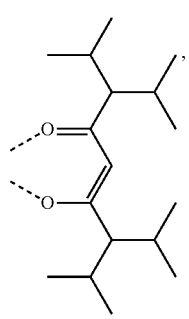

L_{C12}

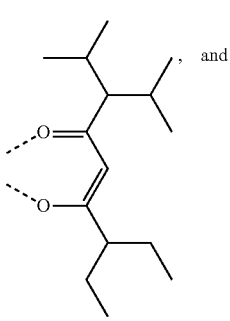, and

-continued

L_{C13}

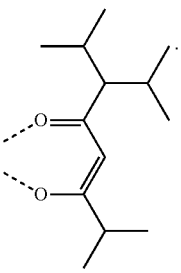

12. The compound of claim 1, wherein $R^E$ is di-substituted.

13. The compound of claim 1, wherein $L_A$ is selected from the group consisting of:

$L_{A185}$ through $L_{A190}$ and $L_{A193}$ through $L_{A198}$, each represented by the formula:

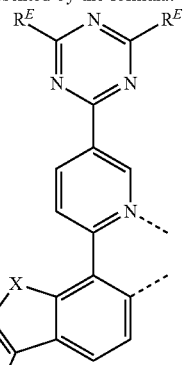

wherein in $L_{A185}$: X = O, $R^E = R^{A6}$, $R^2 = R^{B1}$,
in $L_{A186}$: X = O, $R^E = R^{A6}$, $R^2 = R^{B2}$,
in $L_{A187}$: X = O, $R^E = R^{A7}$, $R^2 = R^{B1}$,
in $L_{A188}$: X = O, $R^E = R^{A7}$, $R^2 = R^{B2}$,
in $L_{A189}$: X = O, $R^E = R^{A8}$, $R^2 = R^{B1}$,
in $L_{A190}$: X = O, $R^E = R^{A8}$, $R^2 = R^{B2}$,
in $L_{A193}$: X = S, $R^E = R^{A6}$, $R^2 = R^{B1}$,
in $L_{A194}$: X = S, $R^E = R^{A6}$, $R^2 = R^{B2}$,
in $L_{A195}$: X = S, $R^E = R^{A7}$, $R^2 = R^{B1}$,
in $L_{A196}$: X = S, $R^E = R^{A7}$, $R^2 = R^{B2}$,
in $L_{A197}$: X = S, $R^E = R^{A8}$, $R^2 = R^{B1}$, and
in $L_{A198}$: X = S, $R^E = R^{A8}$, $R^2 = R^{B2}$, $L_{A201}$ through $L_{A206}$ and $L_{A209}$ through $L_{A214}$, each represented by the formula:

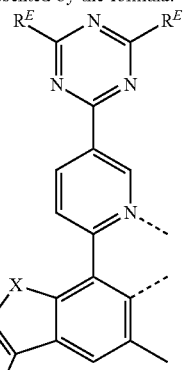

wherein in $L_{A201}$: X = O, $R^E = R^{A6}$, $R^2 = R^{B1}$,
in $L_{A202}$: X = O, $R^E = R^{A6}$, $R^2 = R^{B2}$,
in $L_{A203}$: X = O, $R^E = R^{A7}$, $R^2 = R^{B1}$,
in $L_{A204}$: X = O, $R^E = R^{A7}$, $R^2 = R^{B2}$, in $L_{A205}$: X = O, $R^E$ = $R^{48}$, $R^2$ = $R^{B1}$,
in $L_{A206}$: X = O, $R^E$ = $R^{48}$, $R^2$ = $R^{B2}$,
in $L_{A209}$: X = S, $R^E$ = $R^{46}$, $R^2$ = $R^{B1}$,
in $L_{A210}$: X = S, $R^E$ = $R^{46}$, $R^2$ = $R^{B2}$,
in $L_{A211}$: X = S, $R^E$ = $R^{47}$, $R^2$ = $R^{B1}$,
in $L_{A212}$: X = S, $R^E$ = $R^{47}$, $R^2$ = $R^{B2}$,
in $L_{A213}$: X = S, $R^E$ = $R^{48}$, $R^2$ = $R^{B1}$, and
in $L_{A214}$: X = S, $R^E$ = $R^{48}$, $R^2$ = $R^{B2}$, $L_{A217}$ through $L_{A222}$ and $L_{A225}$ through $L_{A230}$,
each represented by the formula:

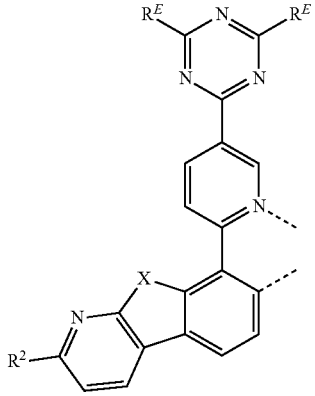

wherein in $L_{A217}$: X = O, $R^E$ = $R^{46}$, $R^2$ = $R^{B1}$,
in $L_{A218}$: X = O, $R^E$ = $R^{46}$, $R^2$ = $R^{B2}$,
in $L_{A219}$: X = O, $R^E$ = $R^{47}$, $R^2$ = $R^{B1}$,
in $L_{A220}$: X = O, $R^E$ = $R^{47}$, $R^2$ = $R^{B2}$,
in $L_{A221}$: X = O, $R^E$ = $R^{48}$, $R^2$ = $R^{B1}$,
in $L_{A222}$: X = O, $R^E$ = $R^{48}$, $R^2$ = $R^{B2}$,
in $L_{A225}$: X = S, $R^E$ = $R^{46}$, $R^2$ = $R^{B1}$,
in $L_{A226}$: X = S, $R^E$ = $R^{46}$, $R^2$ = $R^{B2}$,
in $L_{A227}$: X = S, $R^E$ = $R^{47}$, $R^2$ = $R^{B1}$,
in $L_{A228}$: X = S, $R^E$ = $R^{47}$, $R^2$ = $R^{B2}$,
in $L_{A229}$: X = S, $R^E$ = $R^{48}$, $R^2$ = $R^{B1}$, and
in $L_{A230}$: X = S, $R^E$ = $R^{48}$, $R^2$ = $R^{B2}$, $L_{A233}$ through $L_{A238}$ and $L_{A241}$ through $L_{A246}$,
each represented by the formula:

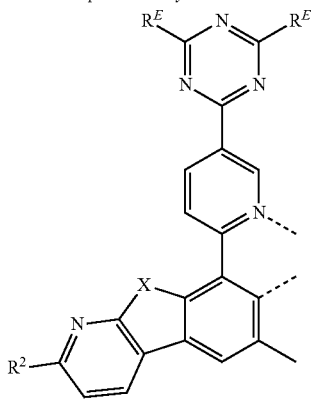

wherein in $L_{A233}$: X = O, $R^E$ = $R^{46}$, $R^2$ = $R^{B1}$,
in $L_{A234}$: X = O, $R^E$ = $R^{46}$, $R^2$ = $R^{B2}$,
in $L_{A235}$: X = O, $R^E$ = $R^{47}$, $R^2$ = $R^{B1}$,
in $L_{A236}$: X = O, $R^E$ = $R^{47}$, $R^2$ = $R^{B2}$,
in $L_{A237}$: X = O, $R^E$ = $R^{48}$, $R^2$ = $R^{B1}$,
in $L_{A238}$: X = O, $R^E$ = $R^{48}$, $R^2$ = $R^{B2}$,
in $L_{A241}$: X = S, $R^E$ = $R^{46}$, $R^2$ = $R^{B1}$,
in $L_{A242}$: X = S, $R^E$ = $R^{46}$, $R^2$ = $R^{B2}$,
in $L_{A243}$: X = S, $R^E$ = $R^{47}$, $R^2$ = $R^{B1}$,
in $L_{A244}$: X = S, $R^E$ = $R^{47}$, $R^2$ = $R^{B2}$,
in $L_{A245}$: X = S, $R^E$ = $R^{48}$, $R^2$ = $R^{B1}$, and
in $L_{A246}$: X = S, $R^E$ = $R^{48}$, $R^2$ = $R^{B2}$, $L_{A249}$ through $L_{A254}$ and $L_{A257}$ through $L_{A262}$,
each represented by the formula:

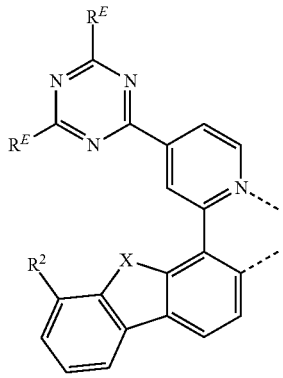

wherein in $L_{A249}$: X = O, $R^E$ = $R^{46}$, $R^2$ = $R^{B1}$,
in $L_{A250}$: X = O, $R^E$ = $R^{46}$, $R^2$ = $R^{B2}$,
in $L_{A251}$: X = O, $R^E$ = $R^{47}$, $R^2$ = $R^{B1}$,
in $L_{A252}$: X = O, $R^E$ = $R^{47}$, $R^2$ = $R^{B2}$,
in $L_{A253}$: X = O, $R^E$ = $R^{48}$, $R^2$ = $R^{B1}$,
in $L_{A254}$: X = O, $R^E$ = $R^{48}$, $R^2$ = $R^{B2}$,
in $L_{A257}$: X = S, $R^E$ = $R^{46}$, $R^2$ = $R^{B1}$,
in $L_{A258}$: X = S, $R^E$ = $R^{46}$, $R^2$ = $R^{B2}$,
in $L_{A259}$: X = S, $R^E$ = $R^{47}$, $R^2$ = $R^{B1}$,
in $L_{A260}$: X = S, $R^E$ = $R^{47}$, $R^2$ = $R^{B2}$,
in $L_{A261}$: X = S, $R^E$ = $R^{48}$, $R^2$ = $R^{B1}$, and
in $L_{A262}$: X = S, $R^E$ = $R^{48}$, $R^2$ = $R^{B2}$, $L_{A265}$ through $L_{A270}$ and $L_{A273}$ through $L_{A278}$,
each represented by the formula:

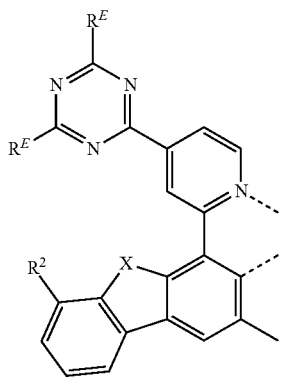

wherein in $L_{A265}$: X = O, $R^E$ = $R^{46}$, $R^2$ = $R^{B1}$,
in $L_{A266}$: X = O, $R^E$ = $R^{46}$, $R^2$ = $R^{B2}$,
in $L_{A267}$: X = O, $R^E$ = $R^{47}$, $R^2$ = $R^{B1}$,
in $L_{A268}$: X = O, $R^E$ = $R^{47}$, $R^2$ = $R^{B2}$,
in $L_{A269}$: X = O, $R^E$ = $R^{48}$, $R^2$ = $R^{B1}$,
in $L_{A270}$: X = O, $R^E$ = $R^{48}$, $R^2$ = $R^{B2}$,
in $L_{A273}$: X = S, $R^E$ = $R^{46}$, $R^2$ = $R^{B1}$,
in $L_{A274}$: X = S, $R^E$ = $R^{46}$, $R^2$ = $R^{B2}$,
in $L_{A275}$: X = S, $R^E$ = $R^{47}$, $R^2$ = $R^{B1}$,
in $L_{A276}$: X = S, $R^E$ = $R^{47}$, $R^2$ = $R^{B2}$,
in $L_{A277}$: X = S, $R^E$ = $R^{48}$, $R^2$ = $R^{B1}$, and
in $L_{A278}$: X = S, $R^E$ = $R^{48}$, $R^2$ = $R^{B2}$, $L_{A281}$ through $L_{A286}$ and $L_{A289}$ through $L_{A294}$, each represented by the formula:

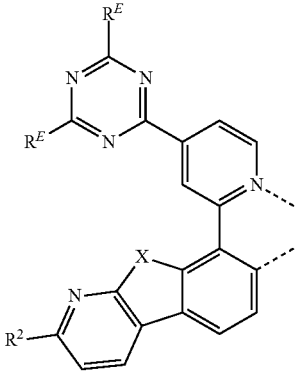

wherein in $L_{A281}$: X = O, $R^E = R^{46}$, $R^2 = R^{B1}$,
in $L_{A282}$: X = O, $R^E = R^{46}$, $R^2 = R^{B2}$,
in $L_{A283}$: X = O, $R^E = R^{47}$, $R^2 = R^{B1}$,
in $L_{A284}$: X = O, $R^E = R^{47}$, $R^2 = R^{B2}$,
in $L_{A285}$: X = O, $R^E = R^{48}$, $R^2 = R^{B1}$,
in $L_{A286}$: X = O, $R^E = R^{48}$, $R^2 = R^{B2}$,
in $L_{A289}$: X = S, $R^E = R^{46}$, $R^2 = R^{B1}$,
in $L_{A290}$: X = S, $R^E = R^{46}$, $R^2 = R^{B2}$,
in $L_{A291}$: X = S, $R^E = R^{47}$, $R^2 = R^{B1}$,
in $L_{A292}$: X = S, $R^E = R^{47}$, $R^2 = R^{B2}$,
in $L_{A293}$: X = S, $R^E = R^{48}$, $R^2 = R^{B1}$, and
in $L_{A294}$: X = S, $R^E = R^{48}$, $R^2 = R^{B2}$, $L_{A297}$ through $L_{A302}$ and $L_{A306}$ through $L_{A310}$, each represented by the formula:

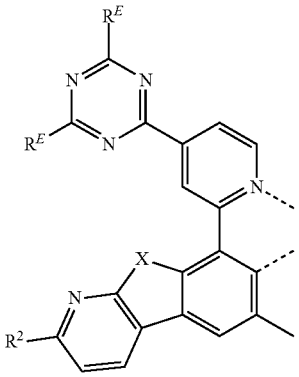

wherein in $L_{A297}$: X = O, $R^E = R^{46}$, $R^2 = R^{B1}$,
in $L_{A298}$: X = O, $R^E = R^{46}$, $R^2 = R^{B2}$,
in $L_{A299}$: X = O, $R^E = R^{47}$, $R^2 = R^{B1}$,
in $L_{A300}$: X = O, $R^E = R^{47}$, $R^2 = R^{B2}$,
in $L_{A301}$: X = O, $R^E = R^{48}$, $R^2 = R^{B1}$,
in $L_{A302}$: X = O, $R^E = R^{48}$, $R^2 = R^{B2}$,
in $L_{A305}$: X = S, $R^E = R^{46}$, $R^2 = R^{B1}$,
in $L_{A306}$: X = S, $R^E = R^{46}$, $R^2 = R^{B2}$,
in $L_{A307}$: X = S, $R^E = R^{47}$, $R^2 = R^{B1}$,
in $L_{A308}$: X = S, $R^E = R^{47}$, $R^2 = R^{B2}$,
in $L_{A309}$: X = S, $R^E = R^{48}$, $R^2 = R^{B1}$, and
in $L_{A310}$: X = S, $R^E = R^{48}$, $R^2 = R^{B2}$, $L_{A313}$ through $L_{A318}$ and $L_{A321}$ through $L_{A326}$, each represented by the formula:

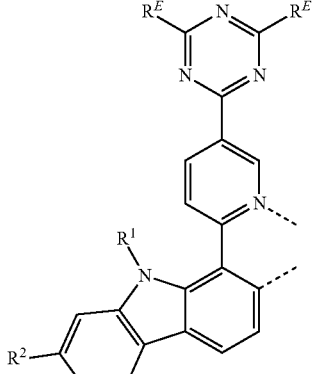

wherein in $L_{A313}$: $R^E = R^{46}$, $R^2 = R^{B1}$, $R^1 = R^{C1}$,
in $L_{A314}$: $R^E = R^{46}$, $R^2 = R^{B2}$, $R^1 = R^{C1}$,
in $L_{A315}$: $R^E = R^{47}$, $R^2 = R^{B1}$, $R^1 = R^{C1}$,
in $L_{A316}$: $R^E = R^{47}$, $R^2 = R^{B2}$, $R^1 = R^{C1}$,
in $L_{A317}$: $R^E = R^{48}$, $R^2 = R^{B1}$, $R^1 = R^{C1}$,
in $L_{A318}$: $R^E = R^{46}$, $R^2 = R^{B2}$, $R^1 = R^{C1}$,
in $L_{A321}$: $R^E = R^{46}$, $R^2 = R^{B1}$, $R^1 = R^{C2}$,
in $L_{A322}$: $R^E = R^{46}$, $R^2 = R^{B2}$, $R^1 = R^{C2}$,
in $L_{A323}$: $R^E = R^{47}$, $R^2 = R^{B1}$, $R^1 = R^{C2}$,
in $L_{A324}$: $R^E = R^{47}$, $R^2 = R^{B2}$, $R^1 = R^{C2}$,
in $L_{A325}$: $R^E = R^{48}$, $R^2 = R^{B1}$, $R^1 = R^{C2}$, and
in $L_{A326}$: $R^E = R^{48}$, $R^2 = R^{B2}$, $R^1 = R^{C2}$, $L_{A329}$ through $L_{A334}$ and $L_{A337}$ through $L_{A342}$, each represented by the formula:

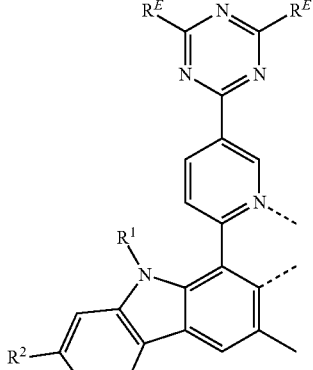

wherein in $L_{A329}$: $R^E = R^{46}$, $R^2 = R^{B1}$, $R^1 = R^{C1}$,
in $L_{A330}$: $R^E = R^{46}$, $R^2 = R^{B2}$, $R^1 = R^{C1}$,
in $L_{A331}$: $R^E = R^{47}$, $R^2 = R^{B1}$, $R^1 = R^{C1}$,
in $L_{A332}$: $R^E = R^{47}$, $R^2 = R^{B2}$, $R^1 = R^{C1}$,
in $L_{A333}$: $R^E = R^{48}$, $R^2 = R^{B1}$, $R^1 = R^{C1}$,
in $L_{A334}$: $R^E = R^{48}$, $R^2 = R^{B2}$, $R^1 = R^{C1}$,
in $L_{A337}$: $R^E = R^{46}$, $R^2 = R^{B1}$, $R^1 = R^{C2}$,
in $L_{A338}$: $R^E = R^{46}$, $R^2 = R^{B2}$, $R^1 = R^{C2}$,
in $L_{A339}$: $R^E = R^{47}$, $R^2 = R^{B1}$, $R^1 = R^{C2}$,
in $L_{A340}$: $R^E = R^{47}$, $R^2 = R^{B2}$, $R^1 = R^{C2}$,
in $L_{A341}$: $R^E = R^{48}$, $R^2 = R^{B1}$, $R^1 = R^{C2}$, and
in $L_{A342}$: $R^E = R^{48}$, $R^2 = R^{B2}$, $R^1 = R^{C2}$, $L_{A345}$ through $L_{A350}$ and $L_{A353}$ through $L_{A358}$, each represented by the formula:

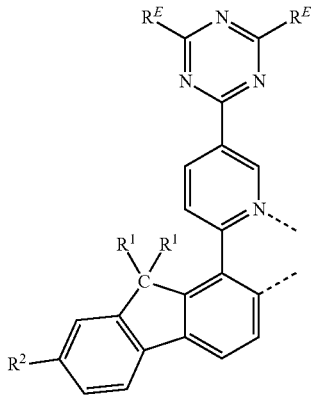

wherein in $L_{A345}$: $R^E = R^{46}$, $R^2 = R^{B1}$, $R^1 = R^{C1}$,
in $L_{A346}$: $R^E = R^{46}$, $R^2 = R^{B2}$, $R^1 = R^{C1}$,
in $L_{A347}$: $R^E = R^{47}$, $R^2 = R^{B1}$, $R^1 = R^{C1}$,
in $L_{A348}$: $R^E = R^{47}$, $R^2 = R^{B2}$, $R^1 = R^{C1}$,
in $L_{A349}$: $R^E = R^{48}$, $R^2 = R^{B1}$, $R^1 = R^{C1}$,
in $L_{A350}$: $R^E = R^{48}$, $R^2 = R^{B2}$, $R^1 = R^{C1}$,
in $L_{A353}$: $R^E = R^{46}$, $R^2 = R^{B1}$, $R^1 = R^{C2}$,
in $L_{A354}$: $R^E = R^{46}$, $R^2 = R^{B2}$, $R^1 = R^{C2}$,
in $L_{A355}$: $R^E = R^{47}$, $R^2 = R^{B1}$, $R^1 = R^{C2}$,
in $L_{A356}$: $R^E = R^{47}$, $R^2 = R^{B2}$, $R^1 = R^{C2}$,
in $L_{A357}$: $R^E = R^{48}$, $R^2 = R^{B1}$, $R^1 = R^{C2}$, and
in $L_{A358}$: $R^E = R^{48}$, $R^2 = R^{B2}$, $R^1 = R^{C2}$, $L_{A361}$ through $L_{A366}$ and $L_{A369}$ through $L_{A374}$, each represented by the formula:

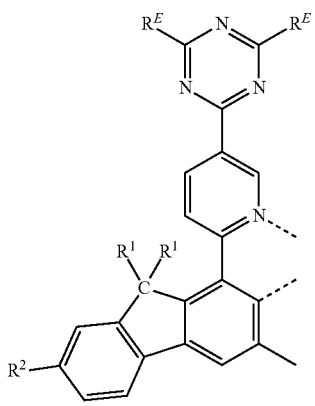

wherein in $L_{A361}$: $R^E = R^{46}$, $R^2 = R^{B1}$, $R^1 = R^{C1}$,
in $L_{A362}$: $R^E = R^{46}$, $R^2 = R^{B2}$, $R^1 = R^{C1}$,
in $L_{A363}$: $R^E = R^{47}$, $R^2 = R^{B1}$, $R^1 = R^{C1}$,
in $L_{A364}$: $R^E = R^{47}$, $R^2 = R^{B2}$, $R^1 = R^{C1}$,
in $L_{A365}$: $R^E = R^{48}$, $R^2 = R^{B1}$, $R^1 = R^{C1}$,
in $L_{A366}$: $R^E = R^{48}$, $R^2 = R^{B2}$, $R^1 = R^{C1}$,
in $L_{A369}$: $R^E = R^{46}$, $R^2 = R^{B1}$, $R^1 = R^{C2}$,
in $L_{A370}$: $R^E = R^{46}$, $R^2 = R^{B2}$, $R^1 = R^{C2}$,
in $L_{A371}$: $R^E = R^{47}$, $R^2 = R^{B1}$, $R^1 = R^{C2}$,
in $L_{A372}$: $R^E = R^{47}$, $R^2 = R^{B2}$, $R^1 = R^{C2}$,
in $L_{A373}$: $R^E = R^{48}$, $R^2 = R^{B1}$, $R^1 = R^{C2}$, and
in $L_{A374}$: $R^E = R^{48}$, $R^2 = R^{B2}$, $R^1 = R^{C2}$, $L_{A376}$ through $L_{A378}$ and $L_{A380}$ through $L_{A382}$, each represented by the formula:

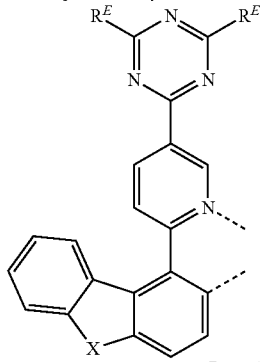

wherein in $L_{A376}$: $X = O$, $R^E = R^{46}$,
in $L_{A377}$: $X = O$, $R^E = R^{47}$,
in $L_{A378}$: $X = O$, $R^E = R^{48}$,
in $L_{A380}$: $X = S$, $R^E = R^{46}$,
in $L_{A381}$: $X = S$, $R^E = R^{47}$, and
in $L_{A382}$: $X = S$, $R^E = R^{48}$, $L_{A384}$ through $L_{A386}$ and $L_{A388}$ through $L_{A390}$, each represented by the formula::

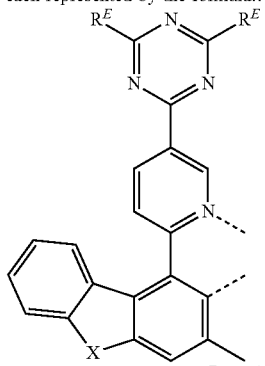

wherein in $L_{A384}$: $X = O$, $R^E = R^{46}$,
in $L_{A385}$: $X = O$, $R^E = R^{47}$,
in $L_{A386}$: $X = O$, $R^E = R^{48}$,
in $L_{A388}$: $X = S$, $R^E = R^{48}$,
in $L_{A389}$: $X = S$, $R^E = R^{47}$, and
in $L_{A390}$: $X = S$, $R^E = R^{48}$, $L_{A393}$ through $L_{A398}$ and $L_{A401}$ through $L_{A406}$, each represented by the formula:

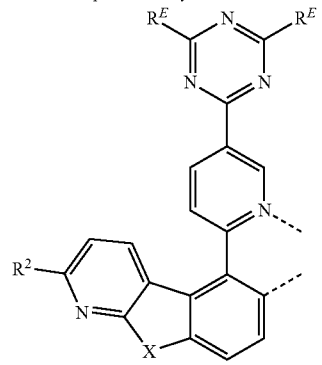

wherein in $L_{A393}$: $X = O$, $R^E = R^{46}$, $R^2 = R^{B1}$,
in $L_{A394}$: $X = O$, $R^E = R^{46}$, $R^2 = R^{B2}$,
in $L_{A395}$: $X = O$, $R^E = R^{47}$, $R^2 = R^{B1}$,
in $L_{A396}$: $X = O$, $R^E = R^{47}$, $R^2 = R^{B2}$,
in $L_{A397}$: $X = O$, $R^E = R^{48}$, $R^2 = R^{B1}$,
in $L_{A398}$: $X = O$, $R^E = R^{48}$, $R^2 = R^{B2}$,
in $L_{A401}$: $X = S$, $R^E = R^{46}$, $R^2 = R^{B1}$,
in $L_{A402}$: $X = S$, $R^E = R^{46}$, $R^2 = R^{B2}$, in $L_{A403}$: X = S, $R^E$ = $R^{A7}$, $R^2$ = $R^{B1}$,
in $L_{A404}$: X = S, $R^E$ = $R^{A7}$, $R^2$ = $R^{B2}$,
in $L_{A405}$: X = S, $R^E$ = $R^{A8}$, $R^2$ = $R^{B1}$, and
in $L_{A406}$: X = S, $R^E$ = $R^{A8}$, $R^2$ = $R^{B2}$, $L_{A409}$ through $L_{A414}$ and $L_{A417}$ through $L_{A422}$, each represented by the formula:

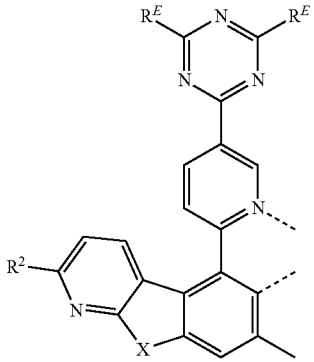

wherein in $L_{A409}$: X = O, $R^E$ = $R^{A6}$, $R^2$ = $R^{B1}$,
in $L_{A410}$: X = O, $R^E$ = $R^{A6}$, $R^2$ = $R^{B2}$,
in $L_{A411}$: X = O, $R^E$ = $R^{A7}$, $R^2$ = $R^{B1}$,
in $L_{A412}$: X = O, $R^E$ = $R^{A7}$, $R^2$ = $R^{B2}$,
in $L_{A413}$: X = O, $R^E$ = $R^{A8}$, $R^2$ = $R^{B1}$,
in $L_{A414}$: X = O, $R^E$ = $R^{A6}$, $R^2$ = $R^{B2}$,
in $L_{A417}$: X = S, $R^E$ = $R^{A6}$, $R^2$ = $R^{B1}$,
in $L_{A418}$: X = S, $R^E$ = $R^{A6}$, $R^2$ = $R^{B2}$,
in $L_{A419}$: X = S, $R^E$ = $R^{A7}$, $R^2$ = $R^{B1}$,
in $L_{A420}$: X = S, $R^E$ = $R^{A7}$, $R^2$ = $R^{B2}$,
in $L_{A421}$: X = S, $R^E$ = $R^{A8}$, $R^2$ = $R^{B1}$, and
in $L_{A422}$: X = S, $R^E$ = $R^{A8}$, $R^2$ = $R^{B2}$, $L_{A425}$ through $L_{A430}$ and $L_{A433}$ through $L_{A438}$, each represented by the formula:

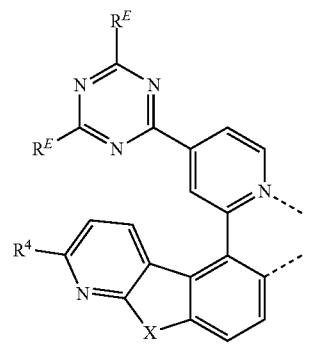

wherein in $L_{A425}$: X = O, $R^E$ = $R^{A6}$, $R^4$ = $R^{B1}$,
in $L_{A426}$: X = O, $R^E$ = $R^{A6}$, $R^4$ = $R^{B2}$,
in $L_{A427}$: X = O, $R^E$ = $R^{A7}$, $R^4$ = $R^{B1}$,
in $L_{A428}$: X = O, $R^E$ = $R^{A7}$, $R^4$ = $R^{B2}$,
in $L_{A429}$: X = O, $R^E$ = $R^{A8}$, $R^4$ = $R^{B1}$,
in $L_{A430}$: X = O, $R^E$ = $R^{A8}$, $R^4$ = $R^{B2}$,
in $L_{A433}$: X = S, $R^E$ = $R^{A6}$, $R^4$ = $R^{B1}$,
in $L_{A434}$: X = S, $R^E$ = $R^{A6}$, $R^4$ = $R^{B2}$,
in $L_{A435}$: X = S, $R^E$ = $R^{A7}$, $R^4$ = $R^{B1}$,
in $L_{A436}$: X = S, $R^E$ = $R^{A7}$, $R^4$ = $R^{B2}$,
in $L_{A437}$: X = S, $R^E$ = $R^{A8}$, $R^4$ = $R^{B1}$, and
in $L_{A438}$: X = S, $R^E$ = $R^{A8}$, $R^4$ = $R^{B2}$, $L_{A441}$ through $L_{A446}$ and $L_{A449}$ through $L_{A454}$, each represented by the formula:

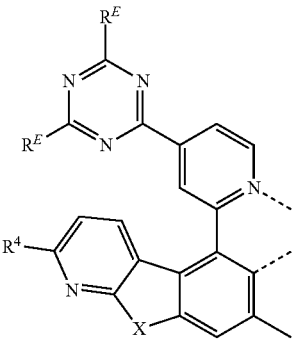

wherein in $L_{A441}$: X = O, $R^E$ = $R^{A6}$, $R^4$ = $R^{B1}$,
in $L_{A442}$: X = O, $R^E$ = $R^{A6}$, $R^4$ = $R^{B2}$,
in $L_{A443}$: X = O, $R^E$ = $R^{A7}$, $R^4$ = $R^{B1}$,
in $L_{A444}$: X = O, $R^E$ = $R^{A7}$, $R^4$ = $R^{B2}$,
in $L_{A445}$: X = O, $R^E$ = $R^{A8}$, $R^4$ = $R^{B1}$,
in $L_{A446}$: X = O, $R^E$ = $R^{A8}$, $R^4$ = $R^{B2}$,
in $L_{A449}$: X = S, $R^E$ = $R^{A6}$, $R^4$ = $R^{B1}$,
in $L_{A450}$: X = S, $R^E$ = $R^{A6}$, $R^4$ = $R^{B2}$,
in $L_{A451}$: X = S, $R^E$ = $R^{A7}$, $R^4$ = $R^{B1}$,
in $L_{A452}$: X = S, $R^E$ = $R^{A7}$, $R^4$ = $R^{B2}$,
in $L_{A453}$: X = S, $R^E$ = $R^{A8}$, $R^4$ = $R^{B1}$, and
in $L_{A454}$: X = S, $R^E$ = $R^{A8}$, $R^4$ = $R^{B2}$, $L_{A456}$ through $L_{A458}$ and $L_{A460}$ through $L_{A462}$, each represented by the formula:

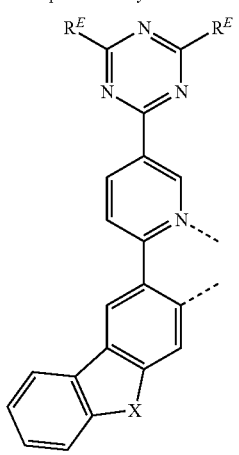

wherein in $L_{A456}$: X = O, $R^E$ = $R^{A6}$,
in $L_{A457}$: X = O, $R^E$ = $R^{A7}$,
in $L_{A458}$: X = O, $R^E$ = $R^{A8}$,
in $L_{A460}$: X = S, $R^E$ = $R^{A6}$,
in $L_{A461}$: X = S, $R^E$ = $R^{A7}$, and
in $L_{A462}$: X = S, $R^E$ = $R^{A8}$, $L_{A464}$ through $L_{A466}$ and $L_{A468}$ through $L_{A470}$, each represented by the formula:

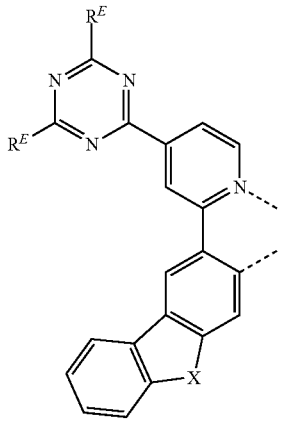

wherein in $L_{A464}$: X = O, $R^E = R^{A6}$,
in $L_{A465}$: X = O, $R^E = R^{A7}$,
in $L_{A466}$: X = O, $R^E = R^{A8}$,
in $L_{A468}$: X = S, $R^E = R^{A6}$,
in $L_{A469}$: X = S, $R^E = R^{A7}$, and
in $L_{A470}$: X = S, $R^E = R^{A8}$, $L_{A480}$ through $L_{A482}$ and $L_{A484}$ through $L_{A486}$, each represented by the formula:

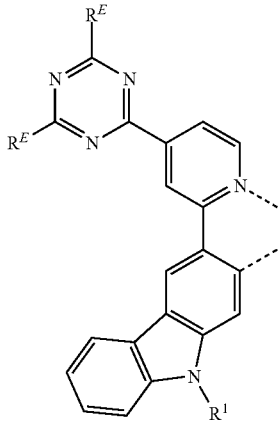

wherein in $L_{A480}$: $R^E = R^{A6}$, $R^1 = R^{C1}$,
in $L_{A481}$: $R^E = R^{A7}$, $R^1 = R^{C1}$,
in $L_{A482}$: $R^E = R^{A8}$, $R^1 = R^{C1}$,
in $L_{A484}$: $R^E = R^{A6}$, $R^1 = R^{C2}$,
in $L_{A485}$: $R^E = R^{A7}$, $R^1 = R^{C2}$, and
in $L_{A486}$: $R^E = R^{A8}$, $R^1 = R^{C2}$, $L_{A472}$ through $L_{A474}$ and $L_{A476}$ through $L_{A478}$, each represented by the formula:

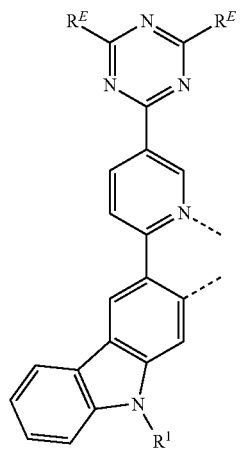

wherein in $L_{A472}$: $R^E = R^{A6}$, $R^1 = R^{C1}$,
in $L_{A473}$: $R^E = R^{A7}$, $R^1 = R^{C1}$,
in $L_{A474}$: $R^E = R^{A8}$, $R^1 = R^{C1}$,
in $L_{A476}$: $R^E = R^{A6}$, $R^1 = R^{C2}$,
in $L_{A477}$: $R^E = R^{A7}$, $R^1 = R^{C2}$, and
in $L_{A478}$: $R^E = R^{A8}$, $R^1 = R^{C2}$, $L_{A488}$ through $L_{A490}$ and $L_{A492}$ through $L_{A494}$, each represented by the formula:

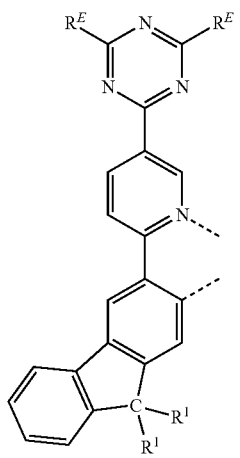

wherein in $L_{A488}$: $R^E = R^{A6}$, $R^1 = R^{C1}$,
in $L_{A489}$: $R^E = R^{A7}$, $R^1 = R^{C1}$,
in $L_{A490}$: $R^E = R^{A8}$, $R^1 = R^{C1}$,
in $L_{A492}$: $R^E = R^{A6}$, $R^1 = R^{C2}$,
in $L_{A493}$: $R^E = R^{A7}$, $R^1 = R^{C2}$, and
in $L_{A494}$: $R^E = R^{A8}$, $R^1 = R^{C2}$, $L_{A496}$ through $L_{A498}$ and $L_{A500}$ through $L_{A502}$, each represented by the formula:

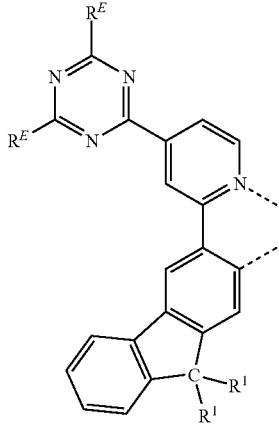

wherein in $L_{A496}$: $R^E = R^{46}$, $R^1 = R^{C1}$,
in $L_{A497}$: $R^E = R^{47}$, $R^1 = R^{C1}$,
in $L_{A498}$: $R^E = R^{48}$, $R^1 = R^{C1}$,
in $L_{A500}$: $R^E = R^{46}$, $R^1 = R^{C2}$,
in $L_{A501}$: $R^E = R^{47}$, $R^1 = R^{C2}$, and
in $L_{A502}$: $R^E = R^{48}$, $R^1 = R^{C2}$, $L_{A505}$ through $L_{A510}$ and $L_{A513}$ through $L_{A518}$, each represented by the formula:

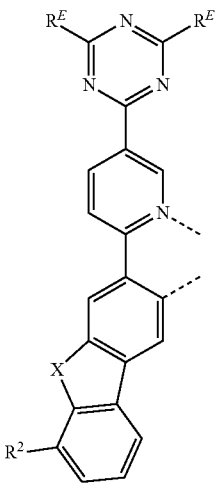

wherein in $L_{A505}$: $X = O$, $R^E = R^{46}$, $R^2 = R^{B1}$,
in $L_{A506}$: $X = O$, $R^E = R^{46}$, $R^2 = R^{B2}$,
in $L_{A507}$: $X = O$, $R^E = R^{47}$, $R^2 = R^{B1}$,
in $L_{A508}$: $X = O$, $R^E = R^{47}$, $R^2 = R^{B2}$,
in $L_{A509}$: $X = O$, $R^E = R^{48}$, $R^2 = R^{B1}$,
in $L_{A510}$: $X = O$, $R^E = R^{48}$, $R^2 = R^{B2}$,
in $L_{A513}$: $X = S$, $R^E = R^{46}$, $R^2 = R^{B1}$,
in $L_{A514}$: $X = S$, $R^E = R^{46}$, $R^2 = R^{B2}$,
in $L_{A515}$: $X = S$, $R^E = R^{47}$, $R^2 = R^{B1}$,
in $L_{A516}$: $X = S$, $R^E = R^{47}$, $R^2 = R^{B2}$,
in $L_{A517}$: $X = S$, $R^E = R^{48}$, $R^2 = R^{B1}$, and
in $L_{A518}$: $X = S$, $R^E = R^{48}$, $R^2 = R^{B2}$, $L_{A521}$ through $L_{A526}$ and $L_{A529}$ through $L_{A534}$, each represented by the formula:

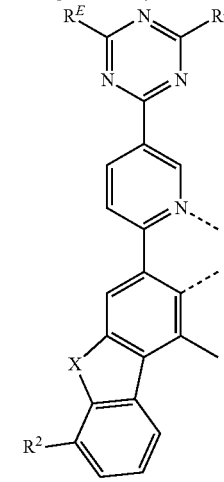

wherein in $L_{A521}$: $X = O$, $R^E = R^{46}$, $R^2 = R^{B1}$,
in $L_{A522}$: $X = O$, $R^E = R^{46}$, $R^2 = R^{B2}$,
in $L_{A523}$: $X = O$, $R^E = R^{47}$, $R^2 = R^{B1}$,
in $L_{A524}$: $X = O$, $R^E = R^{47}$, $R^2 = R^{B2}$,
in $L_{A525}$: $X = O$, $R^E = R^{48}$, $R^2 = R^{B1}$,
in $L_{A526}$: $X = O$, $R^E = R^{48}$, $R^2 = R^{B2}$,
in $L_{A529}$: $X = S$, $R^E = R^{46}$, $R^2 = R^{B1}$,
in $L_{A530}$: $X = S$, $R^E = R^{46}$, $R^2 = R^{B2}$,
in $L_{A531}$: $X = S$, $R^E = R^{47}$, $R^2 = R^{B1}$,
in $L_{A532}$: $X = S$, $R^E = R^{47}$, $R^2 = R^{B2}$,
in $L_{A533}$: $X = S$, $R^E = R^{48}$, $R^2 = R^{B1}$, and
in $L_{A534}$: $X = S$ $R^E = R^{48}$, $R^2 = R^{B2}$, $L_{A537}$ through $L_{A542}$ and $L_{A545}$ through $L_{A550}$, each represented by the formula:

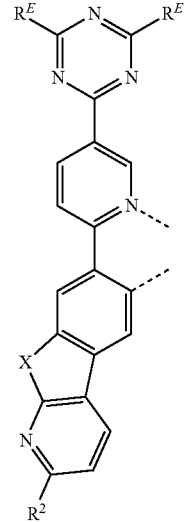

wherein in $L_{A537}$: $X = O$, $R^E = R^{46}$, $R^2 = R^{B1}$,
in $L_{A538}$: $X = O$, $R^E = R^{46}$, $R^2 = R^{B2}$,
in $L_{A539}$: $X = O$, $R^E = R^{47}$, $R^2 = R^{B1}$,
in $L_{A540}$: $X = O$, $R^E = R^{47}$, $R^2 = R^{B2}$,
in $L_{A541}$: $X = O$, $R^E = R^{48}$, $R^2 = R^{B1}$,
in $L_{A542}$: $X = O$, $R^E = R^{48}$, $R^2 = R^{B2}$,
in $L_{A545}$: $X = S$, $R^E = R^{46}$, $R^2 = R^{B1}$,
in $L_{A546}$: $X = S$, $R^E = R^{46}$, $R^2 = R^{B2}$,
in $L_{A547}$: $X = S$, $R^E = R^{47}$, $R^2 = R^{B1}$,
in $L_{A548}$: $X = S$, $R^E = R^{47}$, $R^2 = R^{B2}$,
in $L_{A549}$: $X = S$, $R^E = R^{48}$, $R^2 = R^{B1}$, and
in $L_{A550}$: $X = S$, $R^E = R^{48}$, $R^2 = R^{B2}$, $L_{A553}$ through $L_{A558}$ and $L_{A561}$ through $L_{A566}$, each represented by the formula:

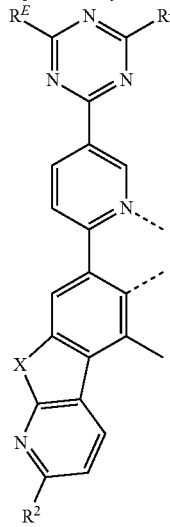

wherein in $L_{A553}$: X = O, $R^E = R^{46}$, $R^2 = R^{B1}$,
in $L_{A554}$: X = O, $R^E = R^{46}$, $R^2 = R^{B2}$,
in $L_{A555}$: X = O, $R^E = R^{47}$, $R^2 = R^{B1}$,
in $L_{A556}$: X = O, $R^E = R^{47}$, $R^2 = R^{B2}$,
in $L_{A557}$: X = O, $R^E = R^{48}$, $R^2 = R^{B1}$,
in $L_{A558}$: X = O, $R^E = R^{48}$, $R^2 = R^{B2}$,
in $L_{A561}$: X = S, $R^E = R^{46}$, $R^2 = R^{B1}$,
in $L_{A562}$: X = S, $R^E = R^{46}$, $R^2 = R^{B2}$,
in $L_{A563}$: X = S, $R^E = R^{47}$, $R^2 = R^{B1}$,
in $L_{A564}$: X = S, $R^E = R^{47}$, $R^2 = R^{B2}$,
in $L_{A565}$: X = S, $R^E = R^{48}$, $R^2 = R^{B1}$, and
in $L_{A566}$: X = S, $R^E = R^{48}$, $R^2 = R^{B2}$, $L_{A569}$ through $L_{A574}$ and $L_{A577}$ through $L_{A582}$, each represented by the formula:

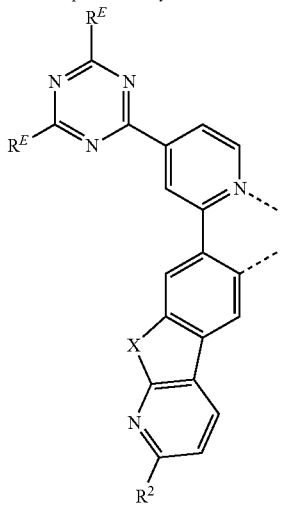

wherein in $L_{A569}$: X = O, $R^E = R^{46}$, $R^2 = R^{B1}$,
in $L_{A570}$: X = O, $R^E = R^{46}$, $R^2 = R^{B2}$,
in $L_{A571}$: X = O, $R^E = R^{47}$, $R^2 = R^{B1}$,
in $L_{A572}$: X = O, $R^E = R^{47}$, $R^2 = R^{B2}$,
in $L_{A573}$: X = O, $R^E = R^{48}$, $R^2 = R^{B1}$,
in $L_{A574}$: X = O, $R^E = R^{48}$, $R^2 = R^{B2}$,
in $L_{A577}$: X = S, $R^E = R^{46}$, $R^2 = R^{B1}$,
in $L_{A578}$: X = S, $R^E = R^{46}$, $R^2 = R^{B2}$,
in $L_{A579}$: X = S, $R^E = R^{47}$, $R^2 = R^{B1}$,
in $L_{A580}$: X = S, $R^E = R^{47}$, $R^2 = R^{B2}$,
in $L_{A581}$: X = S, $R^E = R^{48}$, $R^2 = R^{B1}$, and
in $L_{A582}$: X = S, $R^E = R^{48}$, $R^2 = R^{B2}$, $L_{A585}$ through $L_{A590}$ and $L_{A593}$ through $L_{A598}$, each represented by the formula:

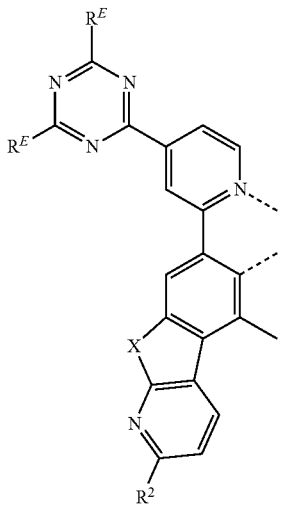

wherein in $L_{A585}$: X = O, $R^E = R^{46}$, $R^2 = R^{B1}$,
in $L_{A586}$: X = O, $R^E = R^{46}$, $R^2 = R^{B2}$,
in $L_{A587}$: X = O, $R^E = R^{47}$, $R^2 = R^{B1}$,
in $L_{A588}$: X = O, $R^E = R^{47}$, $R^2 = R^{B2}$,
in $L_{A589}$: X = O, $R^E = R^{48}$, $R^2 = R^{B1}$,
in $L_{A590}$: X = O, $R^E = R^{48}$, $R^2 = R^{B2}$,
in $L_{A593}$: X = S, $R^E = R^{46}$, $R^2 = R^{B1}$,
in $L_{A594}$: X = S, $R^E = R^{46}$, $R^2 = R^{B2}$,
in $L_{A595}$: X = S, $R^E = R^{47}$, $R^2 = R^{B1}$,
in $L_{A596}$: X = S, $R^E = R^{47}$, $R^2 = R^{B2}$,
in $L_{A597}$: X = S, $R^E = R^{48}$, $R^2 = R^{B1}$, and
in $L_{A598}$: X = S, $R^E = R^{48}$, $R^2 = R^{B2}$, $L_{A600}$ through $L_{A602}$ and $L_{A604}$ through $L_{A606}$, each represented by the formula:

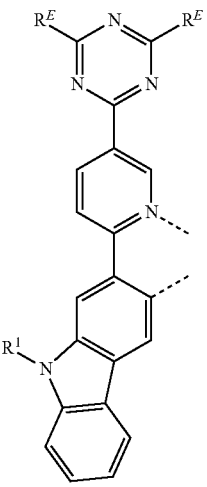

wherein in $L_{A600}$: $R^E = R^{46}$, $R^1 = R^{C1}$,
in $L_{A601}$: $R^E = R^{47}$, $R^1 = R^{C1}$,
in $L_{A602}$: $R^E = R^{48}$, $R^1 = R^{C1}$,
in $L_{A604}$: $R^E = R^{46}$, $R^1 = R^{C2}$,
in $L_{A605}$: $R^E = R^{47}$, $R^1 = R^{C2}$, and
in $L_{A606}$: $R^E = R^{48}$, $R^1 = R^{C2}$, $L_{A608}$ through $L_{A610}$ and $L_{A612}$ through $L_{A614}$, each represented by the formula:

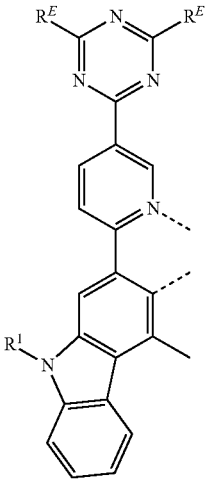

wherein in $L_{A608}$: $R^E = R^{A6}$, $R^1 = R^{C1}$,
in $L_{A609}$: $R^E = R^{A7}$, $R^1 = R^{C1}$,
in $L_{A610}$: $R^E = R^{A8}$, $R^1 = R^{C1}$,
in $L_{A612}$: $R^E = R^{A6}$, $R^1 = R^{C2}$,
in $L_{A613}$: $R^E = R^{A7}$, $R^1 = R^{C2}$, and
in $L_{A614}$: $R^E = R^{A8}$, $R^1 = R^{C2}$, $L_{A616}$ through $L_{A618}$ and $L_{A620}$ through $L_{A622}$, each represented by the formula:

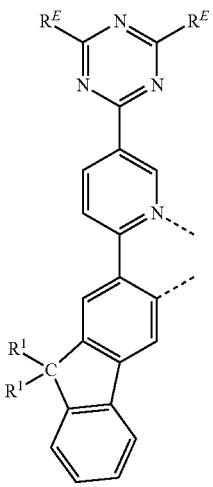

wherein in $L_{A616}$: $R^E = R^{A6}$, $R^1 = R^{C1}$,
in $L_{A617}$: $R^E = R^{A7}$, $R^1 = R^{C1}$,
in $L_{A618}$: $R^E = R^{A8}$, $R^1 = R^{C1}$,
in $L_{A620}$: $R^E = R^{A6}$, $R^1 = R^{C2}$,
in $L_{A621}$: $R^E = R^{A7}$, $R^1 = R^{C2}$, and
in $L_{A622}$: $R^E = R^{A8}$, $R^1 = R^{C2}$, and $L_{A624}$ through $L_{A626}$ and $L_{A628}$ through $L_{A630}$, each represented by the formula:

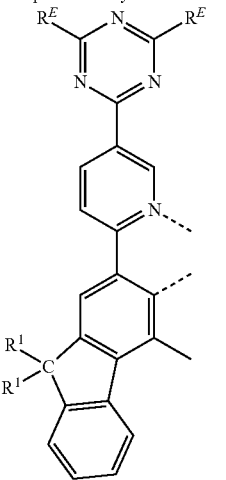

wherein in $L_{A624}$: $R^E = R^{A6}$, $R^1 = R^{C1}$,
in $L_{A625}$: $R^E = R^{A7}$, $R^1 = R^{C1}$,
in $L_{A626}$: $R^E = R^{A8}$, $R^1 = R^{C1}$,
in $L_{A628}$: $R^E = R^{A6}$, $R^1 = R^{C2}$,
in $L_{A629}$: $R^E = R^{A7}$, $R^1 = R^{C2}$, and
in $L_{A630}$ = $R^E = R^{A8}$, $R1 = R^{C2}$, wherein $R^{A6}$ to $R^{A8}$ have the following structures:

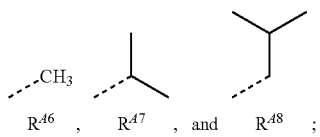

wherein $R^{B1}$ and $R^{B2}$ have the following structures:

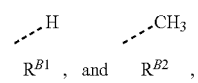

and
wherein $R^{C1}$ to $R^{C2}$ have the following structures:

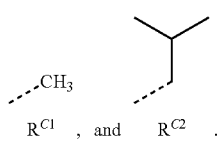

14. The compound of claim 13, wherein the compound has the formula $Ir(L_{Ak})(L_{Bj})_2$;
wherein $L_{Ak}$ is selected from $L_{A185}$-$L_{A190}$, $L_{A193}$-$L_{A198}$, $L_{A201}$-$L_{A206}$, $L_{A209}$-$L_{A214}$, $L_{A217}$-$L_{A222}$, $L_{A225}$-$L_{A230}$, $L_{A233}$-$L_{A238}$, $L_{A241}$-$L_{A246}$, $L_{A249}$-$L_{A254}$, $L_{A257}$-$L_{A262}$, $L_{A265}$-$L_{A270}$, $L_{A273}$-$L_{A278}$, $L_{A281}$-$L_{A286}$, $L_{A289}$-$L_{A294}$, $L_{A297}$-$L_{A302}$, $L_{A305}$-$L_{A310}$, $L_{A313}$-$L_{A318}$, $L_{A321}$-$L_{A326}$, $L_{A329}$-$L_{A334}$, $L_{A337}$-$L_{A342}$, $L_{A345}$-$L_{A350}$, $L_{A353}$-$L_{A358}$, $L_{A361}$-$L_{A366}$, $L_{A369}$-$L_{A374}$, $L_{A376}$-$L_{A378}$, $L_{A380}$-$L_{A382}$, $L_{A384}$-$L_{A386}$, $L_{A388}$-$L_{A390}$, $L_{A393}$-$L_{A398}$, $L_{A401}$-$L_{A408}$, $L_{A411}$-$L_{A414}$, $L_{A417}$-$L_{A422}$, $L_{A425}$-$L_{A430}$, $L_{A433}$-$L_{A438}$, L$_{A441}$-L$_{A446}$, L$_{A449}$-L$_{A454}$, L$_{A456}$-L$_{A458}$, L$_{A460}$-L$_{A462}$, L$_{A464}$-L$_{A466}$, L$_{A468}$-L$_{A470}$, L$_{A472}$-L$_{A474}$, L$_{A476}$-L$_{A478}$, L$_{A480}$-L$_{A482}$, L$_{A484}$-L$_{A486}$, L$_{A488}$-L$_{A490}$, L$_{A492}$-L$_{A494}$, L$_{A496}$-L$_{A498}$, L$_{A500}$-L$_{A502}$, L$_{A505}$-L$_{A510}$, L$_{A513}$-L$_{A518}$, L$_{A521}$-L$_{A526}$, L$_{A529}$-L$_{A534}$, L$_{A534}$-L$_{A542}$, L$_{A545}$-L$_{A550}$, L$_{A553}$-L$_{A558}$, L$_{A561}$-L$_{A566}$, L$_{A569}$-L$_{A574}$, L$_{A577}$-L$_{A582}$, L$_{A585}$-L$_{A590}$, L$_{A593}$-L$_{A598}$, L$_{A600}$-L$_{A602}$, L$_{A604}$-L$_{A606}$, L$_{A608}$-L$_{A610}$, L$_{A612}$-L$_{A614}$, L$_{A616}$-L$_{A618}$, L$_{A620}$-L$_{A622}$, L$_{A624}$-L$_{A626}$, and L$_{A628}$-L$_{A630}$; and wherein L$_{Bj}$ is selected from L$_{B1}$ through L$_{B41}$ are defined as follows:

L$_{B1}$
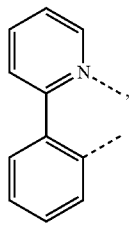

L$_{B2}$
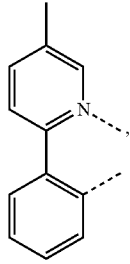

L$_{B3}$
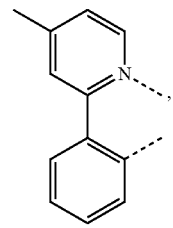

L$_{B4}$
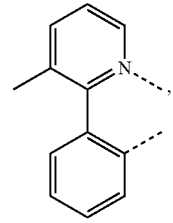

L$_{B5}$
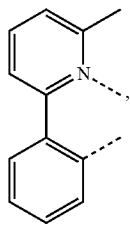

-continued

L$_{B6}$
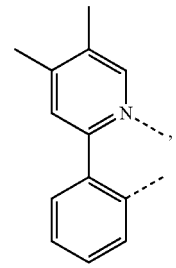

L$_{B7}$
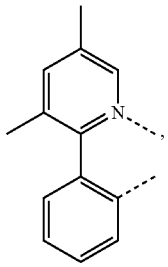

L$_{B8}$
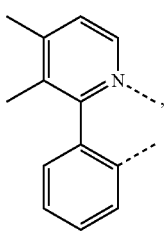

L$_{B9}$
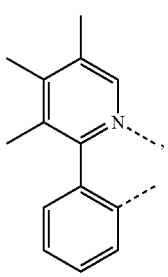

L$_{B10}$
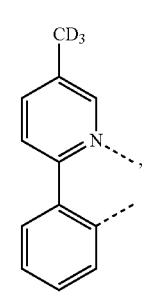

L$_{B11}$
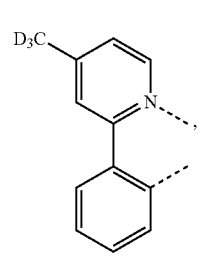

L_{B12} 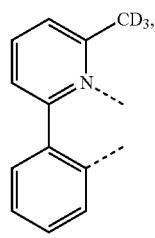
L_{B13} 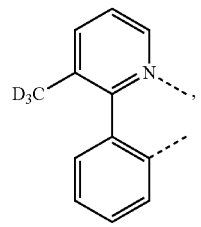
L_{B14} 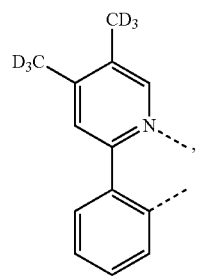
L_{B15} 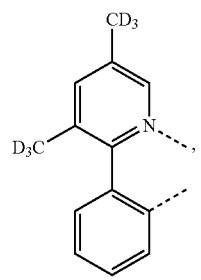
L_{B16} 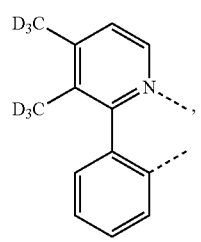
L_{B17} 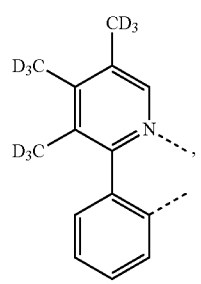
L_{B18} 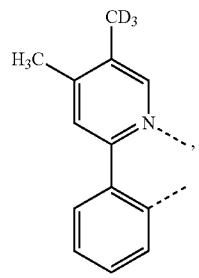
L_{B19} 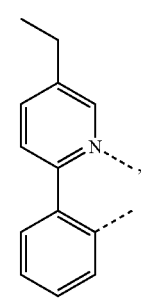
L_{B20} 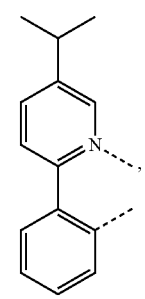
L_{B21} 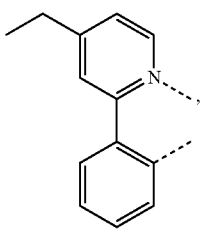
L_{B22} 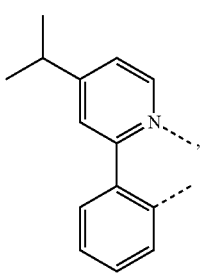
L_{B23} 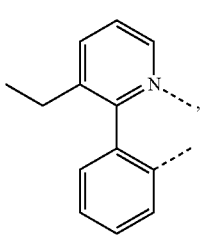

L_{B24}
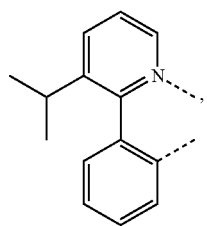
L_{B25}
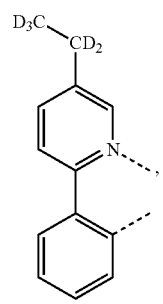
L_{B26}
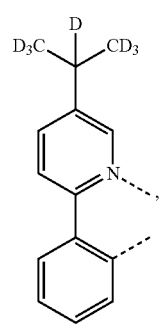
L_{B27}
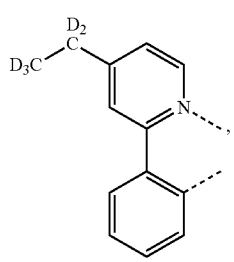
L_{B28}
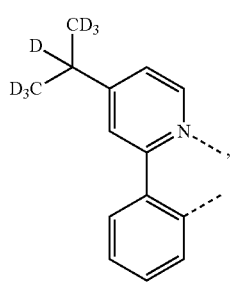
L_{B30}
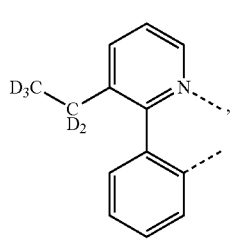
L_{B31}
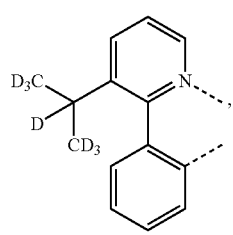
L_{B32}
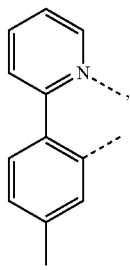
L_{B33}
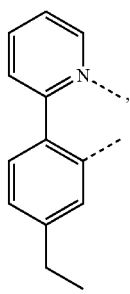
L_{B34}
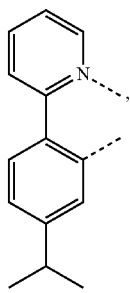
L_{B35}
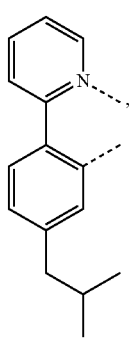

-continued $L_{B36}$ 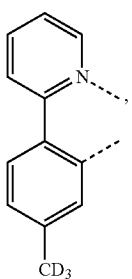

$L_{B37}$ 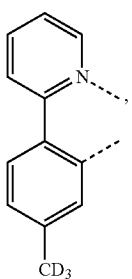

$L_{B38}$ 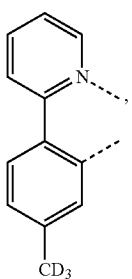

$L_{B39}$ 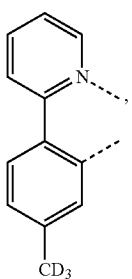

$L_{B40}$ 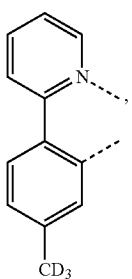, and

-continued $L_{B41}$ 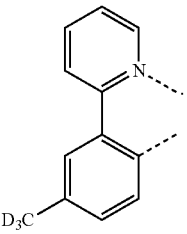

15. The compound of claim 13, wherein the compound has the formula $Ir(L_{Ak})_2(L_{Ci})$;
wherein $L_{Ak}$ is selected from $L_{A185}$-$L_{A190}$, $L_{A193}$-$L_{A198}$, $L_{A201}$-$L_{A206}$, $L_{A209}$-$L_{A214}$, $L_{A217}$-$L_{A222}$, $L_{A225}$-$L_{A230}$, $L_{A233}$-$L_{A238}$, $L_{A241}$-$L_{A246}$, $L_{A249}$-$L_{A254}$, $L_{A257}$-$L_{A262}$, $L_{A265}$-$L_{A270}$, $L_{A273}$-$L_{A278}$, $L_{A281}$-$L_{A286}$, $L_{A289}$-$L_{A294}$, $L_{A297}$-$L_{A302}$, $L_{A305}$-$L_{A310}$, $L_{A313}$-$L_{A318}$, $L_{A321}$-$L_{A326}$, $L_{A329}$-$L_{A334}$, $L_{A337}$-$L_{A342}$, $L_{A345}$-$L_{A350}$, $L_{A353}$-$L_{A358}$, $L_{A361}$-$L_{A366}$, $L_{A369}$-$L_{A374}$, $L_{A376}$-$L_{A378}$, $L_{A380}$-$L_{A382}$, $L_{A384}$-$L_{A386}$, $L_{A388}$-$L_{A390}$, $L_{A393}$-$L_{A398}$, $L_{A401}$-$L_{A408}$, $L_{A411}$-$L_{A414}$, $L_{A417}$-$L_{A422}$, $L_{A425}$-$L_{A430}$, $L_{A433}$-$L_{A438}$, $L_{A441}$-$L_{A446}$, $L_{A449}$-$L_{A454}$, $L_{A456}$-$L_{A458}$, $L_{A460}$-$L_{A462}$, $L_{A464}$-$L_{A466}$, $L_{A468}$-$L_{A470}$, $L_{A472}$-$L_{A474}$, $L_{A476}$-$L_{A478}$, $L_{A480}$-$L_{A482}$, $L_{A484}$-$L_{A486}$, $L_{A488}$-$L_{A490}$, $L_{A492}$-$L_{A494}$, $L_{A496}$-$L_{A498}$, $L_{A500}$-$L_{A502}$, $L_{A505}$-$L_{A510}$, $L_{A513}$-$L_{A518}$, $L_{A521}$-$L_{A526}$, $L_{A529}$-$L_{A534}$, $L_{A534}$-$L_{A542}$, $L_{A545}$-$L_{A550}$, $L_{A553}$-$L_{A558}$, $L_{A561}$-$L_{A566}$, $L_{A569}$-$L_{A574}$, $L_{A577}$-$L_{A582}$, $L_{A585}$-$L_{A590}$, $L_{A593}$-$L_{A598}$, $L_{A600}$-$L_{A602}$, $L_{A604}$-$L_{A606}$, $L_{A608}$-$L_{A610}$, $L_{A612}$-$L_{A614}$, $L_{A616}$-$L_{A618}$, $L_{A620}$-$L_{A622}$, $L_{A624}$-$L_{A626}$, and $L_{A628}$-$L_{A630}$; and
wherein $L_{Ci}$ is selected from $L_{C1}$ through $L_{C13}$ are defined as follows:

$L_{C1}$ 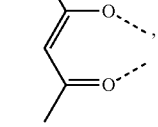

$L_{C2}$ 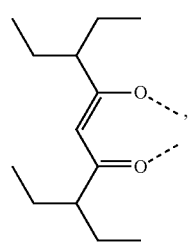

$L_{C3}$ 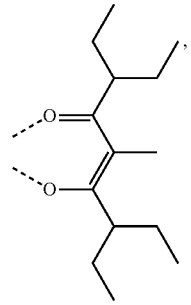

$L_{C4}$ 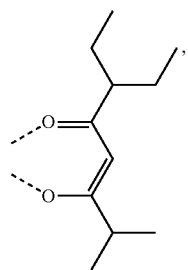

$L_{C5}$ 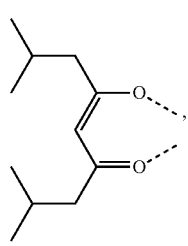

$L_{C6}$ 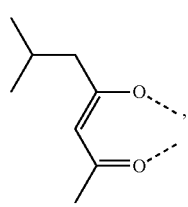

$L_{C7}$ 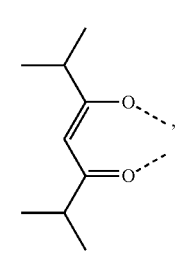

$L_{C8}$ 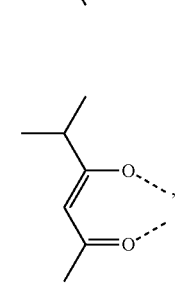

$L_{C9}$ 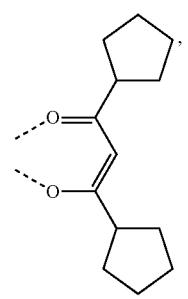

$L_{C10}$ 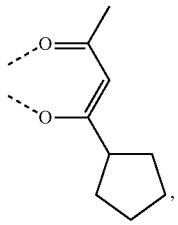

$L_{C11}$ 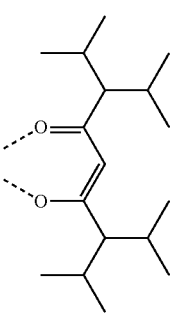

$L_{C12}$ 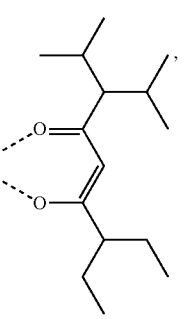

, and $L_{C13}$ 

16. The compound of claim 1, wherein each $R^E$ is independently selected from the group consisting of alkyl, cycloalkyl, partially and fully deuterated variations thereof, partially or fully fluorinated variations thereof, and combinations thereof.

17. A device comprising one or more organic light emitting devices, at least one of the one or more organic light emitting devices comprising:

an anode;

a cathode; and an organic layer, disposed between the anode and the cathode, comprising a compound having a formula $M(L_A)_x(L_B)_y(L_C)_z$:

wherein the ligand $L_A$ is

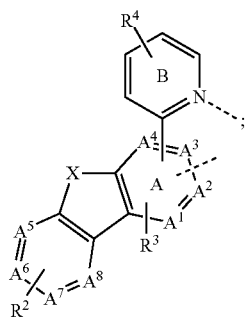

wherein the ligand $L_B$ is

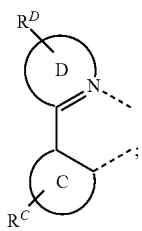

wherein the ligand $L_C$ is

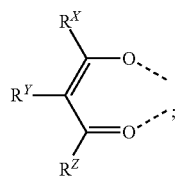

wherein M is a metal having an atomic number greater than 40;
wherein x is 1, or 2;
wherein y is 0, 1, or 2;
wherein z is 0, 1, or 2;
wherein x+y+z is the oxidation state of the metal M;
wherein $A^1$, $A^2$, $A^3$, $A^4$, $A^5$, $A^6$, $A^7$, and $A^8$ are carbon or nitrogen;
wherein ring B is bonded to ring A through a C—C bond;
wherein M is bonded to ring A through an M-C bond;
wherein X is selected from the group consisting of O, S, Se, CRR', and $NR^1$;
wherein rings C and D are each independently a 5 or 6-membered carbocyclic or heterocyclic ring;
wherein $R^3$ represents mono, or di-substitution, or no substitution;
wherein $R^2$, $R^C$, and $R^D$ each independently represent mono, di, tri, or tetra-substitution, or no substitution;
wherein $R^4$ represents mono, di, tri, or tetra-substitution;
wherein at least one $R^4$ is a triazine ring which is further substituted by $R^E$;
wherein $R^E$ represents mono or di-substitution;
wherein each of R, R', $R^1$, $R^2$, $R^3$, $R^4$, $R^C$, $R^D$, $R^X$, $R^Y$, $R^Z$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one $R^E$ is selected from the group consisting of alkyl, cycloalkyl, heteroalkyl, arylalkyl, silyl, alkenyl, cycloalkenyl, heteroalkenyl, alkynyl, aryl, heteroaryl, sulfanyl, sulfinyl, sulfonyl, phosphino, partially or fully deuterated variations thereof, and combinations thereof;
wherein any adjacent substitutents of R, R', $R^1$, $R^2$, $R^3$, $R^4$, $R^C$, $R^D$, $R^X$, $R^Y$, $R^Z$, and $R^E$ are optionally joined to form a ring; and
at least one of the following is true:
(i) at least one $R^E$ is selected from the group consisting of alkyl, cycloalkyl, partially or fully deuterated variations thereof, partially or fully fluorinated variations thereof, and combinations thereof, and
(ii) exactly one of $A^1$, $A^2$, $A^3$, $A^4$, $A^5$, $A^6$, $A^7$, and $A^8$ is nitrogen.

18. The device of claim 17, wherein the device is selected from the group consisting of a consumer product, an electronic component module, an organic light-emitting device, and a lighting panel.

19. The device of claim 17, wherein the organic layer is an emissive layer and the compound is an emissive dopant or a non-emissive dopant.

20. The device of claim 17, wherein the organic layer further comprises a host, wherein the host comprises at least one chemical group selected from the group consisting of triphenylene, carbazole, dibenzothiophene, dibenzofuran, dibenzoselenophene, azatriphenylene, azacarbazole, aza-dibenzothiophene, aza-dibenzofuran, and aza-dibenzoselenophene.

21. The device of claim 17, wherein the organic layer further comprises a host and the host is selected from the group consisting of:

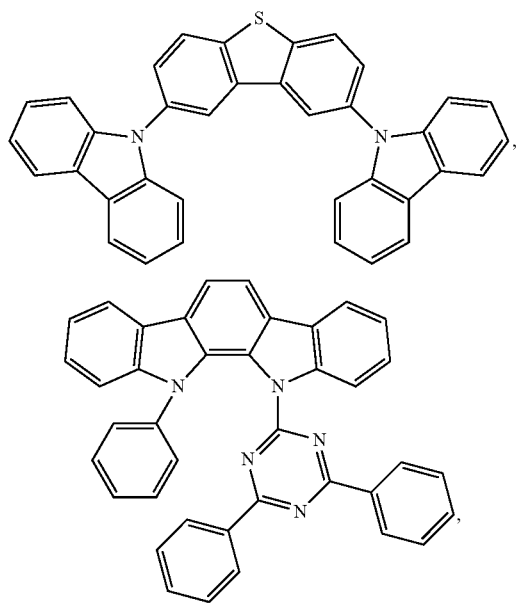

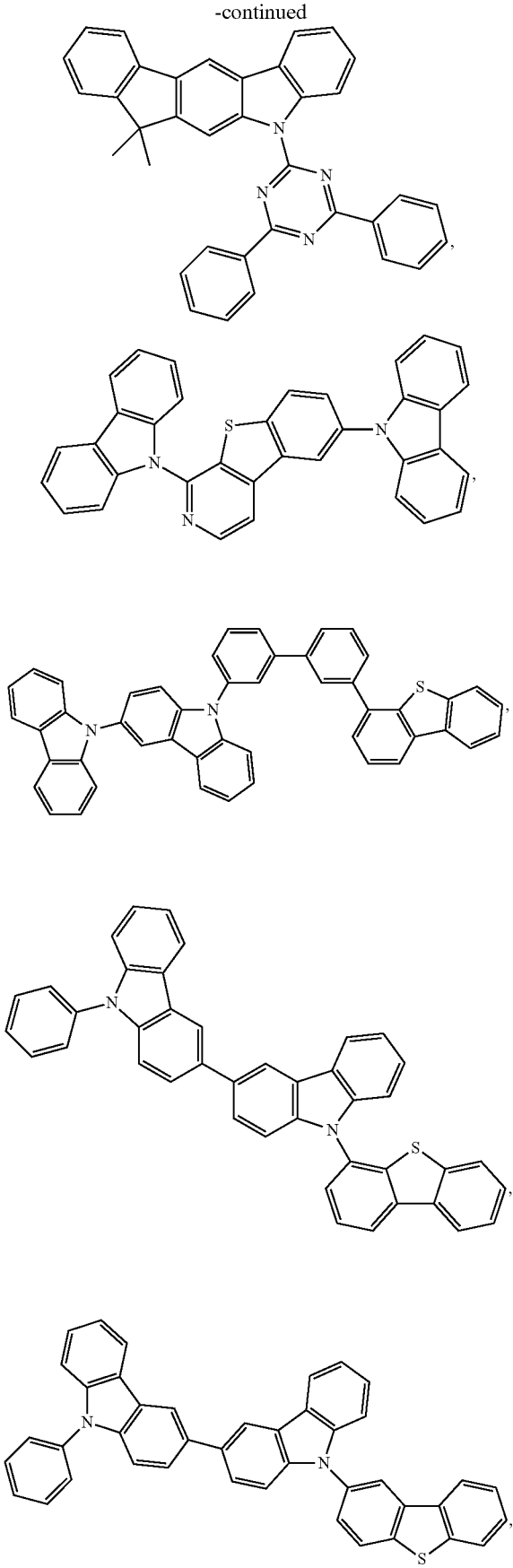

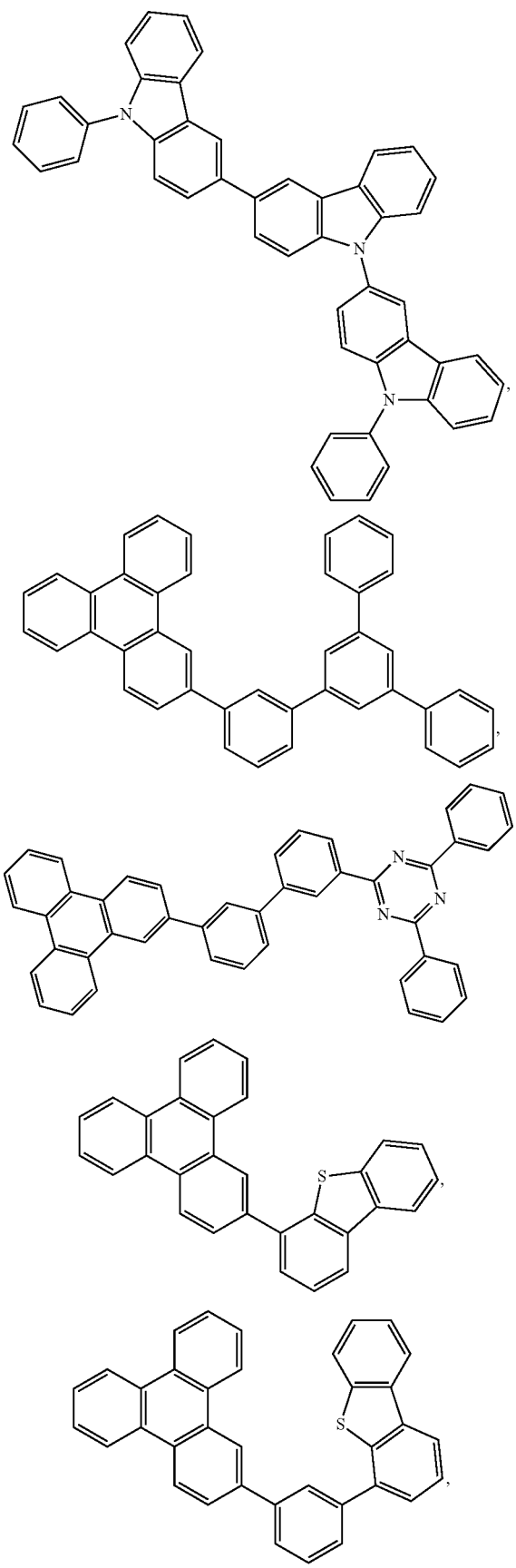
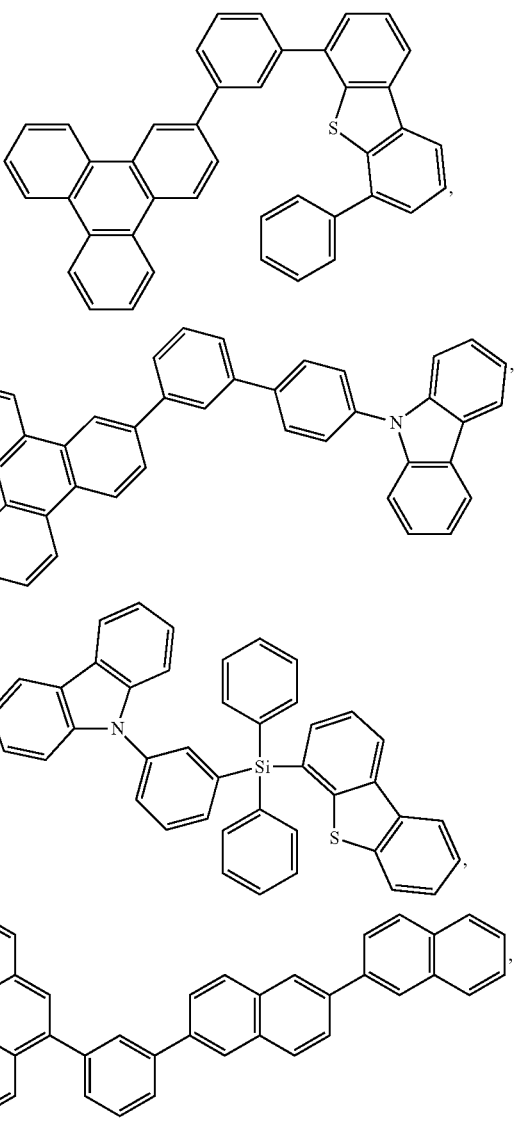
and combinations thereof.
22. A formulation comprising a compound having a formula $M(L_A)_x(L_B)_y(L_C)_z$:
wherein the ligand $L_A$ is
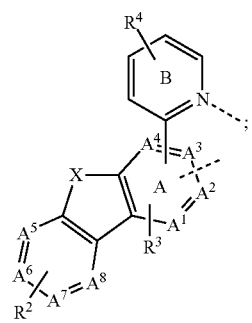

wherein the ligand $L_B$ is

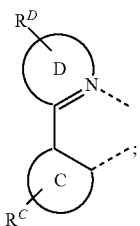

wherein the ligand $L_C$ is

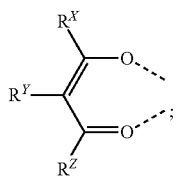

wherein M is a metal having an atomic number greater than 40;
wherein x is 1, or 2;
wherein y is 0, 1, or 2;
wherein z is 0, 1, or 2;
wherein x+y+z is the oxidation state of the metal M;
wherein $A^1$, $A^2$, $A^3$, $A^4$, $A^5$, $A^6$, $A^7$, and $A^8$ are carbon or nitrogen;
wherein ring B is bonded to ring A through a C—C bond;
wherein M is bonded to ring A through an M-C bond;
wherein X is selected from the group consisting of O, S, Se, CRR', and $NR^1$;
wherein rings C and D are each independently a 5 or 6-membered carbocyclic or heterocyclic ring;
wherein $R^3$ represents mono, or di-substitution, or no substitution;
wherein $R^2$, $R^C$, and $R^D$ each independently represent mono, di, tri, or tetra-substitution, or no substitution;
wherein $R^4$ represents mono, di, tri, or tetra-substitution;
wherein at least one $R^4$ is a triazine ring which is further substituted by $R^E$;
wherein $R^E$ represents mono or di-substitution;
wherein each of R, R', $R^1$, $R^2$, $R^3$, $R^4$, $R^C$, $R^D$, $R^X$, $R^Y$, $R^Z$, and $R^E$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof;
wherein at least one $R^E$ is selected from the group consisting of alkyl, cycloalkyl, heteroalkyl, arylalkyl, silyl, alkenyl, cycloalkenyl, heteroalkenyl, alkynyl, aryl, heteroaryl, sulfanyl, sulfinyl, sulfonyl, phosphino, partially or fully deuterated variations thereof, and combinations thereof;
wherein any adjacent substitutents of R, R', $R^1$, $R^2$, $R^3$, $R^4$, $R^C$, $R^D$, $R^X$, $R^Y$, $R^Z$, and $R^E$ are optionally joined to form a ring; and
at least one of the following is true:
(i) at least one $R^E$ is selected from the group consisting of alkyl, cycloalkyl, partially or fully deuterated variations thereof, partially or fully fluorinated variations thereof, and combinations thereof, and
(ii) exactly one of $A^1$, $A^2$, $A^3$, $A^4$, $A^5$, $A^6$, $A^7$, and $A^8$ is nitrogen.

* * * * *